(12) United States Patent
Mao et al.

(10) Patent No.: US 10,837,881 B2
(45) Date of Patent: *Nov. 17, 2020

(54) FLUORESCENT DYES, FLUORESCENT DYE KITS, AND METHODS OF PREPARING LABELED MOLECULES

(71) Applicant: Biotium, Inc., Fremont, CA (US)

(72) Inventors: Fei Mao, Fremont, CA (US); Wai-Yee Leung, San Ramon, CA (US); Ching-Ying Cheung, San Ramon, CA (US); Hye Eun Hoover, Alameda, CA (US)

(73) Assignee: BIOTIUM, INC., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/815,035

(22) Filed: Nov. 16, 2017

(65) Prior Publication Data

US 2018/0143113 A1 May 24, 2018

Related U.S. Application Data

(63) Continuation of application No. 14/218,439, filed on Mar. 18, 2014, now abandoned, which is a continuation of application No. 13/423,092, filed on Mar. 16, 2012, now Pat. No. 8,709,830.

(60) Provisional application No. 61/454,484, filed on Mar. 18, 2011.

(51) Int. Cl.

| | |
|---|---|
| *G01N 33/532* | (2006.01) |
| *G01N 33/533* | (2006.01) |
| *G01N 1/30* | (2006.01) |
| *G01N 33/58* | (2006.01) |
| *C09B 11/24* | (2006.01) |
| *C09B 57/00* | (2006.01) |
| *C09B 23/08* | (2006.01) |
| *C09B 57/02* | (2006.01) |
| *C09B 23/06* | (2006.01) |
| *G01N 33/53* | (2006.01) |
| *C07K 1/13* | (2006.01) |
| *C07K 17/06* | (2006.01) |
| *G01N 33/68* | (2006.01) |

(52) U.S. Cl.

CPC ............... *G01N 1/30* (2013.01); *C09B 11/24* (2013.01); *C09B 23/06* (2013.01); *C09B 23/083* (2013.01); *C09B 57/001* (2013.01); *C09B 57/02* (2013.01); *G01N 33/53* (2013.01); *G01N 33/532* (2013.01); *G01N 33/533* (2013.01); *G01N 33/582* (2013.01); *C07K 1/13* (2013.01); *C07K 17/06* (2013.01); *G01N 33/6854* (2013.01)

(58) Field of Classification Search

CPC ...... G01N 33/532; G01N 33/582; G01N 1/30; G01N 33/53; G01N 33/533; G01N 33/6854; C09B 11/24; C09B 23/06; C09B 23/083; C09B 57/001; C09B 57/02; C07K 1/13

See application file for complete search history.

(56) References Cited

U.S. PATENT DOCUMENTS

| | | |
|---|---|---|
| 4,845,039 A | 7/1989 | Pauwels et al. |
| 5,397,699 A | 3/1995 | Davis et al. |
| 5,403,750 A | 4/1995 | Braatz et al. |
| 5,527,686 A | 6/1996 | Fitzpatrick et al. |
| 5,710,009 A | 1/1998 | Fitzpatrick et al. |
| 5,772,699 A | 6/1998 | Boyer |
| 7,405,281 B2 | 7/2008 | Xu et al. |
| 8,709,830 B2 | 4/2014 | Mao et al. |
| 2004/0106135 A1 | 6/2004 | Mukherjee et al. |
| 2007/0134685 A1 | 6/2007 | Mauro et al. |
| 2008/0160535 A1 | 7/2008 | Gold et al. |
| 2008/0176213 A1 | 7/2008 | Mauro et al. |
| 2010/0009342 A1 | 1/2010 | Mauro et al. |
| 2012/0329068 A1 | 12/2012 | Mao et al. |
| 2015/0056632 A1 | 2/2015 | Mao et al. |

FOREIGN PATENT DOCUMENTS

| | | |
|---|---|---|
| EP | 0913691 A1 | 5/1999 |
| WO | WO-2007030521 A1 | 3/2007 |
| WO | WO-2011149415 A1 | 12/2011 |
| WO | WO-2012129128 A1 | 9/2012 |

OTHER PUBLICATIONS

Thermo Fisher Scientific. Instructions NHS and Sulfo-NHS. Thermo Fisher Scientific Inc. 2009, Pierce Biotechnology, 3747 Meridian Road, Rockford, IL 61105 (Year: 2009).*

Benashski, et al. Investigation of protein-protein interactions within flagellar dynein using homobifunctional and zero-length crosslinking reagents. Methods. 2000; 22:365-371.

Brinkley et al. A brief survey of methods for preparing protein conjugates with dyes, haptens, and cross-linking reagents. Bioconjug Chem 3(1):2-13 (1992).

Delcroix, et al. A multienzyme network functions in intestinal protein digestion by a platyhelminth parasite. Journal of Biological Chemistry 281.51 (2006): 39316-39329.

European search report and opinion dated Nov. 10, 2014 for EP Application No. 12761364.4.

(Continued)

*Primary Examiner* — Shafiqul Haq

(74) *Attorney, Agent, or Firm* — Wilson Sonsini Goodrich & Rosati

(57) ABSTRACT

The present invention provides methods, compositions, and kits useful in preparing labeled molecules, which are useful in the detection of binding partners.

19 Claims, 8 Drawing Sheets

(56) References Cited

OTHER PUBLICATIONS

Green, et al. Quantitative evaluation of the lengths of homobifunctional protein cross-linking reagents used as molecular rulers. Protein Science. 2001; 10:1293-1304.
International search report and written opinion dated Jul. 27, 2012 for PCT Application No. US12/29564.
Le, et al. Antibody functionalization with a dual reactive hydrazide/click crosslinker. Analytical Biochemistry. 2013; 435:68-73.
Madler, et al. Does chemical cross-linking with NHS esters reflect the chemical equilibrium protein-protein noncovalent interations in solutions? J. Am. Soc. Mass Spectrom. 2010; 21(10):1775-1783.
Notice of allowance dated Dec. 11, 2013 for U.S. Appl. No. 13/423,092.
Office action dated Apr. 16, 2013 for U.S. Appl. No. 13/423,092.
Office action dated Jun. 9, 2016 for U.S. Appl. No. 14/218,439.
Office action dated Jul. 25, 2017 for U.S. Appl. No. 14/218,439.
Office action dated Dec. 21, 2016 for U.S. Appl. No. 14/218,439.
Petrotchenko, et al. BiPS, a photocleavable, isotopically coded, fluorescent cross-linker for structural proteomics. Molecular and Cellular Proteomics. 2008; 8(2):273-286.
Trester-Zedlitz, et al. A modular cross-linking approach for exploring protein interactions. J. Am. Chem. Soc. 2003; 125(9):2416-2425.

\* cited by examiner

FLUORESCENT DYES, FLUORESCENT DYE KITS, AND METHODS OF PREPARING LABELED MOLECULES

CROSS-REFERENCE

This application is a continuation of U.S. Utility Application No. 14/218,439, filed Mar. 18, 2014, now abandoned, which is a continuation of U.S. Utility Application No. 13/423,092, filed Mar. 16, 2012, now U.S. Pat. No. 8,709,830, which claims the benefit of U.S. Provisional Application No. 61/454,484, filed Mar. 18, 2011, each of which applications are incorporated herein by reference in their entirety.

BACKGROUND OF THE INVENTION

Fluorescent dyes are widely used in biological research and medical diagnostics. Fluorescent dyes are superior to conventional radioactive materials because fluorescent dyes are less expensive and less toxic, and can typically be detected with sufficient sensitivity. In particular, a diversity of fluorophores with a distinguishable color range has made it more practical to perform multiplexed assays capable of detecting multiple biological targets at the same time. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay. Moreover, the low toxicity of fluorescent dyes provides ease of handling in vitro, and also renders it safer for imaging biological activities in vivo.

Fluorescent dyes for applications as described above generally derive from joining a dye and an agent that is capable of binding to a given target or binding partner. Current processes for joining dyes to such binding agents, antibodies being one example, typically require purification of the antibody away from standard buffer components, long reaction times, and purification of the labeled antibody once the reaction is complete. Thus, current processes consume valuable time and resources, and there is a need for improvements in the labeling of binding agents.

SUMMARY OF THE INVENTION

In various embodiments, a method for preparing a labeled protein comprises: (a) providing i) a reactive dye, such as an amine-reactive dye, or a reactive detectable label, such as an amine-reactive detectable label, and ii) a first amine; (b) combining the amine-reactive dye and the first amine, in a buffer, with a sample solution comprising a target protein, the target protein comprising a second amine, to form a combined solution; and (c) allowing the combined solution to react, thereby producing the labeled protein. For example, the amine-reactive detectable label reacts more strongly with the second amine than the first amine. In various embodiments, the combined solution reacts for less than 3, 2, 1, 0.5 or fewer hours. In various embodiments, the reaction is essentially complete in about 30 minutes or less. The reactive detectable label may be a fluorescent dye, biotin, digoxin, a hapten or an epitope. In some embodiments, the reactive detectable label is not a dye. The reactive group of the reactive detectable label may be an amine-reactive group. In some embodiments, the amine-reactive detectable dye or amine-reactive detectable label has a molecular weight of less than about 10000, 5000, 3000, 2000, or 1000 Da. For example, the amine-reactive detectable dye or amine-reactive detectable label has a molecular weight of less than about 5000 Da.

In various embodiments, the target protein is an antibody, for example an antibody fragment, a recombinant antibody, a non-human antibody, a chimeric antibody, a humanized antibody, or a fully human antibody.

The buffer may be selected from the group consisting of a sodium carbonate buffer, a sodium bicarbonate buffer, a borate buffer, a Tris buffer, a MOPS buffer, a HEPES buffer, or a combination thereof. The buffer may be alkaline. For example, the pH of the buffer may be in the range from 7 to 10 or the pH of the combined solution may be greater than 7.8.

In various embodiments, the first amine is a primary or secondary amine, such as an aliphatic amine capable of competing in the labeling reaction. For example, the first amine may be tris(hydroxymethyl)aminomethane (Tris), a weak primary aliphatic amine. The amine, such as Tris, may be present in the buffer at a concentration of greater than 20 mM, or may be formulated to be present in the combined solution at a concentration of greater than 1 mM, for example formulated to about 10 mM.

The reactive dye may comprises one or more activated esters, such as a N-hydroxy succinimidyl ester, N-hydroxy sulfosuccinimidyl ester, p-sulfo-tetrafluorophenol ester, or a combination thereof. The reactive dye may comprise one or more sulfonate groups and/or one or more water-soluble polymer groups such as polyethylene glycol. In various embodiments, the water-soluble polymer group has a molecular weight of 300-10000 Daltons, or 450-5000 Daltons. Reactive dyes may be selected from the group consisting of: a CF dye, an Alexa Fluor dye, a DyLight Dye, a Cy dye, an IRDye, a HiLyte dye, a sulfonated and/or pegylated coumarin dye, a sulfonated and/or pegylated xanthenes dye, a sulfonated or/pegylated cyanine dye, and a sulfonated and/or pegylated pyrene dye. In various embodiments, the dye has a chemical structure according to any of Compounds 1-128.

In various embodiments, a fixed amount of reactive label is used to label a target protein in any amount within a certain range, resulting in a labeled target protein that avoids being either under labeled or over labeled. For example, the sample solution comprises between about 1 µg and about 1000 µg, or between about 5 µg and about 200 µg, or between about 5 µg and about 20 µg, or between about 20 µg and about 50 µg, or between about 50 µg and about 100 µg, or between about 50 µg and about 200 µg, or between about 100 µg and about 200 µg of said target protein. The ratio of amount of protein in microgram (µg) to the amount of reactive dye in nanomole (nmol) may be from 30:1 to 1:1. The sample solution may further comprise one or more non-target proteins. For example, the ratio of the combined weight of target and non-target protein in microgram (µg) to the amount of reactive dye in nanomole (nmol) may be from 30:1 to 1:1. In various embodiments, the ratio of the weight in microgram (µg) of target protein to non-target protein is from about 10:1 to about 1:10.

In various embodiments, a method of preparing a protein-protein conjugate is provided comprises:

(a) providing i) an amine-reactive bifunctional crosslinker additionally comprising a hydrolysis-resistant functional group; and optionally ii) a first amine; (b) combining, in a first buffer, the amine-reactive bifunctional crosslinker and, if present, the first amine, with a sample solution comprising a target protein, the target protein comprising a second amine, to form a first combined solution; (c) allowing the combined solution to react, thereby producing a target protein functionalized with a hydrolysis-resistant functional group; (d) in a second buffer, combining the target protein functionalized with the hydrolysis-resistant functional group with a reporter protein comprising a hydrolysis-resistant reactive group, wherein said hydrolysis-resistant functional group reacts with said hydrolysis-resistant reactive group, thereby forming a protein-protein conjugate. For example, the amine-reactive detectable label reacts more strongly with the second amine than the first amine; and step (d) is performed without purification of the combined solution from step (c).

In various embodiments, the first buffer is any aqueous buffer having a pH from about 7 to about 10. The buffer may comprise one or more primary or secondary aliphatic amine. For example, the buffer may be a bicarbonate buffer comprising Tris.

The amine-reactive group of the bifunctional crosslinker may be an activated ester, such as succinimidyl ester, and the hydrolysis-resistant functional group of the crosslinker may be selected from an aldehyde, a ketone, an azide, an alkyne, a phosphine participating in Staudinger conjugation, a diene, a dienophile, a protected hydrazino, a protected aminooxy. For example, the crosslinker may be a bifunctional molecule comprising a succinimidyl ester and an aldehyde group.

In various embodiments, as with the target protein labeling using a reactive SDL above, the ratio of amount of protein in microgram (μg) to the amount of the crosslinker in nanomole (nmol) may be from 30:1 to 1:1. The sample solution may further comprise one or more non-target proteins. For example, the ratio of the combined weight of target and non-target protein in microgram (μg) to the amount of crosslinker in nanomole (nmol) may be from 30:1 to 1:1. In various embodiments, the ratio of the weight in microgram (μg) of target protein to non-target protein is from about 10:1 to about 1:10.

In various embodiments, the reporter protein is generally a protein molecule that can produce a detectable signal either by itself or on interacting with another molecule. For example, protein tags may include but are not limited to fluorescent proteins, tandem dyes and enzymes. In some embodiments, the fluorescent proteins are phycobiliproteins, such as R-phycoerythrine, tandem dyes are fluorescent resonance energy transfer (FRET) dyes typically prepared by covalently labeling fluorescent proteins with one or more synthetic organic dyes, such as the ones mentioned above. In some embodiments, the enzymes are horseradish peroxidase or alkaline phosphatase. The hydrolysis-resistant reactive group on the reporter protein is generally a reactive group capable of reacting with the hydrolysis-resistant functional group of the crosslinker to form a covalent bond. Non-limiting suitable hydrolysis-resistant reactive groups include an aldehyde, a ketone, an azido, an alkyne, a phosphine participating in Staudinger conjugation, a diene, a dienophile, a hydrazone and an oxime.

In various embodiments, the second buffer may be a buffer having a pH from about 4 to about 10. According to some embodiments, the second buffer may comprise one or more catalyst that facilitates the conjugation of the protein tag to the functionalized target protein. For example, the second buffer may be an acidic buffer having a pH from about 4 to about 6.8 and comprising aniline or an aniline derivative for catalyzing an aminooxy to an aldehyde conjugation to form an oxime linkage.

In various embodiments, a pretreatment purification step is excluded. For example, in various embodiments, protein A-based chromatography, size-exclusion chromatography, and ultra membrane filtration are not performed.

Methods of staining one or more biological targets are also disclosed. Such methods may comprise (a) preparing one or more labeled proteins according to the methods described herein, wherein each of said one or more labeled proteins comprises a targeting moiety that binds to a binding partner associated with one or more of said biological targets; and, (b) exposing said one or more biological targets to said one or more labeled proteins, such that said labeled protein binds to said binding partner thereby staining said one or more biological targets. In other embodiments, methods are provided of staining a biological target comprising (a) preparing one or more labeled proteins according to the methods described herein, and (b) exposing said one or more biological targets to said one or more labeled proteins, such that said labeled protein binds to said one or more biological targets thereby staining said one or more biological targets. In various embodiments, step (b) is performed without purification of said one or more labeled proteins from step (a). In various embodiments, the use of a quencher is excluded. Staining may take place in vivo or in vitro, as desired. In various embodiments, two or more labeled proteins comprise different dyes, such that said exposing step (b) renders said different binding partners optically distinguishable.

The products of staining may be analyzed by, for example, flow cytometry, western blot, or by microscopy. For example, the products may be analyzed using a fluorescence activated cell sorter.

In various embodiments, diagnosing a condition of a subject based on analysis of stained biological targets is performed. Alternatively, a method for evaluating the efficacy of a test compound is disclosed.

A kit for preparing a labeled protein is provided which may comprise (a) a buffer comprising a first amine, for example a primary or secondary aliphatic amine; (b) one or more reactive dyes or reactive detectable labels for labeling one or more target proteins; (c) a storage buffer; and, (d) instructions in one or more than one language. The kit comprises components according to the methods described herein. For example, one or more of dyes may be present as an amine reactive dye. Buffer may be selected from the group consisting of: a sodium carbonate buffer, a sodium bicarbonate buffer, a borate buffer, a Tris buffer, a MOPS buffer, a HEPES buffer, or a combination thereof. In various embodiments, the buffer is alkaline, for example, with a pH in the range of 7 to 10. The amine may be tris(hydroxymethyl)aminomethane (Tris), present in a concentration, for example, of greater than 20 mM, or in a concentration such that upon addition to a protein, the concentration would be greater than 20 mM.

Activated esters are encompassed, such as N-hydroxy succinimidyl ester, N-hydroxy sulfosuccinimidyl ester, p-sulfo-tetrafluorophenol ester, or a combination thereof.

A kit for preparing reporter protein-labeled proteins is also provided which may comprise (a) an alkaline buffer comprising a first amine, such as a primary or secondary aliphatic amine; (b) a bifunctional crosslinker comprising an amine-reactive group and a hydrolysis-resistant functional group; (c) a reporter protein functionalized with a pairing hydrolysis-resistant reactive group; (d) a second buffer suitable for the hydrolysis-resistant functional group and hydrolysis-resistant reactive group to react to form a covalent linkage; (e) a storage buffer; and (f) instructions in one or more than one language.

In various embodiments, buffer and dye are present in an amount sufficient to permit labeling of 5 µg-200 µg of a target protein. Storage buffer may be present, for example, with a stabilizer. Such stabilizers may include bovine serum albumin, gelatin, glycerol, sodium azide, tris, or a combination thereof.

In various embodiments, the kit includes a separation device for purifying a labeled target protein. For example, the separation device may be a size exclusion chromatography column. In various embodiments, a stain stabilizing reagent for enhancing dye fluorescence is present in the kit.

INCORPORATION BY REFERENCE

All publications, patents, and patent applications mentioned in this specification are herein incorporated by reference to the same extent as if each individual publication, patent, or patent application was specifically and individually indicated to be incorporated by reference. The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)), each of which are incorporated by reference for their teachings of conventional techniques.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DEFINITIONS

Figure 1:
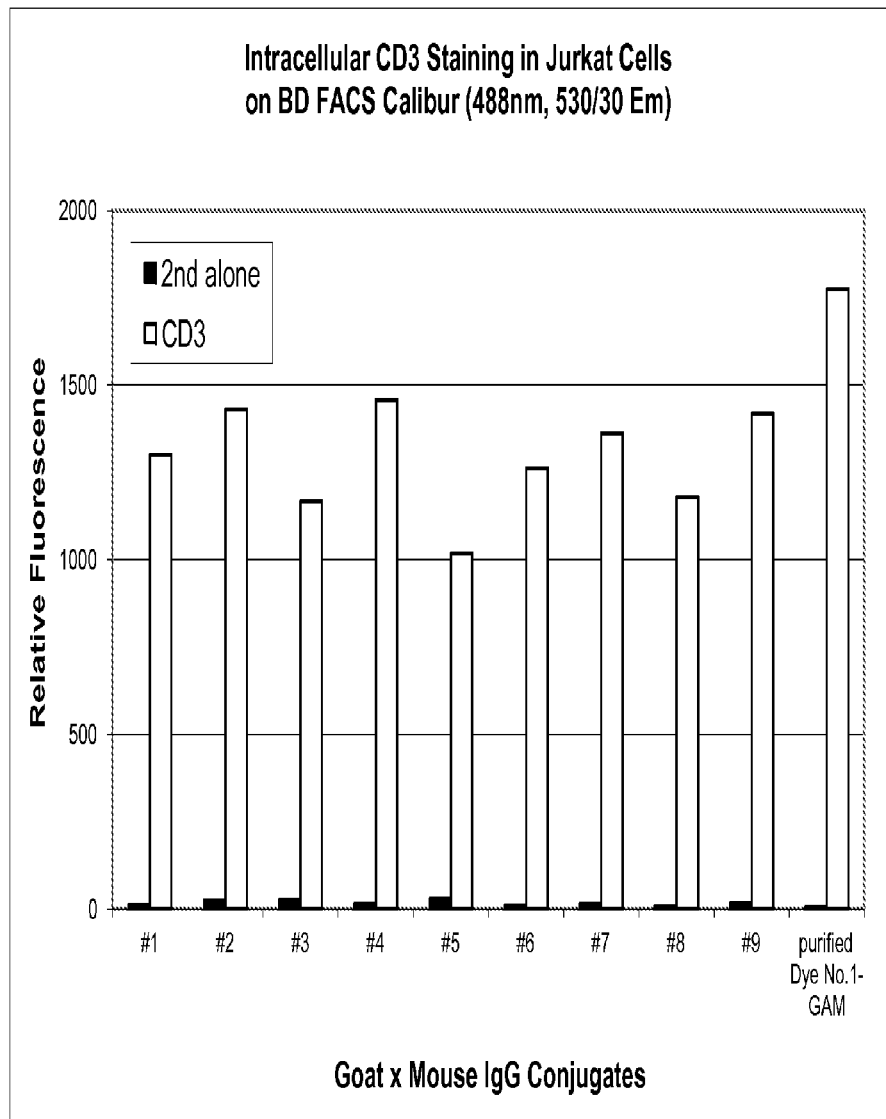
FIG. 1 shows the results of a flow cytometry analysis of cells stained with secondary antibodies labeled according to methods of the invention.

The terms "polypeptide", "peptide" and "protein" are used interchangeably herein to refer to polymers of amino acids of any length. The polymer may be linear, cyclic, or branched. The polymer may comprise modified amino acids, and it may be interrupted by non-amino acids. The terms also encompass amino acid polymers that have been modified, for example, via sulfonation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "binding agent" is a molecule that exhibits binding selectivity towards a binding partner or a target molecule to which it binds. A binding agent may be a biomolecule such as a polypeptide such as an antibody or protein, polypeptide-based toxin, amino acid, nucleotide, polynucleotides including DNA and RNA, lipids, and carbohydrates, or a combination thereof. A binding agent may also be a hapten, drug, ion-complexing agent such as metal chelators, microparticles, synthetic or natural polymers, cells, viruses, or other fluorescent molecules including the dye molecule according to the invention.

A "targeting moiety" is the portion of the binding agent that binds to a binding partner. A targeting moiety may be, without limitation, a nucleotide sequence within a polynucleotide that selectively binds to another polynucleotide or polypeptide. Another non-limiting example of a targeting moiety may be a polypeptide sequence within a larger polypeptide sequence which binds specifically to a polynucleotide sequence or a second polypeptide sequence. A targeting moiety may be a small molecule or structural motif which will bind to a protein receptor, another small molecule motif, or complexing agent, without limitation. The selective binding may be a specific binding event.

A "binding partner" is a molecule or particle which is bound by the targeting moiety. It can be a cell, virus, fragment of a cell, antibody, fragment of an antibody, peptide, protein, polynucleotide, antigen, small molecule, lipid, carbohydrate, or a combination thereof. It may be bound selectively or specifically by the binding agent. In general, binding is considered "specific" when binding between a binding partner and the target of the binding partner (a binding pair) is at least two times greater, such as more than 10, 1000, 1000, 10000 times greater, than background resulting from binding to non-target molecules in a sample.

One skilled in the art will realize that such a functional group may also be called a reactive group; As used herein, the terms "reactive group" and "functional group" refer to chemical groups that can undergo chemical reactions with other chemical moieties under certain conditions. When a first reactive group reacts with such a chemical moiety (for example a second reactive group), one or more covalent bonds is formed. In such cases, the second reactive group will generally be termed a "functional group".

As used herein, the term "about" generally means within 10%, 5%, 1%, or 0.5% or a given value or range. Alternatively, the term "about" refers to an acceptable standard error of the mean, when considered by one of ordinary skill in the art.

The term "aliphatic" refers to an organic compound or radical characterized by a straight chain or branched chain structure, or closed ring structure, any of which contain saturated carbon bonds and optionally one or more unconjugated carbon-carbon unsaturated bonds, such as a carbon-carbon double bond.

DETAILED DESCRIPTION OF THE INVENTION

In some aspects, the present invention provides methods for labeling target proteins with either a reactive dye, a reactive detectable label, or with a reporter protein. The resulting labeled target protein can be used, for example, in subsequent biological staining or other experiments. In some embodiments, the resulting labeled target protein is used without further purification.

In some embodiments, target proteins that are labeled by the methods of the invention are members of a binding pair, such as a binding agent and a target. In some embodiments, the binding agent is an antibody and the target is an antigen. The term "antibody" as used herein refers to immunoglobulin molecules and immunologically active portions of immunoglobulin molecules, i.e., molecules that contain an antigen-binding site which specifically binds ("immunoreacts with") an antigen. Non-limiting examples include an antibodies, antibody fragments, recombinant antibodies, non-human antibodies, chimeric antibodies, humanized antibodies, or fully human antibodies. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

Detectable labels, such as amine-reactive detectable labels, are generally molecules that can directly or indirectly produce or result in a detectable signal either by themselves or upon interaction with another molecule. In some embodiments, detectable labels have a molecular weight of less than about 5000 dalton. Non-limiting examples of detectable labels include labels comprising fluorescent dyes, biotin, digoxin, haptens and epitopes.

Dyes useful in labeling proteins are known in the art. In general, a dye is a molecule, compound, or substance that can provide an optically detectable signal, such as a colorimetric, luminescent, bioluminescent, chemiluminescent, phosphorescent, or fluorescent signal. In some embodiments, the dye is a fluorescent dye. Non-limiting examples of dyes, some of which are commercially available, include CF dyes (Biotium, Inc.), Alexa Fluor dyes (Invitrogen), DyLight dyes (Thermo Fisher), Cy dyes (GE Healthscience), IRDyes (Li-Cor Biosciences, Inc.), and HiLyte dyes (Anaspec, Inc.). Other non-limiting example of dyes include any of Compounds 1-128, listed in Tables 1-4 and the Examples. In some embodiments, the excitation and/or emission wavelengths of the dye are between 350 nm to 900 nm, or between 400 nm to 700 nm, or between 450-650 nm.

In some embodiments, the dye is water soluble. In some embodiments, the dye comprises about, less than about, or more than about 1, 2, 3, 4, 5, 6, 7, 8, 9, 10, or more sulfonate groups. In some embodiments, the dye comprises about, less than about, or more than about 1, 2, 3, 4, 5, 6, 7, 8, 9, 10, or more water-soluble polymer groups, such as polyethylene glycol (PEG). A water soluble polymer group can have any suitable molecular weight, such as 300-10000 Daltons, including 450-5000 Daltons. In some embodiments, a water soluble polymer group has a molecular weight of about, more than about, or less than about 200, 300, 400, 450, 500, 600, 700, 800, 900, 1000, 1500, 2000, 3000, 4000, 5000, 6000, 7000, 8000, 9000, 10000, 20000, 30000, 40000, 50000, or more Daltons, or any range between any two such weights. In some embodiments, the dye is sulfonated and/or pegylated, such as in a sulfonated and/or pegylated coumarin dye, a sulfonated and/or pegylated xanthene dye, a sulfonated and/or pegylated cyanine dye, or a sulfonated and/or pegylated pyrene dye.

In some embodiments the dye is an amine reactive dye, comprising one or more groups that react to form an amide bond with an amine. In some embodiments, the amine reactive dye comprises about, less than about, or more than about 1, 2, or 3 amine-reactive groups. In some embodiments, the amine reactive group is an activated ester. Examples of activated esters include, but are not limited to, N-hydroxy succinimidyl ester, N-hydroxy sulfosuccinimidyl ester, p-sulfo-tetrafluorophenol ester, pentafluorophenyl esters, tetrafluorophenyl esters, p-nitrophenyl esters, 2,4-dinitrophenyl ester, 4-nitrophenyl ester, 3-Hydroxy-3,4-dihydro-4-oxo-1,2,3-benzotriazine (HODhbt), carboxylic acids activated using common carbodiimides such as but not limited to diisopropylcarbodiimide (DIPCDI), N,N'-dicyclohexylcarbodiimide (DCC), 1-ethyl-3-(3'-dimethylaminopropyl)carbodiimide hydrochloride (EDC); and carboxylic acids activated with an uronium salt or a phosphonium salt, such as but not limited to O-Benzotriazole-N,N,N',N'-tetramethyluronium hexafluorophosphate (HBTU), O-(Benzotriazol-1-yl)-N,N,N,N-tetramethyluronium tetrafluoroborate (TBTU), 2-(6-Chloro-1H-benzotriazole-1-yl)-1,1,3,3-tetramethylaminium hexafluorophosphate (HCTU), (2-(6-Chloro-1H-benzotriazole-1-yl)-1,1,3,3-tetramethylaminium tetrafluoroborate) (TCTU), 2-(1H-7-Azabenzotriazol-1-yl)-1,1,3,3-tetramethyl uronium hexafluorophosphate (HATU), 1-benzotriazolyoxytris-(dimethylamino)phosphonium hexafluorophosphate (BOP) benzotriazol-1-yl-oxytripyrrolidinophosphonium hexafluorophosphate (PYBOP); or combinations thereof.

Bifunctional crosslinkers for use in the invention generally comprise two reactive groups capable of reacting with target and reporter proteins. For example, at least one of the two reactive groups is an amine-reactive group. In some embodiments, a bifunctional crosslinker comprises an amine-reactive group and a hydrolysis-resistant functional group. The amine-reactive group can react with an amine group within a target protein, thereby conjugating the crosslinker to the amine group of the target protein via an amide bond. The amine-reactive group can be an activated ester as described herein. Any of the activated esters described as suitable for use with the amine-reactive dyes or amine-reactive detectable labels are also suitable for use with the amine-reactive group of the crosslinker. As an example, the activated ester may be an N-hydroxy succinimidyl ester.

Hydrolysis-resistant functional groups can react with the reporter protein, thereby attaching the other end of the crosslinker to the reporter protein. In some embodiments, the functional group is hydrolysis-resistant. For example, a hydrolysis-resistant functional group or hydrolysis-resistant reactive group is at least 90% intact in a buffer, such as the first buffer of the methods of the invention, for at least 24 hours, or for at least 1 month, or for at least 3 months. Generally, hydrolysis-resistant functional groups are compatible with the amine-reactive group of the crosslinker such that that they do not react with each other. Since the amine-reactive group is an electrophile, the hydrolysis-resistant functional group of the crosslinker is generally not a nucleophile. Non-limiting examples of functional groups that are hydrolysis-resistant and non-nucleophilic include aldehydes, ketones, azido, alkyne, phosphines participating in Staudinger conjugation, dienes, dienophiles, protected hydrazine and protected aminooxy. Examples of pairs of hydrolysis-resistant functional groups and reactive groups that can react to form a covalent bond are listed below:

| Functional Group | Reactive Group | Bond formation reaction |
|---|---|---|
| aldehyde | aminooxy | oxime formation |
| aldehyde | hydrazino | hydrazone formation |
| ketone | aminooxy | oxime formation |
| ketone | hydrazino | hydrazone |
| aldehyde | acetone protected aminooxy | oxime formation |
| aldehyde | acetone protected hydrazino | hydrazone formation |
| ketone | acetone protected aminooxy | oxime formation |
| ketone | acetone protected hydrazino | hydrazone formation |
| azido | alkyne | Click chemistry |
| diene | dienophile | Diels-Alder reaction |
| Azido | phosphine | Staudinger reaction |

In some embodiments, the hydrolysis-resistant functional group excludes maleimide or disulfide linker-forming groups such as pyridyldisulfide. In one embodiment, the bifunctional crosslinker comprises an N-hydroxy succinimidyl ester and an aldehyde functional group.

Buffers useful for labeling the target protein with an amine-reactive dye, an amine-reactive detectable label, or with a bifunctional crosslinker (i.e., a first reaction buffer) in the methods of the invention include any that support a labeling reaction as described herein. In some embodiments, the buffer is an alkaline buffer, having a pH greater than about 7, for example having a pH from about 7 to about 14, such as a pH of about, more than about 7, 7.1, 7.2, 7.3, 7.4, 7.5, 7.6, 7.7, 7.8, 7.9, 8.0, 8.5, 9, 9.5, 10, 10.5, 11, 11.5, 12, 12.5, 13, 13.5, or 14. In some embodiments the buffer has a pH of about, more than about, or less than about 4, 4.5, 5, 5.5, 6, or 6.5. Non-limiting examples of useful buffers include sodium carbonate buffers, sodium bicarbonate buffers, borate buffers, tris buffers, MOPS buffers, HEPES buffers, and combinations thereof. In some embodiments, the buffer is of a concentration such that the combined solution has a pH from about 6 to about 11, such as from about 7.9 to about 9.8, or from about 8 to about 9. In some embodiments, the pH of the combined solution about, more than about, or less than about 6, 6.5, 7, 7.5, 7.6, 7.7, 7.8, 7.9, 8.0, 8.1, 8.2, 8.3, 8.4, 8.5, 8.6, 8.7, 8.8, 8.9, 9.0, 10, 10.5, 11, or more. In some embodiments, the buffer has a starting concentration that is about, more than about, or less than about 2-fold, 5-fold, 10-fold, 20-fold, 30-fold, 40-fold, 50-fold, or more than the concentration of the buffer in the combined solution. In one example, a 10× reaction buffer comprises 500 mM sodium bicarbonate and 100 mM Tris.

In some embodiments, the buffer used in the invention comprises a first amine, for example an aliphatic amine, capable of competing with a second amine group of the target protein in reacting with the reactive dye or crosslinker described above. In some embodiments, the first amine is a primary or secondary amine, e.g. a primary or secondary aliphatic amine. In general, a first amine is at least 50% less reactive than the w amine of lysine in an amide formation reaction with an activated carboxylic acid ester, such as 60%, 70%, 80%, 90%, or less reactive. Reactivity can be measured, for example, as a reaction rate in an aqueous solution. A non-limiting example of a first amine includes tris(hydroxymethyl)aminomethane (Tris). In various embodiments, a first amine with the specified reactivity is a primary or secondary amine. In some embodiments, the amine acts as a regulating agent of the labeling reaction such that the fraction of labeled to unlabeled amine groups in the target protein and/or the number of labels per target protein are kept within a desired range. For example, when the amount of antibody is relatively high, most of the dye, label, or crosslinker molecules react with the antibody molecules while a side-reaction between the first amine and the dye, label, or crosslinker is minimal, such that the antibody is sufficiently labeled. In another example, when the amount of target protein (e.g. antibody) is relatively low, the side-reaction between the first amine and the dye, label, or crosslinker is relatively increased, such that consumption of the dye, label, or crosslinker by the first amine reduces the likelihood that the small amount of antibody will be overly labeled. In some embodiments, more than about 95%, 96%, 97%, 98%, 99%, 99.5%, or more of the target protein in a sample is labeled. In some embodiments, each target protein is labeled with about, or more than about 1, or with about, more than about, or less than about, 2, 3, 4, 5, 6, 7, 8, 9, 10, 15, or 20 dye, label or crosslinker molecules. In some embodiments, 80%, 85%, 90%, 95%, 96%, 97%, 98%, 99%, 99.5%, or more of labeled target protein in a sample have the same number of dye molecules. While not wishing to be bound by theory, it is believed that in circumstances where a target protein is mixed with a non-target protein (such as an antibody stabilized with bovine serum albumin (BSA), and both the target protein and non-target protein are labeled equally in terms of labeling efficiency per amine basis on each protein, a staining process may still tolerate the more or less equivalent labeling. For example, in one embodiment, non-target protein may not have affinity for a subsequent binding target, allowing the non-target protein to be removed by washing during a subsequent step of binding to a biological target.

In various embodiments, a suitable dye is highly water-soluble by possessing water soluble groups, such as sulfonate group and/or a water-soluble polymer as defined herein. While not wishing to be bound by theory, it is believed that the labeling method can tolerate up to 4 to 5 times of a non-target protein (relative to the amount of target protein) as described herein. In various embodiments, up to 10 fold non-target protein may be present without sacrificing the performance of the labeled target protein. In general, labeling comprises linking a dye to a target protein by way of covalent interactions. In some embodiments, labeling comprises formation of a covalent bond, such as an amide bond.

In some embodiments, the amount of target protein in a sample solution is between about 0.1 µg-10000 µg, such as between 1 µg-1000 µg, 5 µg-200 µg, 5 µg-20 µg, 20 µg-50 µg, or 50 µg-100 µg. In some embodiments, the amount of target protein in a sample is about, less than about, or more than about 0.001, 0.01, 0.1, 1, 2, 3, 4, 5, 6, 7, 8, 9, 10, 15, 20, 25, 50, 100, 150, 200, 250, 500, 1000, 1500, 2000, 3000, 4000, 5000, 6000, 7000, 8000, 9000, 10000, or more micrograms (µg). In some embodiments, m1 and m2 (both in lag) define the lower and upper limits of an amount of target protein in a sample labeling reaction. In some embodiments, the relationship between m1 and m2 for a target protein to be labeled by a specified amount of reactive dye is expressed as m2/m1, where m2/m1 has a specified value or range of values. In some embodiments, m1 is from about 0.1 µg to about 500 µg, and m2/m1 is from about 1 to about 20. In some embodiments, m1 is from about 1 µg to about 200 µg, and m2/m1 is from about 2 to about 5. In some embodiments, m1 is from about 5 µg to about 50 µg, and m2/m1 is from about 2 to about 4. In some embodiment, m1 is about 5 µg and m2/m1 is about 4. In some embodiment, m1 is about 20 µg and m2/m1 is about 2.5. In some embodiment, m1 is about 50 µg and m2/m1 is about 2.

In some embodiments, the target protein is dissolved in a sample buffer. A target protein dissolved in a sample buffer may have any concentration suitable for a labeling reaction, such as about, less than about, or more than about 0.001, 0.01, 0.1, 1, 2, 3, 4, 5, 6, 7, 8, 9, 10, 20, 30, 40, 50, or more mg/mL, or any range therebetween, such as from about 0.01-10 mg/mL, 0.1-5 mg/mL, or 0.5-1 mg/mL. A buffer for dissolving a target protein, such as an antibody, may be any of a number of commonly used biological buffers, including but not limited to phosphate buffered saline (PBS), Tris, MOPS, HEPES, and combinations thereof. In some embodiments, the concentration of Tris is less than about 1000 mM, 100 mM, 50 mM, 40 mM, 30 mM, 20 mM, 10 mM, 5 mM, or less.

In some embodiments, a sample solution comprising a target protein also comprises an amount of one or more stabilizers and/or one or more preservatives. Common stabilizers include, but are not limited to, bovine serum albumin (BSA), gelatin and glycerol. In some embodiments, the amount of BSA or gelatin is about, more than about, or less than about 50-fold, 40-fold, 30-fold, 20-fold, 10-fold, 9-fold, 8-fold, 7-fold, 6-fold, 5-fold, 4-fold, 3-fold, 2-fold, 1-fold, or less than the amount of the target protein by weight. In some embodiments, the amount of glycerol is about, more than about, or less than about 50%, 25%, 20%, 15%, 10%, 5%, 4%, 3%, 2%, 1% or less of the buffer. Common preservatives include, but are not limited to, sodium azide, thimerosal, and other antimicrobial agents. A sample solution may or may not be pretreated to purify a target protein away from one or more other sample solution components. In some embodiments, the sample solution is not pretreated to purify the target protein away from one or more other components of the sample solution. Methods for removing one or more excess sample solution components, such as preservatives and/or stabilizers, are known in the art, non-limiting examples of which include protein A-based affinity chromatography, size-exclusion chromatography, and ultra membrane filtration. Commercial kits for protein purification, such as antibody cleaning kits, may also be used for removing one or more excess sample solution components. Size-exclusion column chromatography and ultra membrane filtration are useful for removing stabilizers/preservatives of relatively small molecules, such as glycerol, Tris, and amino acids. Ultra membrane filtration may also be used to adjust target protein concentration to a desired value. Ultra membrane filtration can be conveniently and rapidly carried out on a centrifuge using a commercial ultra membrane filtration vial. The membranes in such ultra filtration devices typically have different pore sizes, or so-called Molecular Weight Cut-off sizes (MWCO), permitting relatively small molecules to go through while retaining bigger molecules, such as proteins. In some embodiments, a membrane with a MWCO of about, less than about, or more than about 1, 5, 10, 15, 20, 25, 50, 100, or more kD is used to purify a target protein before labeling. Purification methods may be used to purify labeled protein.

In some embodiments, the labeling reaction with a dye, detectable label or crosslinker takes place at temperature of about, less than about, or more than about 4° C., 10° C., 15° C., 16° C., 17° C., 18° C., 19° C., 20° C., 21° C., 22° C., 23° C., 24° C., 25° C., 26° C., 27° C., 28° C., 29° C., 30° C., 37° C., 40° C., 50° C., or higher. In some embodiments, the labeling reaction takes place a room temperature, such as between 15° C.-30° C. In some embodiments, the labeling reaction is completed in less than about 5, 4, 3, 2, 1, or fewer hours; or less than about 60, 45, 30, 25, 20, 15, 10, 9, 8, 7, 6, 5, or fewer minutes. In some embodiments a completed labeling reaction containing a target protein labeled with a detectable label such as a dye, is used, such as in a detection process, without further manipulation, such as without the addition of other reagents, such as a quenching agent, and/or without purification, isolation, or concentration of the labeled target protein. Likewise, in some embodiments, a completed labeling reaction containing a target protein labeled with a crosslinker can be used directly in a subsequent protein-protein conjugation reaction without any purification of the crosslinker-labeled target protein as described herein.

A second reaction buffer used in the protein-protein conjugation method of the invention can be any buffer that facilitates the reaction between the hydrolysis-resistant functional group of the crosslinker and the pairing hydrolysis-resistant reactive group on the reporter protein described further in details below. In some embodiments, the second buffer comprises a catalyst that can accelerate the conjugation reaction. Similar to the reaction buffer used in detectable label-target protein conjugation or the first reaction buffer used in conjugating the crosslinker to the target protein, in some embodiments the second reaction buffer is provided as a concentrated solution that is about, more than about, or less than about 2-fold, 5-fold, 10-fold, 20-fold, 30-fold, 40-fold, 50-fold, or more than the concentration of the buffer in the second combined solution. In some embodiments, the second buffer is a buffer that facilities an oxime or hydrazone bond formation, such as the reaction between an aldehyde functional group and an aminooxy or hydrazino reactive group. Oxime and hydrazone formation generally prefers a relatively acidic buffer, such as a buffer with a pH from about 3 to about 7. Generally, aryl amines, such as aniline, are known to catalyze oxime and hydrazone formation. Thus, according to one embodiment, the second buffer is a phosphate buffer with a pH between about 3 and about 4, further comprising between about 1 and about 1000, or about 10 and about 200, or about 50 and about 150, or about 75 and about 125 mM aniline. In some embodiments, the second buffer comprises between about 95 and 105 mM aniline, for example about 100 mM aniline.

A reporter protein suitable for the protein-protein conjugation method is generally a protein that can produce a detectable signal either by itself or upon interaction with another molecule. According to one embodiment, reporter proteins are enzymes that upon interaction with a colorogenic or fluorogenic enzyme substrate produce a colored or fluorescent product. For example, horseradish peroxidase (HRP) and alkaline phosphatase (AP) both are commonly used as reporter proteins that interact with a substrate to produce a detectable colored or fluorescent product. Some enzyme reporter proteins can also interact with a substrate to produce detectable luminescence or bioluminescence. According to one embodiment, reporter proteins are fluorescent proteins, which are natural or recombinant protein molecules that bear one or more fluorophores. According to one preferred embodiment, fluorescent proteins are phycobiliproteins. Phycobiliproteins are a family of fluorescent proteins found in cyanobacteria and eukaryotic red algae. In nature, these highly colored proteins function as light-harvesting antenna molecules to collect photo energy for biochemical synthesis. Phycobiliproteins are considered to be the brightest fluorescent dyes due to their large extinction coefficient (700,000-2,410,000) and high fluorescence quantum yield (0.68-0.98). As a result, phycobiliproteins are widely used as fluorescent labels for biological detection, offering sensitivity many times higher than small synthetic dyes. Phycobiliprotein-labeled probes are extensively used in bead-based detection, microarrays and flow cytometry. In some preferred embodiments, phycobiliproteins are R-phycerythrine (R-PE), allophycocianin (APC) and Peridinin-chlorophyll-protein (PerCP). R-PE and PerCP are both excitable by the common 488 nm argon laser, but emit at ~578 nm and ~675 nm, respectively. APC, on the other hand, is excitable by the red He—Ne laser with emission at ~660 nm. The variety of emission wavelengths by phycobiliproteins can be further extended by the use of so-called tandem dyes. Tandem dyes are energy transfer dyes prepared by covalently labeling phycobiliproteins with a suitable synthetic dye that acts as energy receptor. In a tandem dye, the phycobiliprotein acts an antenna dye to efficiently absorb excitation light and then transfer its emission energy to the acceptor synthetic dye, which re-emits at the emission wavelength of the acceptor dye. By using appropriate acceptor dyes, the original emission wavelengths of phycobiliproteins can be extended to virtually anywhere between about 580 nm and 800 nm. Thus, by using a combination of regular synthetic dyes, phycobiliproteins and tandem dyes, it is possible for one to detect many biological targets in the same sample by using only a limited number of excitation sources. For example, by using a combination of dyes, it is possible to detect over 10 targets in the same sample by flow cytometry.

In some embodiments of the methods of the invention, the reporter proteins are pre-functionalized with a hydrolysis-resistant reactive group capable of reacting with the hydrolysis-resistant functional group of the crosslinker-modified target protein to form a covalent linkage. The pre-functionalized reporter protein is usually purified such that it is substantially free of any unattached small molecule comprising the same reactive group that may interfere with the protein-protein conjugation reaction. The pre-functionalized reporter protein may be prepared by reacting any of the above mentioned reporter protein with a crosslinker comprising a first reactive group capable of reacting with an amine or thiol on the reporter protein to form a covalent linkage and a second hydrolysis-resistant reactive group capable of reacting with the functional group on the crosslinker-modified target protein. The functionalization reaction of the reporter protein may be carried out in any of the buffers mentioned previously herein. The functionalized reporter protein may be purified by size exclusion column, ultramembrane filtration or dialysis to remove any unattached crosslinker. In some cases, the hydrolysis-resistant reactive group may not be a pairing reactive group to the hydrolysis-resistant functional group on the crosslinker-modified target protein; that is, the initial hydrolysis-resistant reactive group on the reporter protein may not react with the hydrolysis-resistant functional group on the target protein. In such a case, the initially functionalized reporter protein is usually reacted with a second crosslinker which, upon reacting with the initially functionalized reporter protein, provides a suitable hydrolysis-resistant reactive group for conjugation to the target protein.

According to one embodiment, the invention provides a reporter protein prefunctionalized with an aminooxy or hydrazino group, wherein the reporter protein comprises 1 to about 15 aminooxy or hydrazino groups and the wherein the functionalized reporter protein is purified to remove unreacted aminooxy or hydrazino crosslinker. The aminooxy or hydrazino groups herein are usually "free" reactive group, i.e. they are not in a protected form, such as aminooxy or hydrazino groups protected by acetone in the form of an oxime or hydrazone. Free aminooxy or hydrazino groups possess much higher reactivity toward aldehyde or ketone groups in conjugation reaction than their protected forms. In one embodiment, the reporter protein comprises 1 to about 6 aminooxy or hydrazino groups. According to some embodiments, the pre-functionalized reporter proteins are aminooxy-functionalized reporter proteins selected from the list consisting of phycobiliproteins, tandem dyes, horseradish peroxidase and alkaline phosphatase. In some embodiments, the functionalized reporter protein may be provided as lyophilized solid or as a solution.

Provided herein is also a method of preparing an aminooxy- or hydrazino-functionalized reporter protein, comprising the steps of: (a) reacting a reporter protein with a bifunctional crosslinker comprising an amine-reactive group and an aldehyde or ketone group in a buffer for a time sufficient to form an aldehyde or ketone functionalized reporter protein; (b) reacting the aldehyde- or ketone-functionalized reporter protein with an excess of a bis-aminooxy, a bis-hydrazino or a aminooxy-hydrazino crosslinker in a buffer for a time sufficient to form an aminooxy- or hydrazino-functionalized reporter protein; and (c) purifying said functionalized reporter protein.

The conjugation of a reporter protein to the crosslinker-modified target protein can be carried out at any temperature from above 0° C. to about 90° C., depending on the stability of the protein. More typically, the reaction is carried out from about 4° C. to about 45° C. In some embodiments, the reaction is carried out at room temperature, such as from about 15° C. to about 30° C. The reaction time may be longer than that for functionalizing the target protein with the crosslinker because of the relatively large size of the two proteins. When the reaction is carried out at room temperature, the reaction time may be greater than 15 minutes, or greater than 30 minutes. In some embodiments, the reaction time is about 1 hour at room temperature. In some embodiments a completed labeling reaction containing a target protein labeled with a reporter protein is used, such as in a detection process, without further manipulation, such as without the addition of other reagents, such as a quenching agent, and/or without purification, isolation, or concentration of the labeled target protein.

In some embodiments, one or more portions of an amount of labeled protein produced by the labeling reaction are used directly in one or more processes, and unused labeled protein is stored for later use. In some embodiments, a storage buffer is added to a labeled protein to produce a stored protein solution. In general, a storage buffer is effective in increasing the time following a labeling reaction during which a labeled protein remains stable. In general, a labeled protein is considered "stable" when it retains its activity, or a substantial portion thereof, such as for use in a detection process. In some embodiments, a stored protein is considered stable when about or more than about 30%, 40%, 50%, 60%, 70%, 80%, 85%, 90%, 95%, 97.5%, 99%, 99.5%, 99.9%, or more of the pre-storage activity remains. In some embodiments, the stored labeled protein is stable for about or more than about 1, 2, 3, 4, 5, 6, 7, 8, or more weeks; 1, 2, 3, 4, 5, 6, 7, 8, 9, 10, 11, 12, or more months; or 1, 2, 3, or more years. In some embodiments, a storage buffer comprises one or more stabilizers and/or one or more preservatives. Non-limiting examples of stabilizers include bovine serum albumin, gelatin, and glycerol. Non-limiting examples of preservatives include sodium azide, thimerosal, and other antimicrobial agents. In general, a storage buffer can have either a lower pH or higher pH than the buffer used in the labeling reaction, such that addition of the storage buffer lowers or raises the pH of the combined solution containing the labeled protein. In some embodiments, the pH of a solution containing a stored, labeled protein is about, less than about, or more than about 5.5, 6, 6.5, 7, 7.1, 7.2, 7.3, 7.4, 7.5, 7.6, 7.7, 7.8, 7.9, 8, 8.5, 9, or higher. In some embodiments, the pH of the stored protein solution is between about 6.0-9.0, such as 6.5-8.0, or 7.2-7.5.

Labeled proteins of the present invention can be used as indicators of the presence, absence, relative abundance, and/or amount of a biological target, such as may be found in a biological sample or organism, for example by use in a detection process. In one aspect, the invention provides a method for staining one or more biological targets. In one embodiment, the method comprises (a) preparing one or more labeled proteins according to a method of the present invention, wherein each of said one or more labeled proteins comprises a targeting moiety that binds to a binding partner associated with one or more of said biological targets; and, (b) exposing said one or more biological targets to said one or more labeled proteins, such that said labeled protein binds to said binding partner thereby staining said one or more biological targets. In some embodiments, step (b) is performed without purification of the one or more labeled proteins. In some embodiments, step (a) is not terminated by the addition of a quencher.

In general, a biological sample refers to any biological tissue or fluid. In some embodiments, samples include, but are not limited to, cells in culture, bone marrow; blood; blood cells (e.g., white blood cells, red blood cells, etc.); ascites; tissue or fine needle biopsy samples; cell-containing body fluids; free floating nucleic acids; sputum; urine; cerebrospinal fluid, peritoneal fluid; pleural fluid; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom. In some embodiments, a sample comprises cells obtained from a patient. The cells may be, for example, from blood, bone marrow, and/or from tissue derived from solid organs, such as brain, spleen, bone, heart, vascular, lung, kidney, liver, pituitary, endocrine glands, lymph node, dispersed primary cells, tumor cells. Biological samples may include sections of tissues, including but not limited to frozen or fixed sections taken for histological purposes. In some embodiments, a sample may be a body fluid, including, but not limited to, blood fluids, lymph, ascitic fluids, gynecological fluids, and urine. Samples may be obtained from a subject by any of a wide variety of methods known in the art, including without limitation biopsy (e.g., fine needle aspiration or tissue biopsy), surgery, and collection of body fluid (e.g., blood, lymph, etc.). Biological samples also include any material derived by processing any of the above samples. Derived samples may, for example, include nucleic acids or proteins extracted from the biological sample, or obtained by subjecting the sample to techniques such as amplification or reverse transcription of mRNA, or isolation and/or purification of certain components.

A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr–/–, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN- 5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, staining of the one or more biological target is performed in vivo or in vitro. Many methods for staining or otherwise detecting a biological target using binding partners are known in the art, and include without limitation immunohistochemistry, immunosorbent assays (e.g. ELISA, with or without a linked enzyme), flow cytometry, fluorescence activated cell sorting (FACS), microarray (e.g. protein array), and other binding partner assays whereby the presence of a binding partner is indicated by retention by an organism, sample, or portion thereof of the one or more labeled protein (e.g. Western blot). In some embodiments, the label carried by the labeled protein is directly observable, such as in a fluorescent dye detectable by exposure to light of a particular frequency or range of frequencies. Typically, excess labeled protein is washed away prior to detection, such that labeled protein that remains is indicative of the presence, absence, relative abundance, and/or quantity of the biological target. Examples of biological targets include, but are not limited to, amino acids, polypeptides, nucleotides, polynucleotides (e.g. DNA or RNA), carbohydrates, lipids, metabolites, cell signaling molecules, cluster of differentiation proteins, hormones, cell surface proteins, intracellular proteins, fragments thereof, and combinations or complexes thereof. In some embodiments, two or more different labeled proteins, each recognizing a different binding partner or set of binding partners are used to detect two or more different biological targets in a single sample or organism. The different labeled proteins typically comprise different targeting moieties, and may or may not comprise the same dye. In some embodiments, each of two or more different labeled proteins are labeled with different dyes, such that exposing two or more biological targets to the two or more differently labeled proteins renders the two or more biological targets optically distinguishable. In some embodiments, one or more biological targets are exposed to a primary binding agent, such as an antibody, that is unlabeled, before exposure to a labeled protein that specifically binds the primary binding agent.

In some embodiments, stained biological targets are analyzed by flow cytometry. Methods and devices for carrying out flow cytometry on cells and other particles are known in the art. Flow cytometry is a technique for counting, examining, and/or sorting microscopic particles suspended in a stream of fluid. It allows simultaneous multiparametric analysis of the physical and/or chemical characteristics of single cells flowing through an optical/electronic detection apparatus. A description of a typical flow cytometry process follows. One or more beams of light, usually laser light, of one or more frequencies are directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors. Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness. Subsequent to detection, cells may be routed to a receptacle based on one or more characteristics measured by said detection so as to sort and physically group cells based on such characteristics, such as in fluorescence activated cell sorting (FACS). Each of a plurality of receptacles may be designated to contain a different set of cells, each set having a different characteristic or set of characteristics. Receptacles can be any suitable container, including but not limited to wells of a multi-well plate; tubes; and ordered tubes, such as in a rack or an array.

In some embodiments, stained biological targets are analyzed by western blot. Methods and systems for carrying out Western blots are known in the art. Briefly, this method involves separation of a substrate from other protein by means of a separation medium, such as an acrylamide gel, followed by transfer of the substrate to a membrane (e.g., nylon or PVDF). Presence of the substrate is then detected by labeled binding partners specific for the substrate, such as antibodies, which may in turn be detected by a further binding reagent. Where this first binding partner is a labeled protein, use of further binding reagents may not be necessary. This method enables both quantitation of an amount of substrate and determination of its identity by a relative position on the membrane which is indicative of a migration distance in the separation medium (e.g. during electrophoresis).

In some embodiments, stained biological targets are analyzed by immunohistochemistry. Methods and systems for immunohistochemical analysis are known in the art. In general, detections involving cells include sample fixation and permeabilization, sample blocking with a blocking solution, incubation of the sample with one or more labeled primary binding agents, washing of the stained sample, and detection. Typically, sections of a tissue sample are adhered to a microscope slide. The sample is then exposed to one or more binding agents, each with specificity for one or more targets. Where the one or more binding agents comprise a detectable label, such as a dye, staining is evaluated by detecting the detectable label. Where the one or more binding agents do not comprises a detectable label, the sample are exposed to one or more second binding agents, each with specificity to one or more of the first binding agents and comprising a detectable label, such as a dye. In some embodiments, stained samples are analyzed under a microscope. The combination of exposure to unlabeled binding agent followed by exposure to a second, labeled binding agent can be used in combination with any detection process, for example to amplify a signal.

In some embodiments, the method further comprises visualizing fluorescence of the stained one or more biological targets. Visualization may be by eye, or may be performed by a device, such as a camera, whereby an image is produced. Typically, visualization is performed after a washing step to remove excess labeled protein. In some embodiments, visualization is performed immediately after washing. In some embodiments, visualization is performed at about, before about, or after about 1, 5, 10, 15, 20, 30, 45, 60, 90, 180, or more minutes after washing; 1, 2, 3, 4, 5, 6, 7, 8, 9, 10, 15, 20, 24, or more hours after washing; or 1, 2, 3, 4, 5, 6, 7, 8, 9, 10, 15, 20, 25, 30, 60, or more days after washing. In some embodiments, a biological samples stained by the methods of the invention are stored for later visualization. In general, visualization involves detecting the presence and optionally level of one or more dyes used to stain one or more biological targets in a biological sample, which in turn is indicative of the presence and optionally level of the one or more biological targets in a biological sample. Where the dye is fluorescent dye, visualization may comprise exposure to an excitation frequency, following by detecting frequency and/or intensity of fluorescent light emitted by one or more dyes used to stain a biological sample. In general, the wavelength of excitation for a given dye is shorter than the wavelength emitted by the dye. In some embodiments, the excitation wavelength is about, less than about, or more than about 250 nm, 300 nm, 350 nm, 400 nm, 450 nm, 500 nm, 550 nm, 560 nm, 570 nm, 580 nm, 590 nm, 600 nm, 610 nm, 615, 620 nm, 625, 630 nm, 635, 640 nm, 645, 650 nm, 655, 660 nm, 665, 670 nm, 675, 680 nm, 685, 690 nm, 695, 700 nm, 705, 710 nm, 715, 720 nm, 725, 730 nm, 735, 740 nm, 745, 750 nm, 755, 760 nm, 765, 770 nm, 775, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1020 nm, 1040 nm, 1060 nm, 1080 nm, 1100 nm, 1120 nm, 1140 nm, 1160 nm, 1180 nm, 1200 nm, or any range including two such wavelengths as endpoints, such as from about 350 nm to about 1200 nm, and from about 450 nm to about 750 nm. In some embodiments, the emission wavelength is about, less than about, or more than about 250 nm, 300 nm, 350 nm, 400 nm, 450 nm, 500 nm, 550 nm, 560 nm, 570 nm, 580 nm, 590 nm, 600 nm, 610 nm, 615, 620 nm, 625, 630 nm, 635, 640 nm, 645, 650 nm, 655, 660 nm, 665, 670 nm, 675, 680 nm, 685, 690 nm, 695, 700 nm, 705, 710 nm, 715, 720 nm, 725, 730 nm, 735, 740 nm, 745, 750 nm, 755, 760 nm, 765, 770 nm, 775, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1020 nm, 1040 nm, 1060 nm, 1080 nm, 1100 nm, 1120 nm, 1140 nm, 1160 nm, 1180 nm, 1200 nm, 1220 nm, 1240 nm, 1250 nm, or any range including two such wavelengths as endpoints, such as from about 360 nm to about 1250 nm.

In some embodiments, a diagnosis of a condition in a subject is made based on the results of the staining process. Conditions that may be diagnosed according to these methods include any that are associated with a detectable marker or characteristic that can be detected by exposure to a labeled protein of the present invention. For example, a large number of antibodies against various disease targets, including but not limited to tumor-associated antigens, have been deposited at the American Type Culture Collection (ATCC) and/or have published variable region sequences and are available for use in the claimed methods and compositions. Antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Examples of diseases and conditions that may be identified using the methods and compositions of the invention include, but are not limited to, inherited diseases, infectious diseases, diseases arising from genetic mutation, poisoning, and cancer.

In one aspect, the invention provides a method for evaluating the efficacy of a test compound. In one embodiment, the method comprises (a) exposing a system comprising a drug target to a test compound; (b) staining one or more biological targets in said system according to a method of the invention; and evaluating the efficacy of said test compound based on the results of step (b). The drug target and the biological target may be the same or different. In general, efficacy is measured by comparing the degree of an effect in a system receiving the test compound with the degree of an effect in a system receiving no compound or a reference compound. In general, an effect is measured by detecting the stained biological target, such as by visualizing a fluorescent dye. Examples of effects on biological targets as may be detected using a labeled protein of the invention include, but are not limited to, changes in absolute abundance, changes in relative abundance, changes in localization (such as within a cell, within a tissue, within an organ, or within an organ system), and any effect that can be observed or quantified by visualizing the labeled protein. Systems that can be exposed to a drug target include in vitro systems and in vivo systems, such as reactions in solution, cultured cells, and whole organisms. Staining may be performed on the system itself, or on a sample therefrom. For example, a test compound may be delivered to a subject, such as a human, and an effect on a tissue of the subject may be evaluated in a sample of the tissue removed from the subject by staining the sample according to the methods of the invention.

Examples of test compounds include, but are not limited to, drugs, small molecules, activators, inhibitors, antitumor agents, anti-miotics, steroids, sympathomimetics, local anesthetics, antimicrobial agents, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, respiratory agents, non-steroidal hormones, antihormones, vitamins, herb medicines, antimuscarinic, muscarinic cholinergic blocking agents, mydriatics, psychic energizers, humoral agents, antispasmodics, antidepressant drugs, anti-diabetics, anorectic drugs, anti-allergenics, decongestants, antipyretics, antimigrane, anti-malarials, anti-ulcerative, peptides, anti-estrogen, anti-hormone agents, antiulcer agents, anesthetic agent, drugs having an action on the central nervous system, growth factors, mitogens, cytokines, adhesion molecules, hormones, polynucleotides, antibodies, natural compounds, lactones, chemotherapeutic agents, immune modulators, carbohydrates, proteases, ions, reactive oxygen species, protein fragments, or combinations thereof. In some embodiments, a physical parameter is used to modulate the system instead of a test compound having a drug target. Examples of physical parameters include, but are not limited to radiation, heat, cold, UV radiation, changes in pressure, and combinations thereof.

The test compounds may be found and/or isolated from a variety of custom and commercially available combinatorial libraries. In one embodiment, the pool of test compounds may include libraries of antitumor agents such as, chemotherapeutic agent is selected from the group consisting of adriamycin, 5-fluorouracil (5FU), etoposide (VP-16), camptothecin, actinomycin-D, mitomycin C, cisplatin (CDDP), doxorubicin, etoposide, verapamil, podophyllotoxin, carboplatin, procarbazine, mechlorethamine, cyclophosphamide, ifosfamide, melphalan, chlorambucil, bisulfan, nitrosurea, dactinomycin, daunorubicin, bleomycin, plicomycin, mitomycin, tamoxifen, taxol, transplatinum, vincristin, vinblastin, methotrexate, pilocarpine, mixtures and combinations thereof and the like.

Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like. Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β 2-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE 1, PGE 2 α, and PGF 2 α, and the PGE 1 analog misoprostol. Antispasmodics such as, atropine, methantheline, papavenne, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenytoin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like. Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like. Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like. Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and the like and anticancer drugs such as, tamoxifen, methotrexate, and the like. Anorectic drugs such as, dextroamphetamine, methamphetamine, phenylpropanolamine, fenfluramine, diethylpropion, mazindol, phentermine, and the like. Anti-malarials such as, the 4-aminoquinolines, alphaaminoquinolines, chloroquine, pyrimethamine, and the like. Anti-ulcerative agents such as, misoprostol, omeprazole, enprostil, and the like. Antiulcer agents such as, allantoin, aldioxa, alcloxa, N-methylscopolamine methylsuflate, and the like. The drugs mentioned above may be used in combination as required. Moreover, the above drugs may be used either in the free form or, if capable of forming salts, in the form of a salt with a suitable acid or base. If the drugs have a carboxyl group, their esters may be employed.

In general, a biological target is any target comprising a binding partner to which a labeled protein of the current invention specifically binds. The methods and compositions of the invention may be employed to examine and profile the status of any biological target in a cellular pathway, or collections of such biological targets. Single or multiple distinct pathways may be profiled (sequentially or simultaneously), or subsets of biological targets within a single pathway or across multiple pathways may be examined (again, sequentially or simultaneously).

A wide variety of activation events can be detected by labeled proteins of the present invention. In general, the basic requirement is that the change in activation results in a change in the biological target that is detectable by altered binding to a labeled protein. What is important is to differentiate, using a labeled protein that specifically binds to a binding partner that is indicative of an activation state, thus distinguishing between two or more activation states (e.g. "off" and "on"). Typically, the binding partner is specific for an activation state of an activatable element.

The activation state of an individual activatable element is either in the on or off state. As an illustrative example, and without intending to be limited to any theory, an individual phosphorylatable site on a protein can activate or deactivate the protein. The terms "on" and "off," when applied to an activatable element that is a part of a biological target, are used here to describe the state of the activatable element, and not necessarily the overall state of the biological target of which it is a part. Typically, a cell possesses a plurality of a particular protein or other constituent with an activatable element and this plurality of proteins or constituents usually has some proteins or constituents whose individual activatable element is in the on state and other proteins or constituents whose individual activatable element is in the off state. Since the activation state of each activatable element is measured through the use of a labeled protein that recognizes a specific activation state, only those activatable elements in the specific activation state recognized by the binding element, representing some fraction of the total number of activatable elements, will be bound by the labeled protein to generate a measurable signal. The measurable signal corresponding to the summation of individual activatable elements of a particular type that are activated in a sample is the "activation level" for that activatable element in that sample. In some embodiments, activation level is measured at the level of single cells, such as a plurality of cells in a sample.

Activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations. In some embodiments, the basis for classifying cells is that the distribution of activation levels for one or more specific activatable elements will differ among different phenotypes. A certain activation level, or more typically a range of activation levels for one or more activatable elements seen in a cell or a population of cells, is indicative that that cell or population of cells belongs to a distinctive phenotype. Other measurements, such as cellular levels (e.g., expression levels) of biomolecules that may not contain activatable elements, may also be used to classify cells in addition to activation levels of activatable elements; it will be appreciated that these levels also will follow a distribution, similar to activatable elements. Thus, the activation level or levels of one or more activatable elements, optionally in conjunction with levels of one or more levels of biomolecules that may not contain activatable elements, of a cell or a population of cells may be used to classify a cell or a population of cells into a class. Once the activation level of intracellular activatable elements of individual single cells is known they can be placed into one or more classes, e.g., a class that corresponds to a phenotype. A class encompasses a class of cells wherein every cell has the same or substantially the same known activation level, or range of activation levels, of one or more intracellular activatable elements, or other binding partners detected by the labeled proteins of the invention. For example, if the activation levels of five intracellular activatable elements are analyzed, predefined classes that encompass one or more of the intracellular activatable elements can be constructed based on the activation level, or ranges of the activation levels, of each of these five elements. It is understood that activation levels can exist as a distribution and that an activation level of a particular element used to classify a cell may be a particular point on the distribution but more typically may be a portion of the distribution.

In addition to activation levels of intracellular activatable elements, expression levels of intracellular or extracellular binding partners can be used alone or in combination with activation states of activatable elements and/or expression levels to classify cells. In some embodiments, other characteristics that affect the status of a biological target may also be used to classify a cell. Examples include the translocation of binding partners or changes in their turnover rates and the formation and disassociation of complexes of comprising a binding partner. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a binding partner.

In some embodiments, the physiological status of one or more cells is determined by examining and profiling the activation level of one or more activatable elements in a cellular pathway. In some embodiments, a cell is classified according to the activation level of a plurality of activatable elements. In some embodiments, the activation level of one or more activatable elements in a samplei is correlated with a condition. In some embodiments, the activation level of one or more activatable elements in single cells within the sample is determined. Cellular constituents that may include activatable elements include without limitation, proteins, carbohydrates, lipids, nucleic acids and metabolites. Upon activation, a change occurs to the activatable element, such as covalent modification of the activatable element (e.g., binding of a molecule or group to the activatable element, including but not limited to, phosphorylation, acetylation, methylation, ubiquitination) or a conformational change. Such changes generally contribute to changes in particular biological, biochemical, or physical properties of the biological target that contains the activatable element. The state of the biological target that contains the activatable element is often determined to some degree, though not necessarily completely, by the state of activation of a particular activatable element of the biological target. For example, a complex may comprise a protein having multiple activation sites, and the particular activation states of these sites may overall determine the activation state of the protein and/or complex. Additional factors, such as the binding of other proteins, pH, ion concentration, interaction with other cellular constituents, and the like, can also affect the state of the biological target. In some embodiments, the activation levels of a plurality of intracellular activatable elements in single cells are determined. In some embodiments, at least about 2, 3, 4, 5, 6, 7, 8, 9, 10 or more than 10 intracellular activatable elements are determined.

Activation states of activatable elements may result from chemical additions or modifications of biomolecules and include biochemical processes such as glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator. In general, the activation level is determined by detecting binding of a labeled protein that is specific for either the modified activatable element or the unmodified activatable element, such as a labeled antibody specific to a protein phosphorylated at a particular site, which antibody does not specifically bind to the unphosphorylated protein.

Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis (e.g. PARP), cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation. Examples of activatable elements, activation states and methods of determining the activation level of activatable elements are described in US Publication Number 20060073474 entitled "Methods and compositions for detecting the activation state of multiple proteins in single cells" and U.S. Pat. No. 7,393,656 entitled "Methods and compositions for risk stratification" the content of which are incorporate here by reference.

In some embodiments, the binding partner is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3a, GSK3p, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon β, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, PARP, Bcl-2, Mcl-1, Bcl-XL, Bcl-w, Bcl-B, Al, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Spl, Egr-1, T-bet, β-catenin, HIFs, FOXOs, E2Fs, SRFs, TCFs, Egr-1, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In some embodiments, the classification of a cell according to activation level of an activatable element, e.g., in a cellular pathway comprises classifying the cell as a cell that is correlated with a clinical outcome. In some embodiments, the clinical outcome is the prognosis and/or diagnosis of a condition. In some embodiments, methods and compositions are provided for the classification of a cell according to the activation level of an activatable element, e.g., in a cellular pathway wherein the classification comprises classifying a cell as a cell that is correlated to a patient response to a treatment. In some embodiments, methods and compositions are provided for the classification of a cell according to the activation level of an activatable element, e.g., in a cellular pathway wherein the classification comprises selecting a method of treatment.

In one aspect, the invention provides kits containing any one or more of the elements disclosed in the above methods and compositions. In some embodiments, the kit comprises one or more elements for carrying out a method of the invention, the elements in one or more containers. In one embodiment, a kit for labeling a target protein with a dye or detectable label comprises a buffer comprising an amine; one or more reactive dye or detectable label for labeling one or more target proteins; a storage buffer; and instruction in one or more languages, for example in more than one language. The reactive dye or detectable label may be a reactive dye, a reactive biotin, a reactive digoxin or a reactive epitope. The dye can be any of the dyes described herein, including but not limited to an amine reactive dye. The buffer can be any of the buffers described herein, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. The amine can be any amine described herein, including but not limited to Tris. In some embodiments, the dye comprises one or more activated esters, one or more sulfonates, and/or one or more water-soluble polymers, as described herein. In some embodiments, the buffer and dye are sufficient in amount to permit labeling of 5 µg to 200 µg of a target protein, such as more than about 75%, 80%, 85%, 90%, 95%, 96%, 97%, 98%, 99%, 99.5%, or more of the target protein in a sample is labeled. The storage buffer can be any of the storage buffers described herein, and may comprise a stabilizer and/or a preservative as described herein.

In another aspect, a kit for conjugating a reporter protein to a target protein is provided, the kit comprising a first buffer comprising a first amine as described herein; a second buffer comprising an aryl amine; a bifunctional crosslinker comprising an amine-reactive group and a hydrolysis-resistant functional group; one or more reporter proteins functionalized with a pairing hydrolysis-resistant reactive group for labeling one or more target proteins; a storage buffer; and instruction in one ore more languages, for example in more than one language. In some embodiments, the bifunctional crosslinker comprises a succinimidyl ester and an aldehyde group, and the one or more reporter proteins are functionalized with aminooxy groups.

In some embodiments, the kit further comprises a separation device for purifying a target protein before labeling, and/or for purifying a labeled target protein. Methods for purifying protein are known in the art, non-limiting examples of which include protein A-based affinity chromatography, size-exclusion chromatography, and ultra membrane filtration. Commercial kits for protein purification, such as antibody cleaning kits, may also be used for target protein purification. Size-exclusion column chromatography and ultra membrane filtration are useful for removing stabilizers/preservatives of relatively small molecules, such as glycerol, Tris, and amino acids. Ultra membrane filtration may also be used to adjust target protein concentration to a desired value. Ultra membrane filtration can be conveniently and rapidly carried out on a centrifuge using a commercial ultra membrane filtration vial. The membranes in such ultra filtration devices typically have different pore sizes, or so-called Molecular Weight Cut-off sizes (MWCO), permitting relatively small molecules to go through while retaining bigger molecules, such as proteins. In some embodiments, a membrane with a MWCO of about, less than about, or more than about 1, 5, 10, 15, 20, 25, 50, 100, or more kD is provided to purify a target protein before and/or after labeling. Columns for size exclusion chromatography typically comprise particles or beads having pores of a particular MWCO. Particles larger than the MWCO pass through the column faster than particles at or below the MWCO. In some embodiments, a column with a MWCO of about, less than about, or more than about 1, 2, 10, 15, 20, 25, 50, 100, or more kD is provided to purify a target protein before and/or after labeling.

In some embodiments, the kit further comprises a stain stabilizing reagent for enhancing dye fluorescence, such as by enhancing fluorescent intensity or reducing a rate of decrease in fluorescent intensity. Stain stabilizing reagents are known in the art, non-limiting examples of which include EverBrite (Biotium), Vectashield (Vector Laboratories), and SlowFade Gold (Invitrogen). In some embodiments, fluorescent intensity of a dye in the presence of the stain stabilizing reagent is increased by at least about 10%, 20%, 30%, 40%, 50%, 60%, 70%, 80%, 90%, 100%, 150%, 200%, 300%, 400%, 500% or more above the intensity of the dye in the absence of the stain stabilizing reagent. In some embodiments, fluorescent intensity of a dye in the presence of the stain stabilizing reagent is maintained above a threshold level for a time that is at least about 0.5, 1, 2, 3, 4, 5, 6, 7, 8, 9, 10, 15, 20, 25, 30, 35, 40, 45, 50, 55, 60, or more minutes. In some embodiments, the threshold level is at least about 10%, 20%, 30%, 40%, 50%, 60%, 70%, 75%, 80%, 85%, 90%, 95%, 96%, 97%, 98%, 99%, 99.5%, or more of the starting fluorescent intensity.

Tables 1-4 provide examples of dyes useful in the methods, compositions, and kits of the present invention.

TABLE 1

| Compound No. | Structure* |
|---|---|
| 1 | H₂N-[coumarin]-C(O)-NH-CH(CH₂SO₃⁻)-C(O)-N-[piperidine]-CO₂H |

TABLE 1-continued

| Compound No. | Structure* |
|---|---|
| 2 | 6-chloro-7-hydroxycoumarin-3-carboxamide linked via NH to a CH(CH₂SO₃⁻) group, then C(=O) to a piperidine N, with piperidine 4-CO₂H |
| 3 | 6,8-disulfonato-pyrene with 1-O-(CH₂)₄-C(=O)-NH(CH₂CH₂O)₁₂CH₂CH₂CO₂H and additional SO₃⁻ |
| 4 | Sulforhodamine-type xanthene: H₂N- and =NH₂⁺ substituted xanthene with SO₃⁻ and SO₂-NH(CH₂CH₂O)₈CH₂CH₂CO₂H; 9-(2-carboxyphenyl) |
| 5 | Bis-tetramethyl-tetrahydroquinoline-fused xanthene (AlexaFluor-like) with two SO₃⁻ groups; 9-substituted with 2-(imidazol-1-yl) bearing N-(CH₂)₅-CO₂H |
| 6 | Same bis-tetramethyl-tetrahydroquinoline-fused xanthene with two SO₃⁻ groups; 9-substituted with N-methylimidazolium bearing N-(CH₂)₅-CO₂H |

TABLE 1-continued
| Compound No. | Structure* |
|---|---|
| 7 | 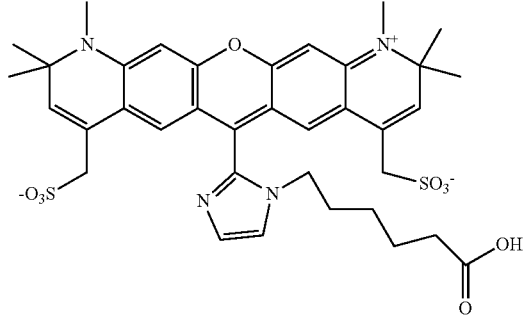 |
| 8 | 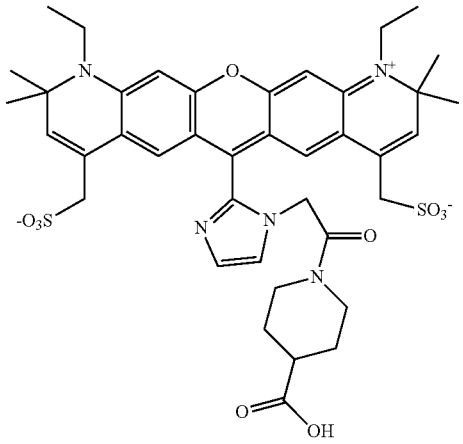 |
| 9 | 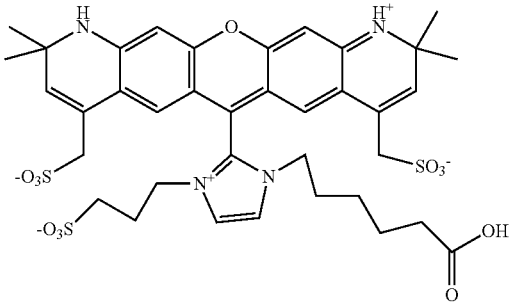 |
| 10 | 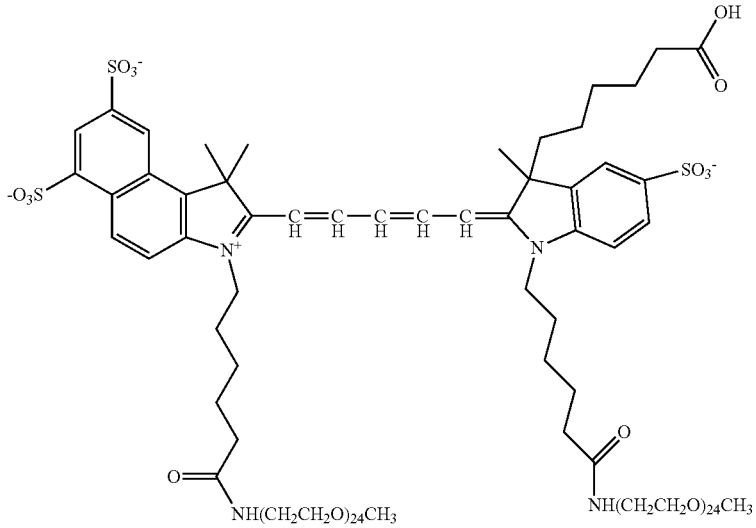 |

TABLE 1-continued

| Compound No. | Structure* |
|---|---|
| 11 | 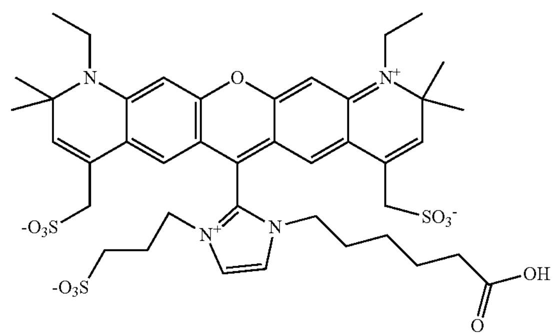 |
| 12 | 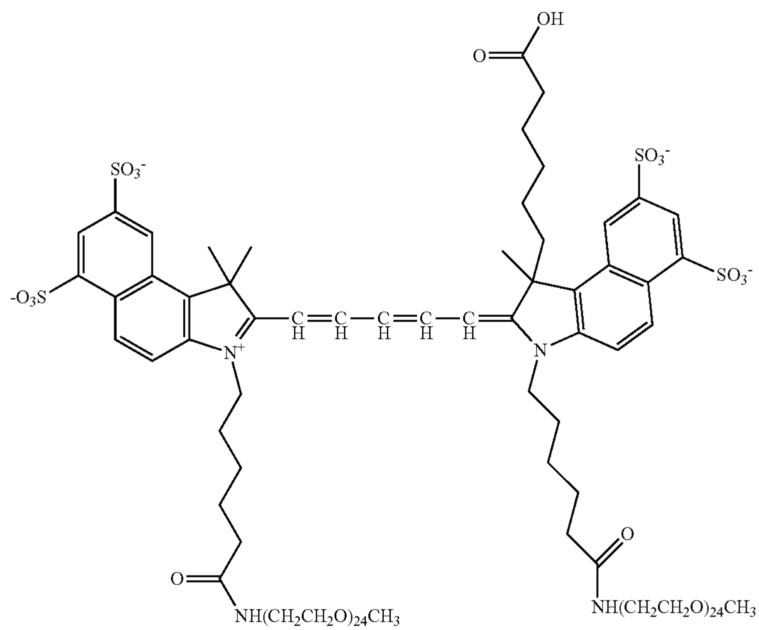 |
| 13 | 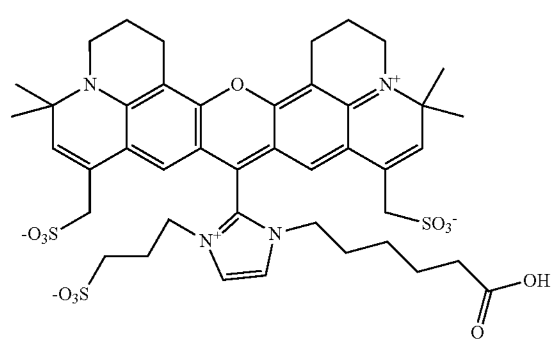 |

TABLE 1-continued

| Compound No. | Structure* |
|---|---|
| 14 | (chemical structure) |
| 15 | (chemical structure) |

TABLE 1-continued
| Compound No. | Structure* |
|---|---|
| 16 | 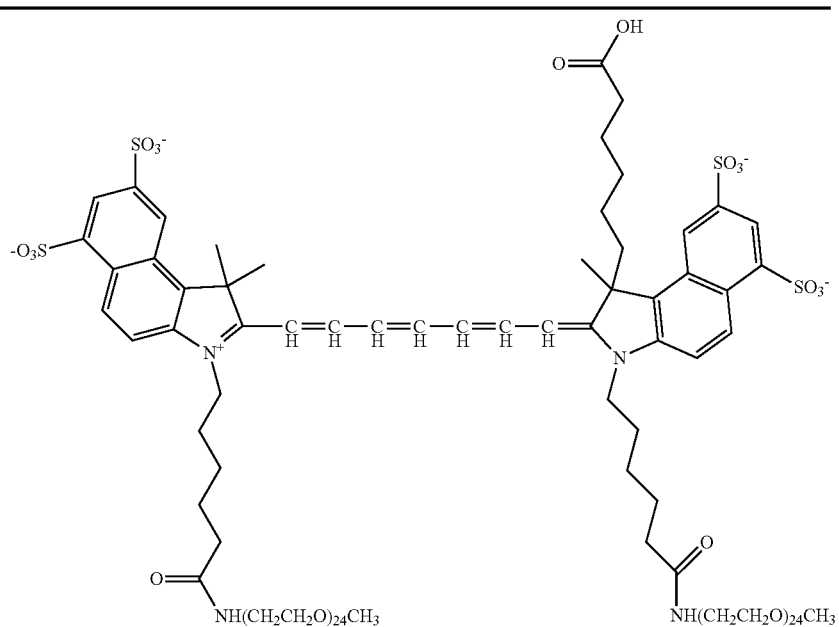 |
| 17 | 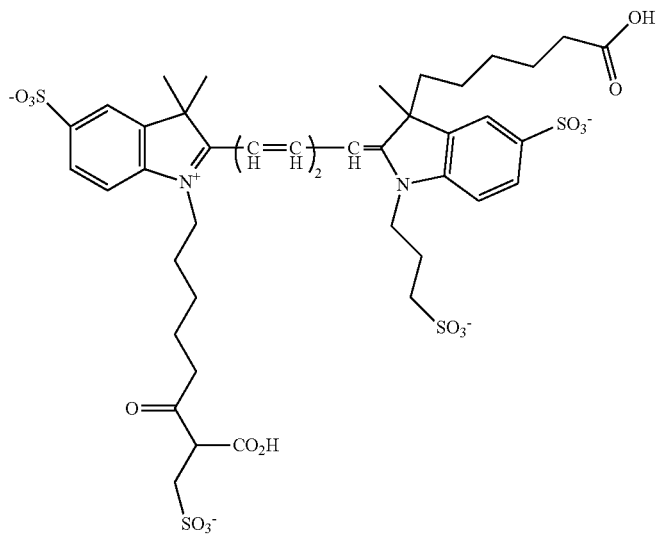 |

TABLE 1-continued

| Compound No. | Structure* |
|---|---|
| 18 | 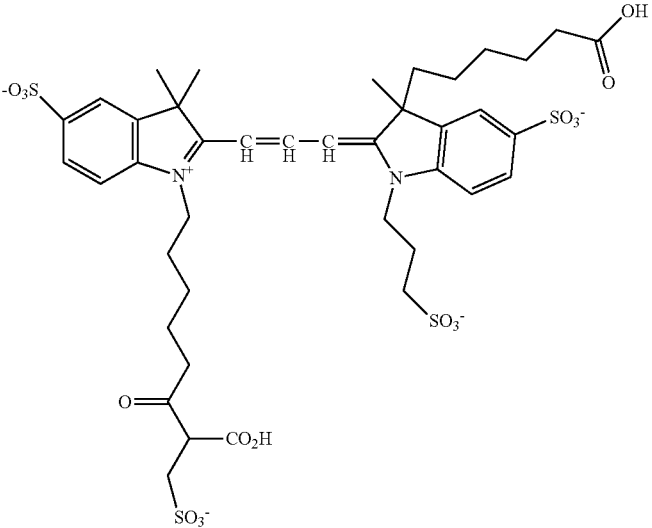 |

*Wherein when a dye comprise a carboxylic acid group, it is understood that the carboxylic acid group can be readily converted to an activated ester via the use of any of a number of reagents, such as DCC, EDC, and TSTU, so that the carboxylic acid group can react with amine group to form an amide linkage.

TABLE 2

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 19 | 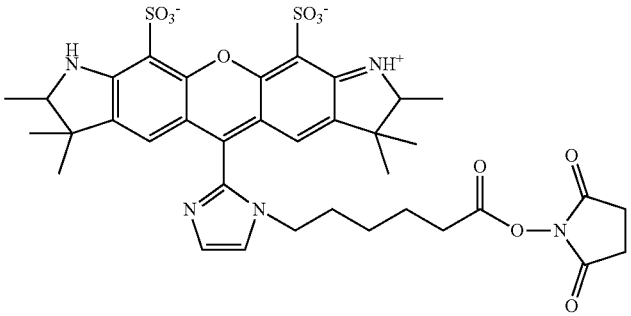 | 548/571 |
| 20 | 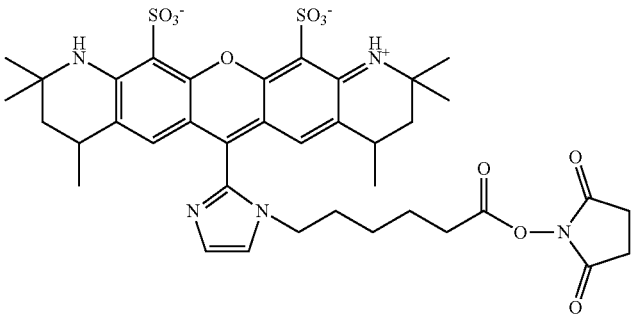 | 559/579 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 21 | 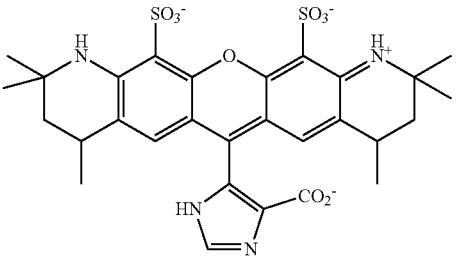 | 529/548 |
| 22 | 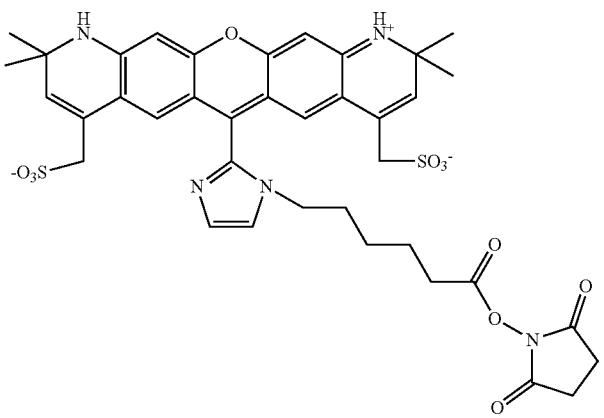 | 603/626 |
| 23 | 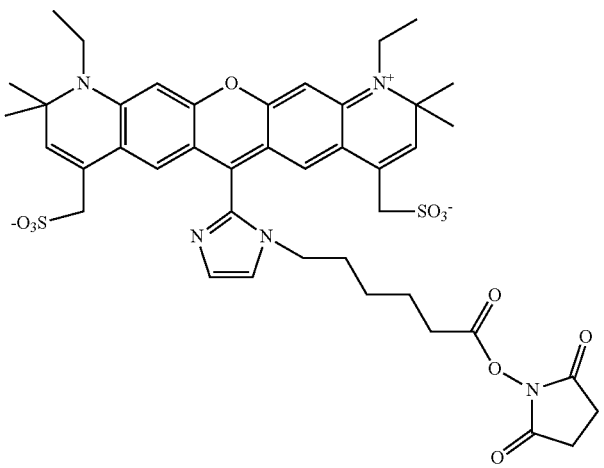 | 622/649 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/ Emission Wavelengths (nm) |
|---|---|---|
| 24 | 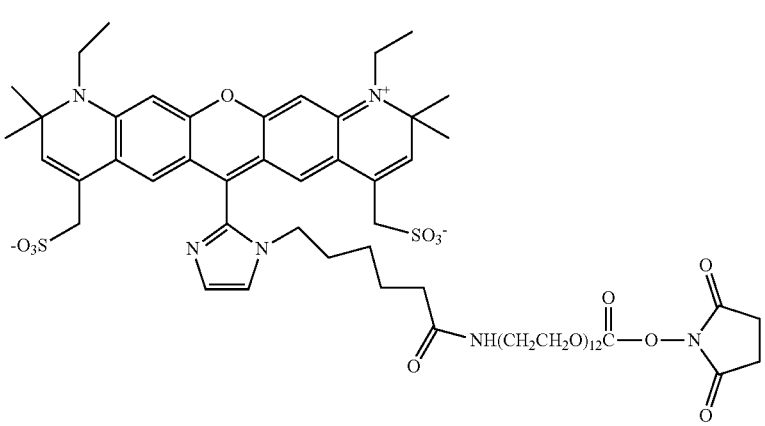 | 622/649 |
| 25 | 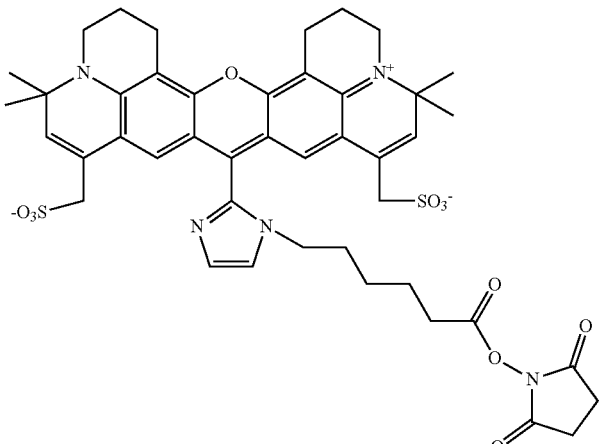 | 638/660 |
| 26 | 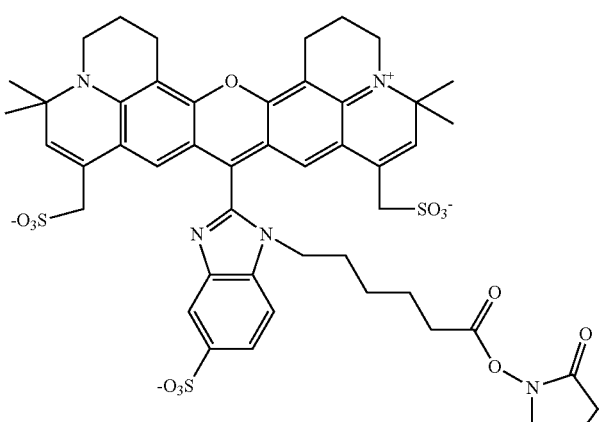 | — |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/ Emission Wavelengths (nm) |
|---|---|---|
| 27 | 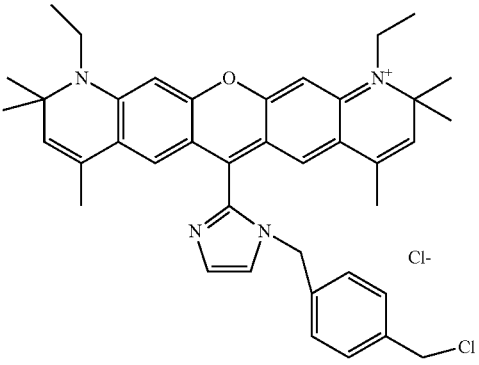 [SMILES: CCN1c2cc3c(cc2C(C)=CC1(C)C)C(c1nccn1Cc1ccc(CCl)cc1)=c1cc2c(cc1O3)=[N+](CC)C(C)(C)C=C2C ; [Cl-]] | 622/648 |
| 28 | 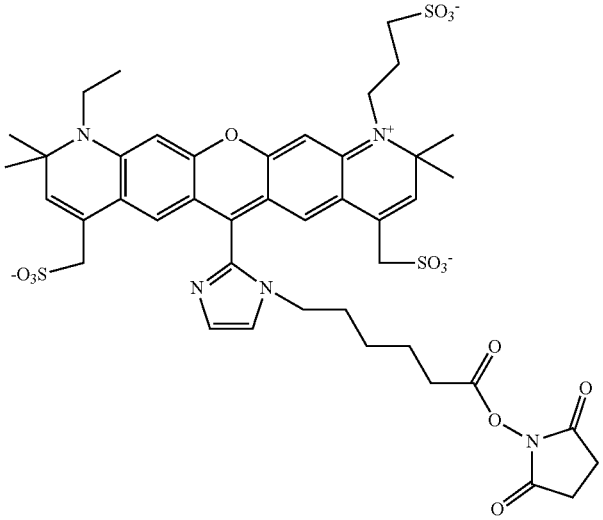 | 622/649 |
| 29 | 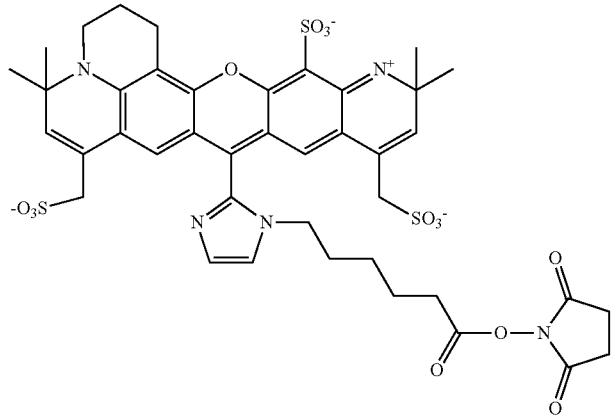 | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 30 | 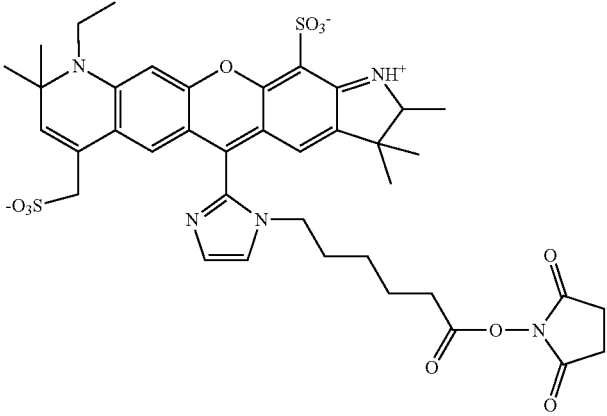 | |
| 31 | 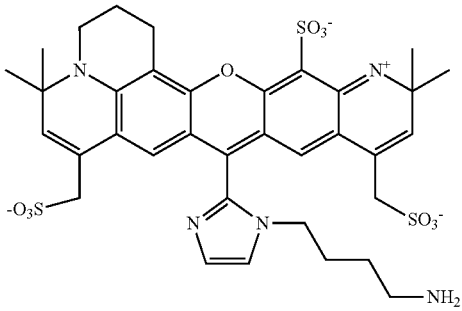 | |
| 32 | 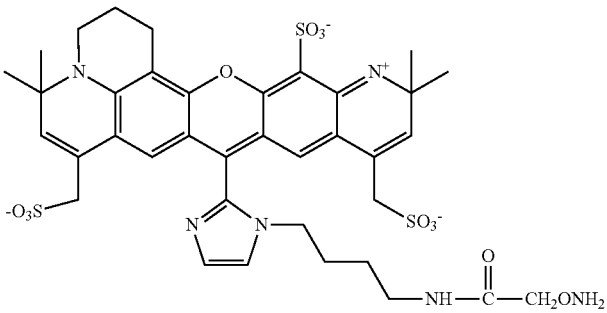 | |
| 33 | 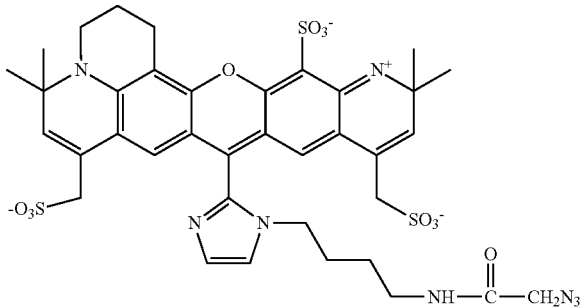 | |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 34 | 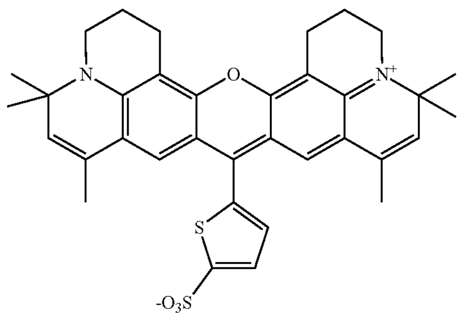 | |
| 35 | 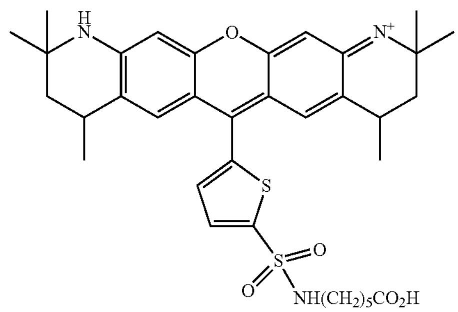 | |
| 36 | 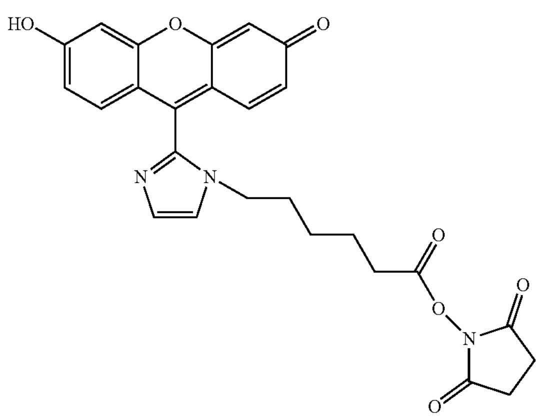 [SMILES: O=C(CCCCCn1ccnc1-c1c2ccc(=O)cc-2oc2cc(O)ccc12)ON1C(=O)CCC1=O] | |
| 37 | 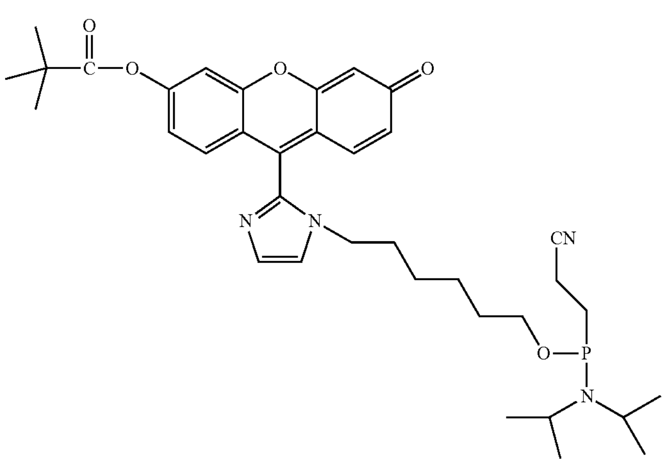 [SMILES: CC(C)N(C(C)C)P(CCC#N)OCCCCCCn1ccnc1-c1c2ccc(=O)cc-2oc2cc(OC(=O)C(C)(C)C)ccc12] | |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 38 | 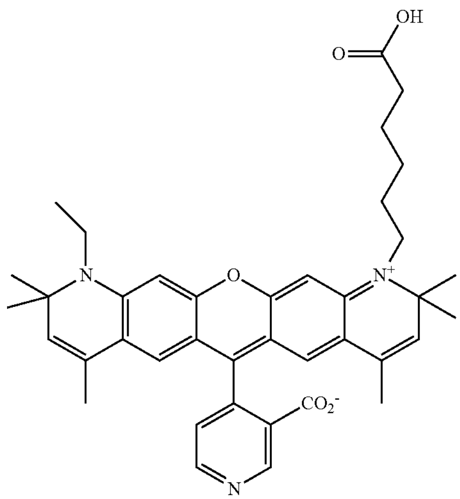 | 599/~620 |
| 39 | 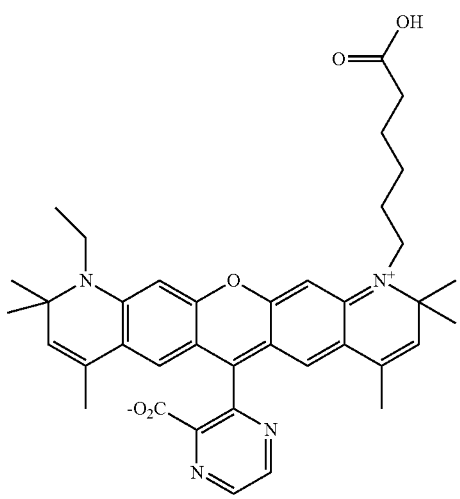 | |
| 40 | 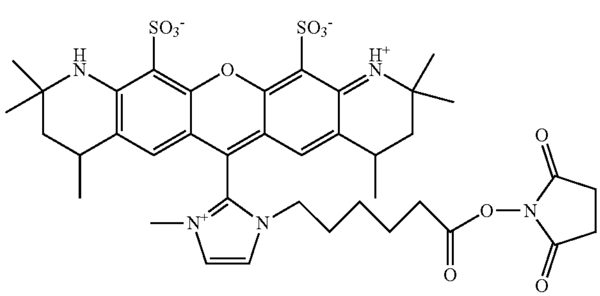 | 592/615 |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 41 | 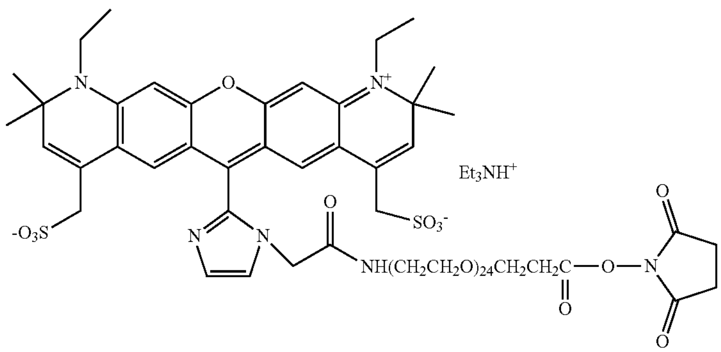 | 627/650 |
| 42 | 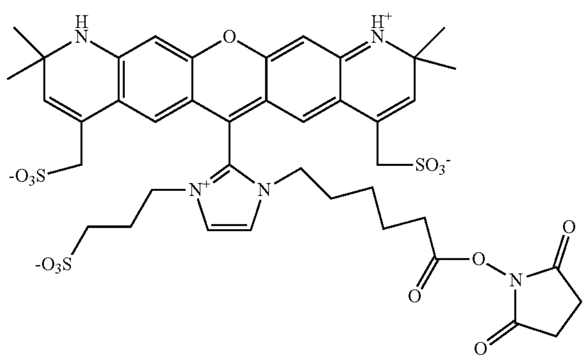 | 642/662 |
| 43 | 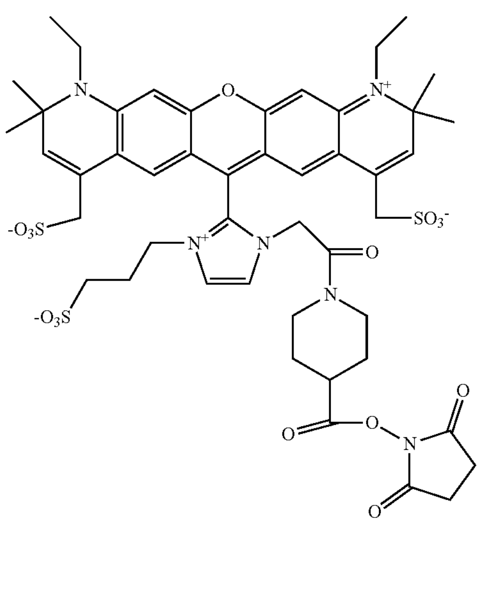 | 660/681 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/ Emission Wavelengths (nm) |
|---|---|---|
| 44 | 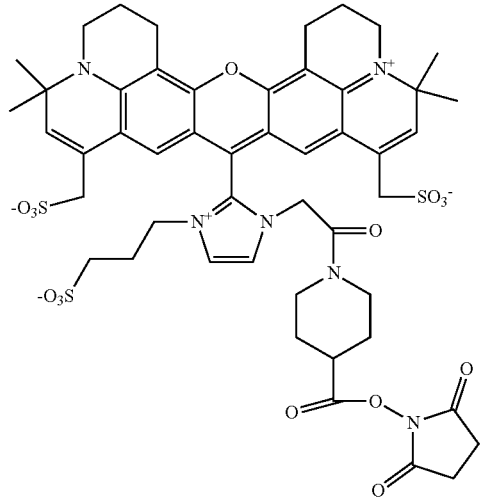 | 683/700 |
| 45 | 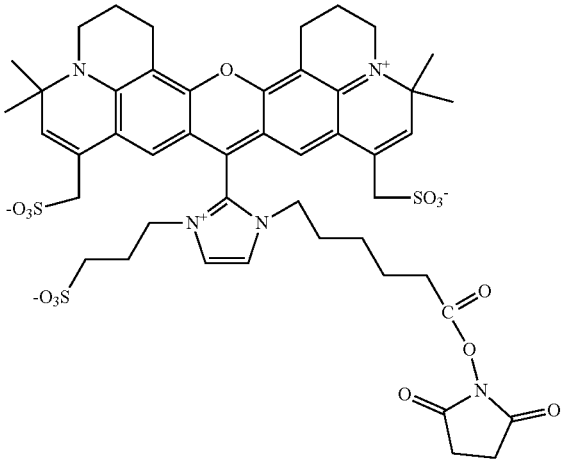 | 680/700 |
| 46 | 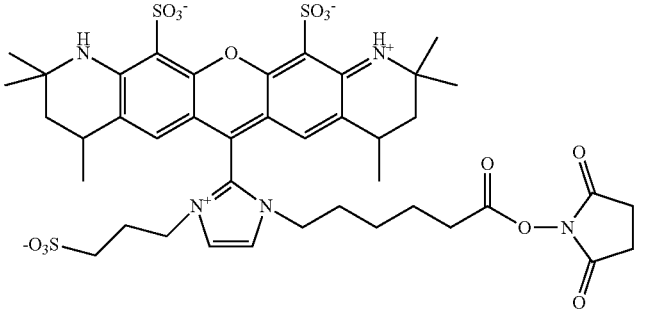 | 593/614 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 47 | 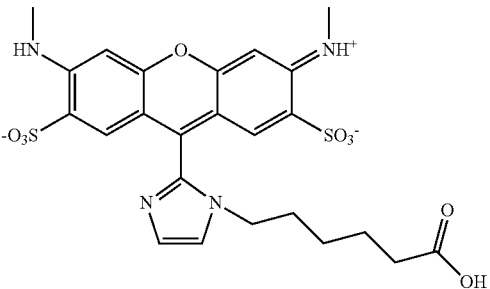 | 578/ |
| 48 | 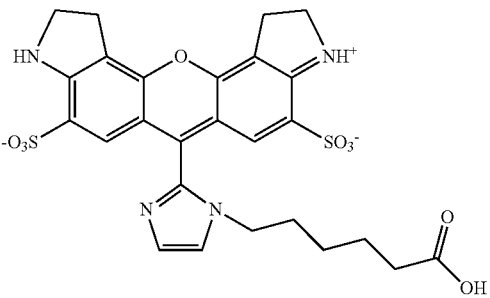 | |
| 49 | 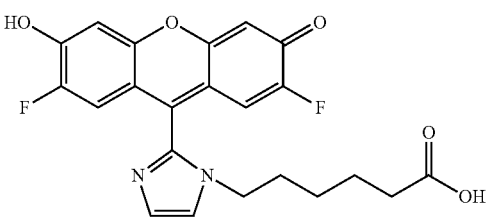 [SMILES: O=C(O)CCCCCn1ccnc1-c1c2cc(F)c(=O)cc-2oc2cc(O)c(F)cc12] | |
| 50 | 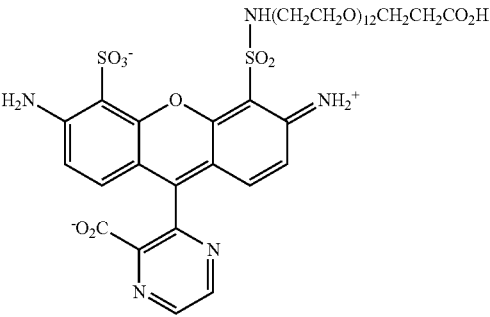 | |
| 51 | 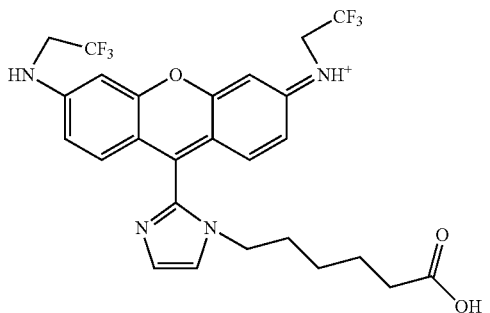 [SMILES: O=C(O)CCCCCn1ccnc1-c1c2cc/c(=[NH+]/CC(F)(F)F)cc-2oc2cc(NCC(F)(F)F)ccc12] | 533/550 |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/ Emission Wavelengths (nm) |
|---|---|---|
| 52 | 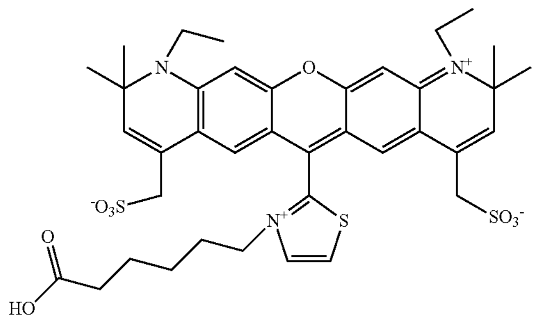 | |
| 53 | 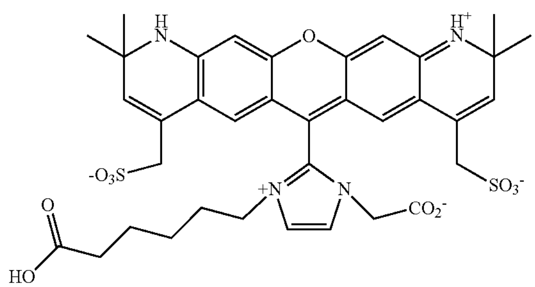 | 642/662 |
| 54 | 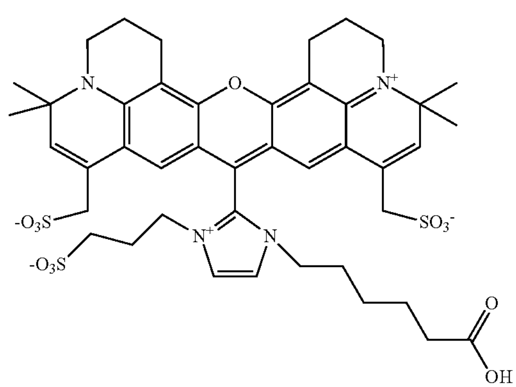 | |

TABLE 3

| Compound No. | Structure | $\lambda_{abs}/\lambda_{em}$ (nm) (in pH 7.4 PBS) |
| --- | --- | --- |
| 55 | 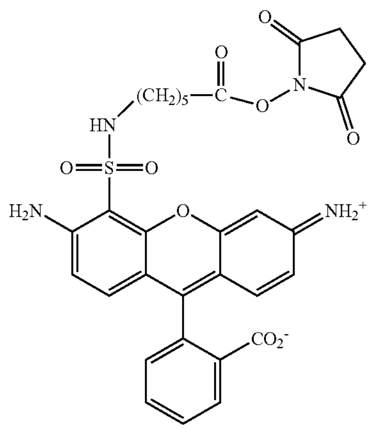 | 488/516 |
| 56 | 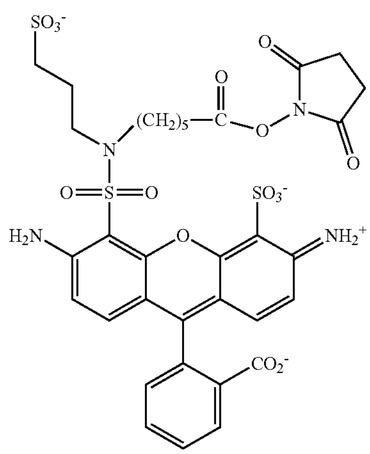 | 488/516 |
| 57 | 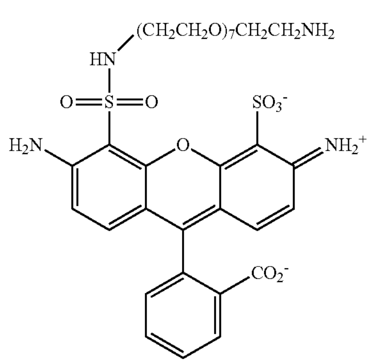 | 488/516 |

TABLE 3-continued

| Compound No. | Structure | $\lambda_{abs}/\lambda_{em}$ (nm) (in pH 7.4 PBS) |
|---|---|---|
| 58 | 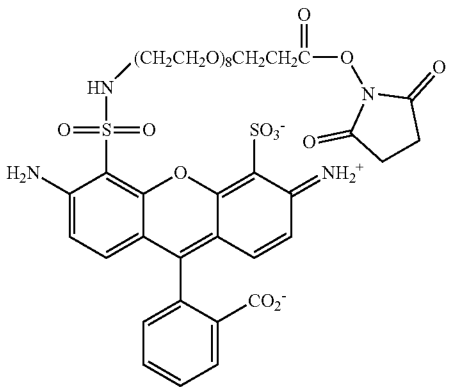 | 488/516 |
| 59 | 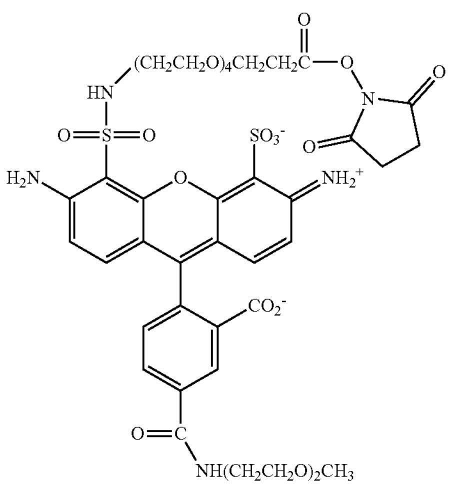 | 488/516 |
| 60 | 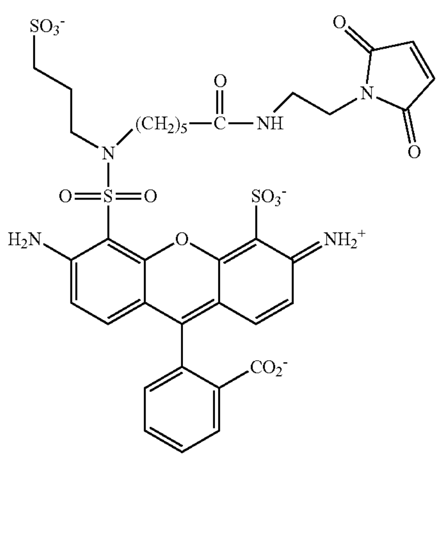 | 488/516 |

TABLE 3-continued

| Compound No. | Structure | $\lambda_{abs}/\lambda_{em}$ (nm) (in pH 7.4 PBS) |
| --- | --- | --- |
| 61 | 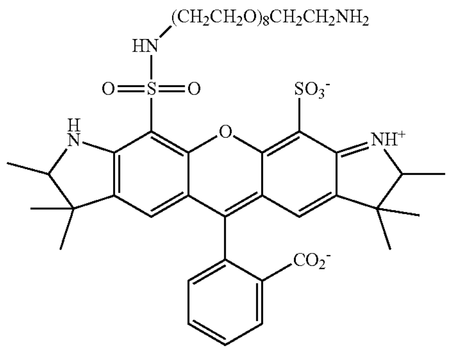 | |
| 62 | 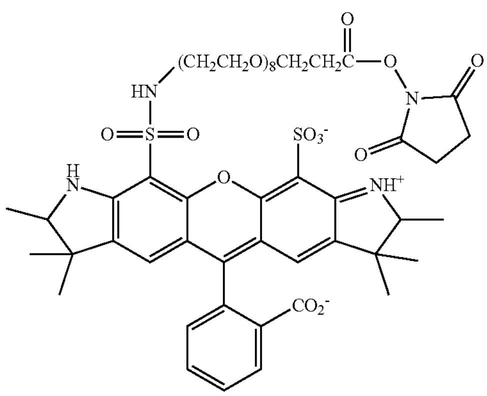 | |
| 63 | 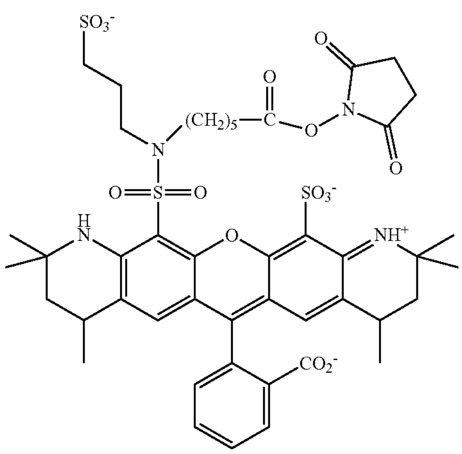 | 529/ |
| 64 | 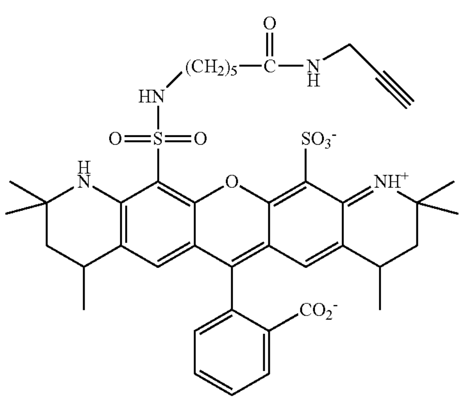 | |

TABLE 3-continued
| Compound No. | Structure | $\lambda_{abs}/\lambda_{em}$ (nm) (in pH 7.4 PBS) |
|---|---|---|
| 65 | 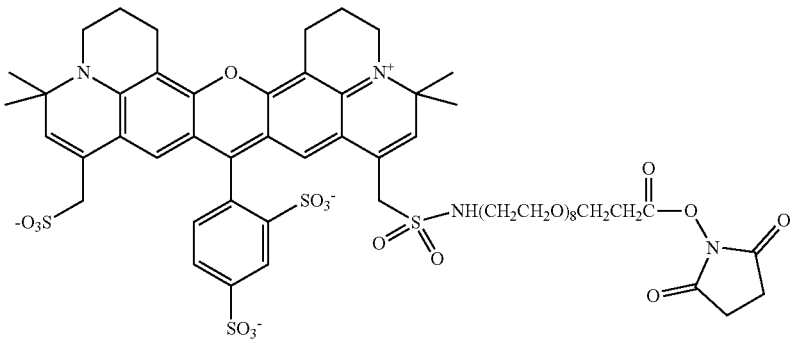 | |
| 66 | 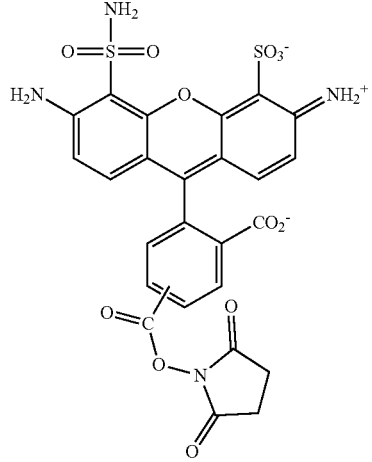 | 490/520 |
| 67 | 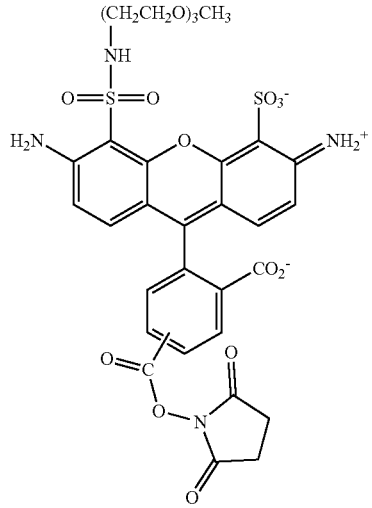 | 490/520 |

TABLE 3-continued
| Compound No. | Structure | $\lambda_{abs}/\lambda_{em}$ (nm) (in pH 7.4 PBS) |
|---|---|---|
| 68 | 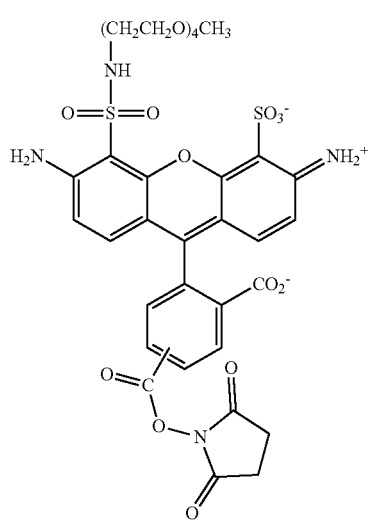 | 490/520 |
TABLE 4
| Compound No. | Structure | $\lambda_{abs}/\lambda_{em}$ (nm) (H$_2$O) |
|---|---|---|
| 69 | 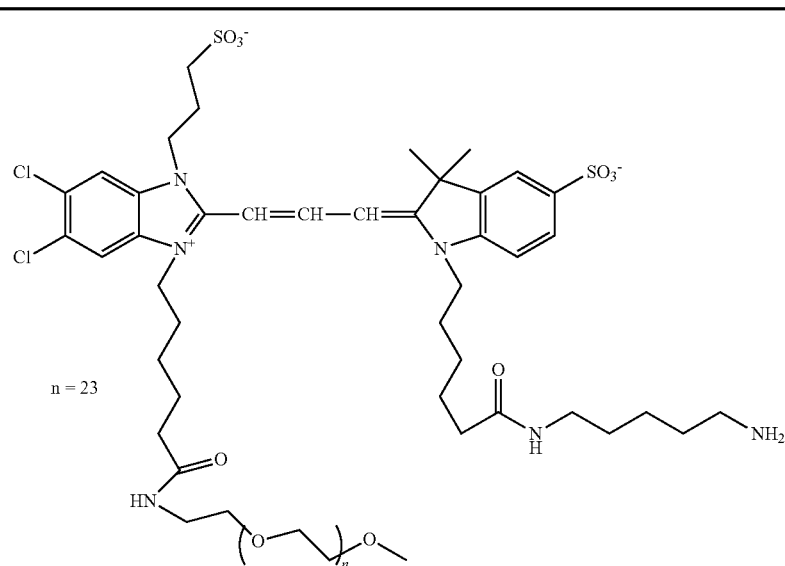 | 457/ |

TABLE 4-continued

| Compound No. | Structure | $\lambda_{abs}/\lambda_{em}$ (nm) (H$_2$O) |
| --- | --- | --- |
| 70 | 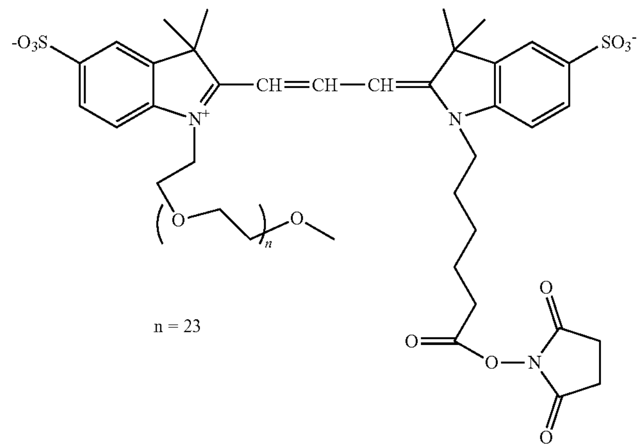 | 550/570 |
| 71 | 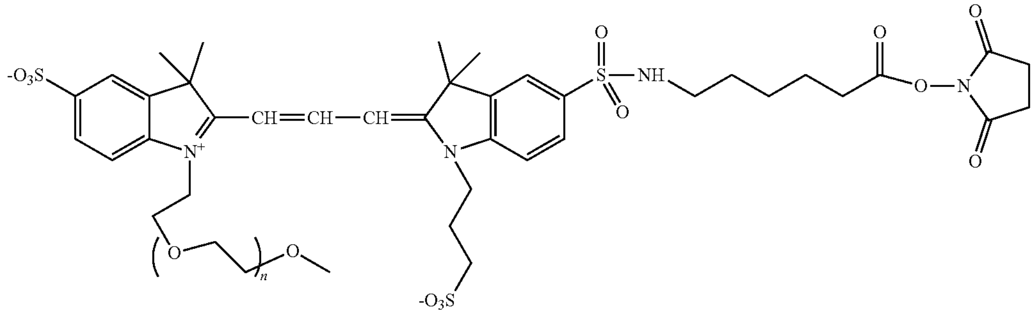 | 550/570 |
| 72 | 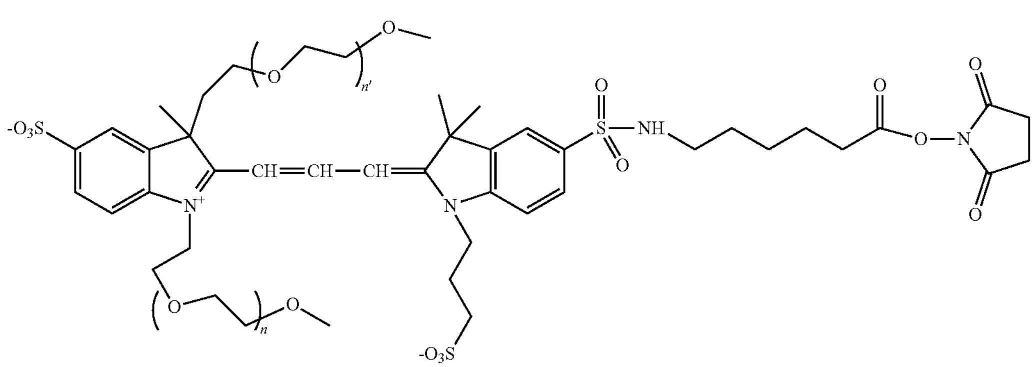 | 550/570 |

TABLE 4-continued

| Compound No. | Structure | $\lambda_{abs}/\lambda_{em}$ (nm) (H$_2$O) |
| --- | --- | --- |
| 73 | 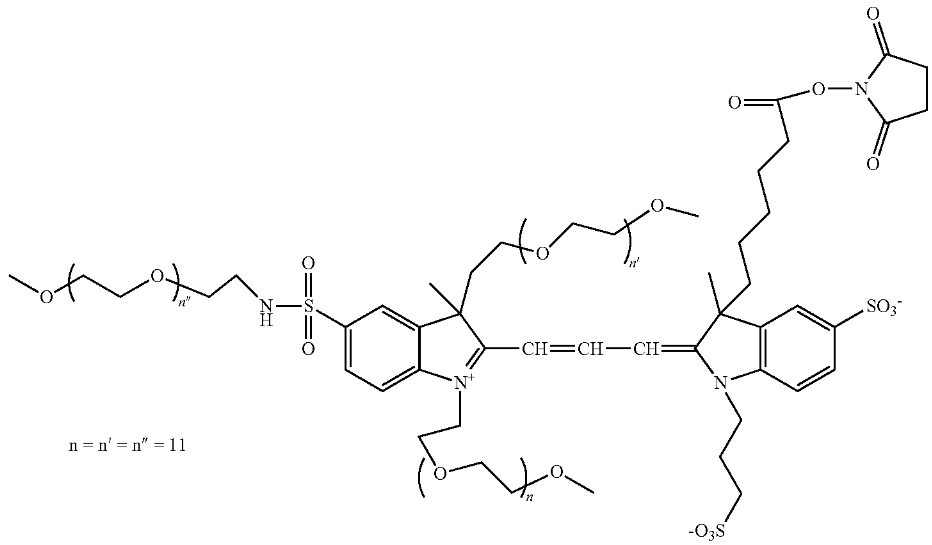 | 550/570 |
| 74 | 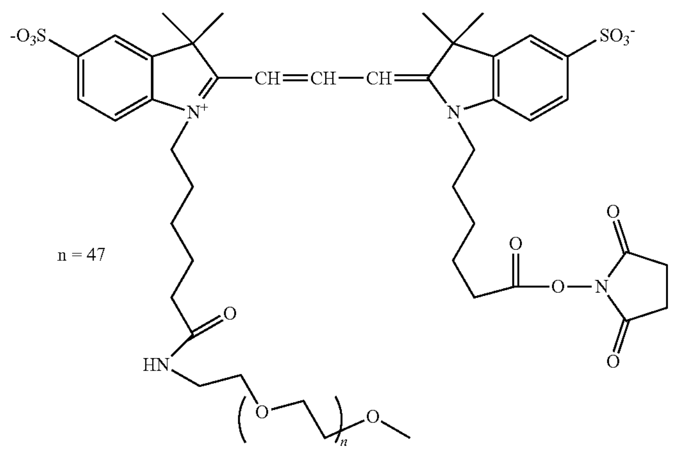 | 550/570 |
| 75 | 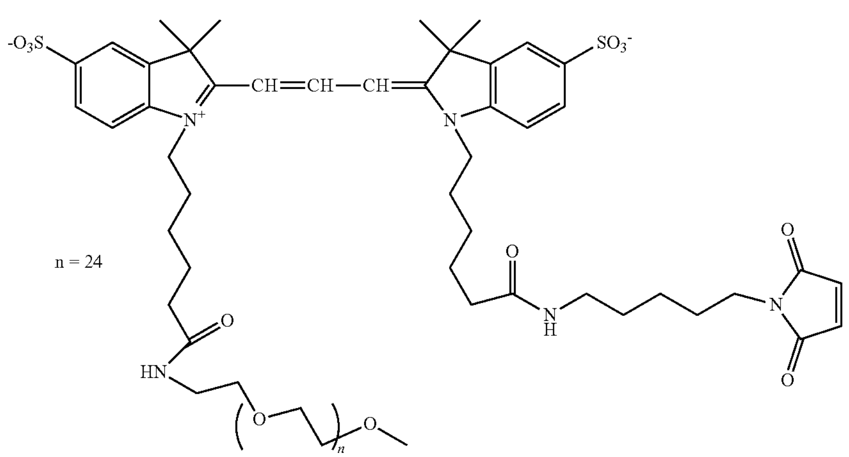 | 550/570 |

TABLE 4-continued
| Compound No. | Structure | $\lambda_{abs}/\lambda_{em}$ (nm) (H$_2$O) |
|---|---|---|
| 76 | 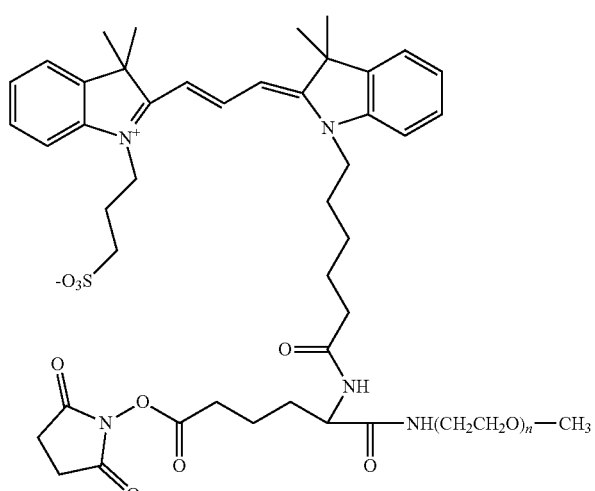 n' = 12 | 550/570 |
| 77 | 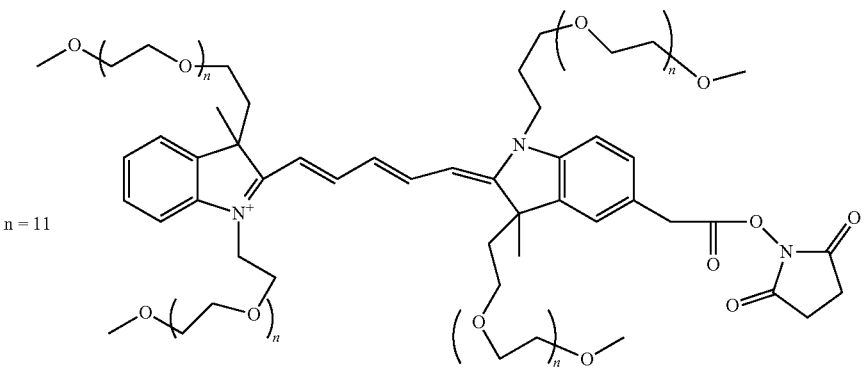 n = 11 | 650/665 |
| 78 | 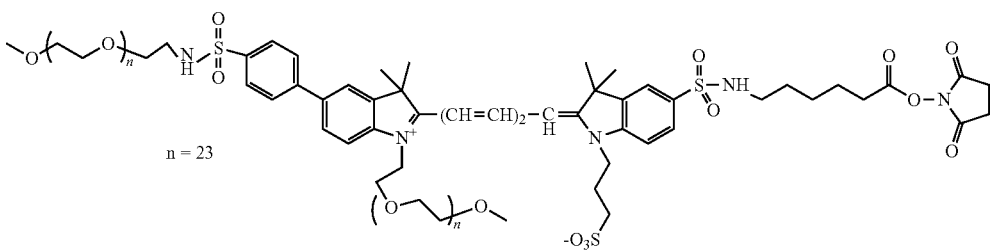 n = 23 | 650/665 |

TABLE 4-continued
| Compound No. | Structure | $\lambda_{abs}/\lambda_{em}$ (nm) (H$_2$O) |
|---|---|---|
| 79 | 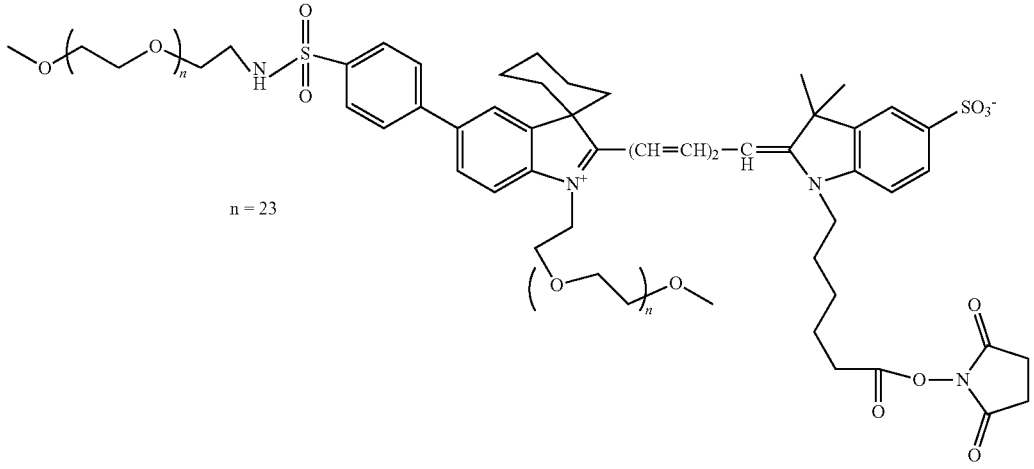 n = 23 | 650/665 |
| 80 | 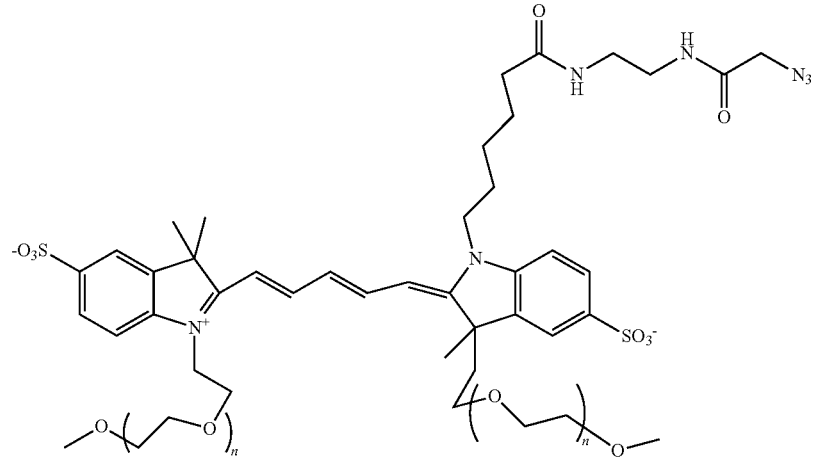 n = 23 | 650/665 |
| 81 | 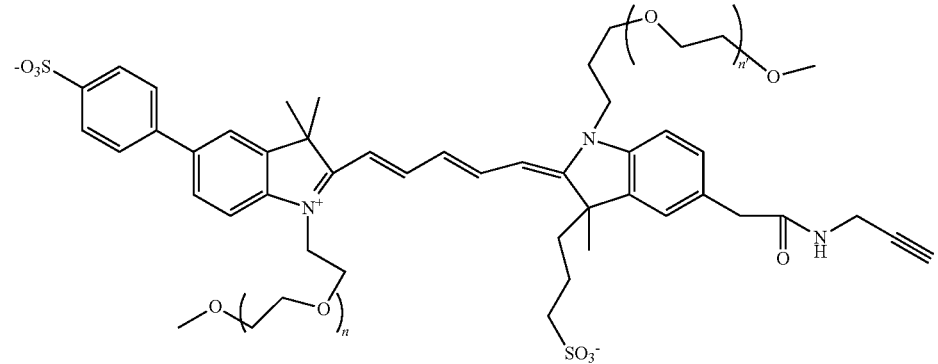 n = 23<br>n' = 11 | 650/665 |

TABLE 4-continued
| Compound No. | Structure | $\lambda_{abs}/\lambda_{em}$ (nm) (H$_2$O) |
|---|---|---|
| 82 | 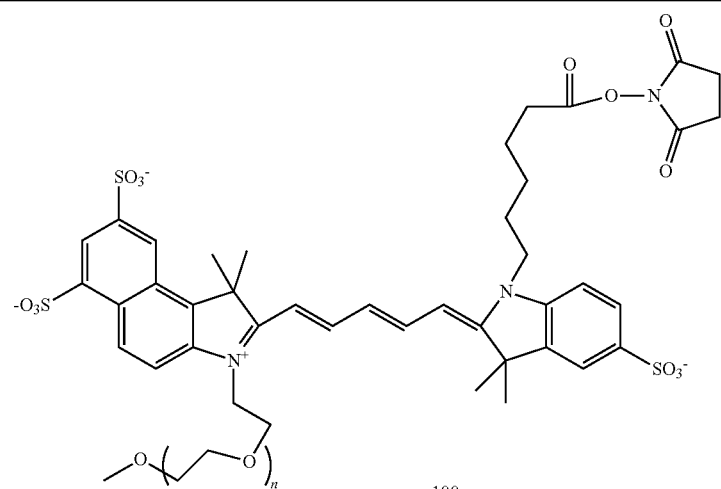 n = ~100 | 660/680 |
| 83 | 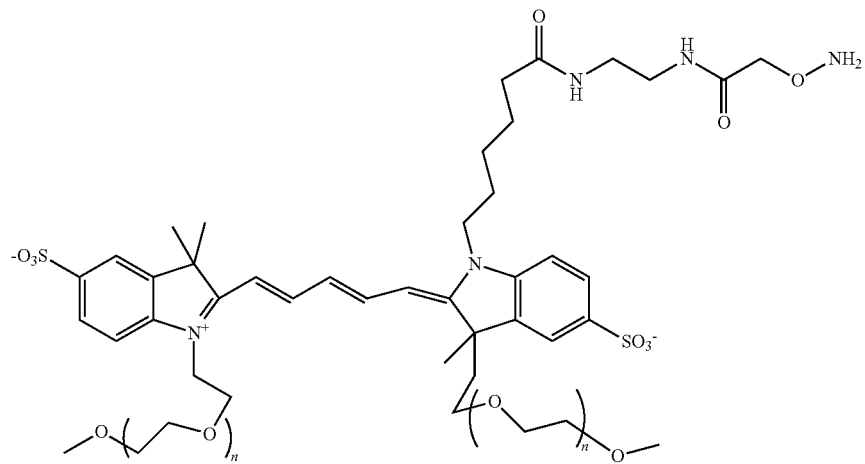 n = 23 | 650/665 |
| 84 | 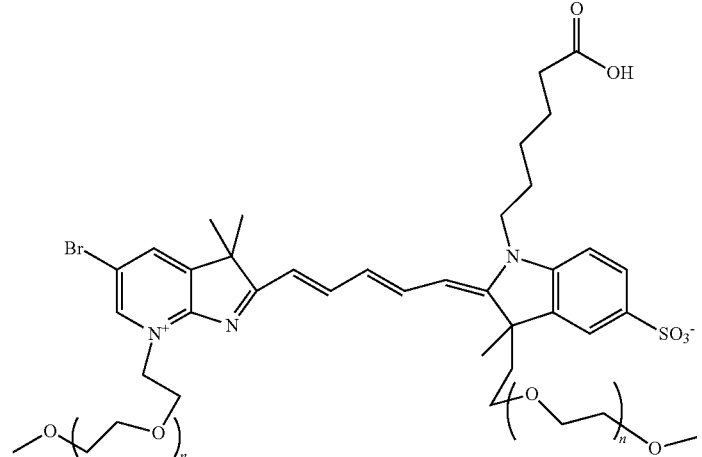 n = 23 | 663/690 |

TABLE 4-continued
| Compound No. | Structure | $\lambda_{abs}/\lambda_{em}$ (nm) (H$_2$O) |
|---|---|---|
| 85 | 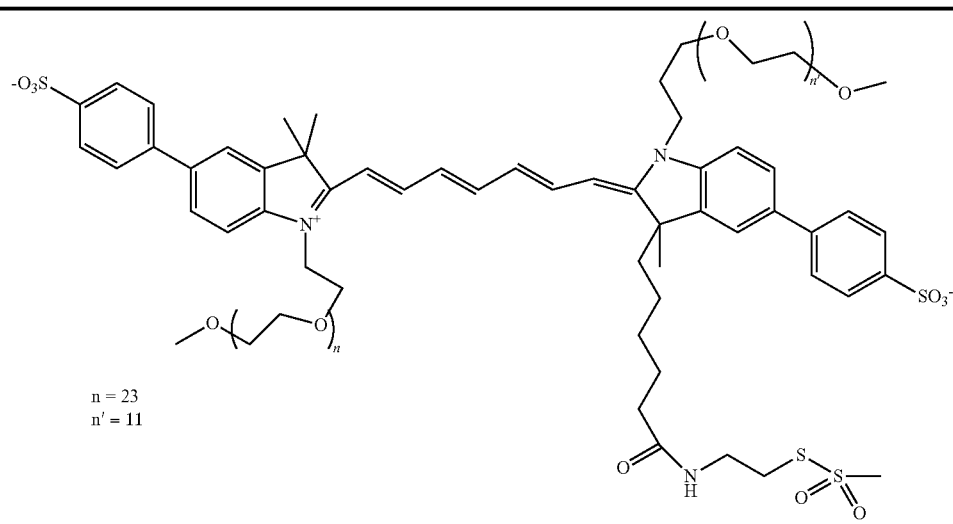 n = 23, n' = 11 | 752/778 |
| 86 | 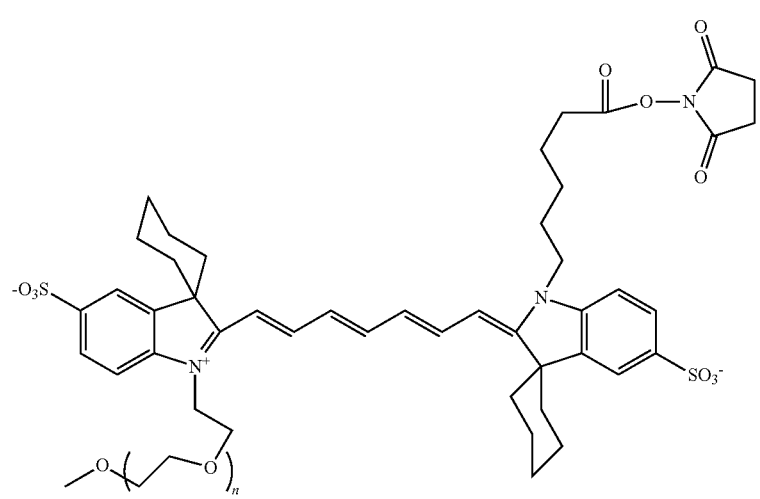 n = 23 | 750/775 |
| 87 | 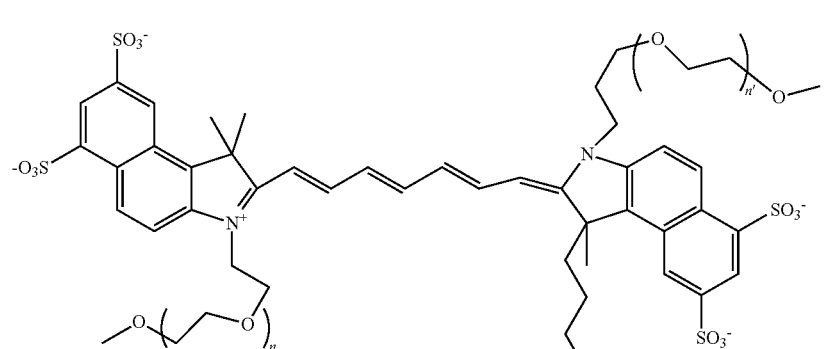 n = 23, n' = 11 | 675/694 |

TABLE 4-continued
| Compound No. | Structure | $\lambda_{abs}/\lambda_{em}$ (nm) (H$_2$O) |
|---|---|---|
| 88 | 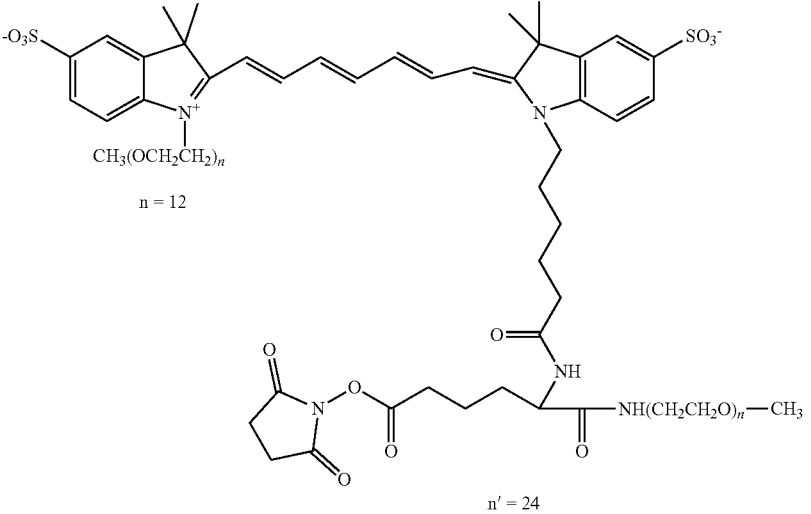 | 750/775 |
| 89 | 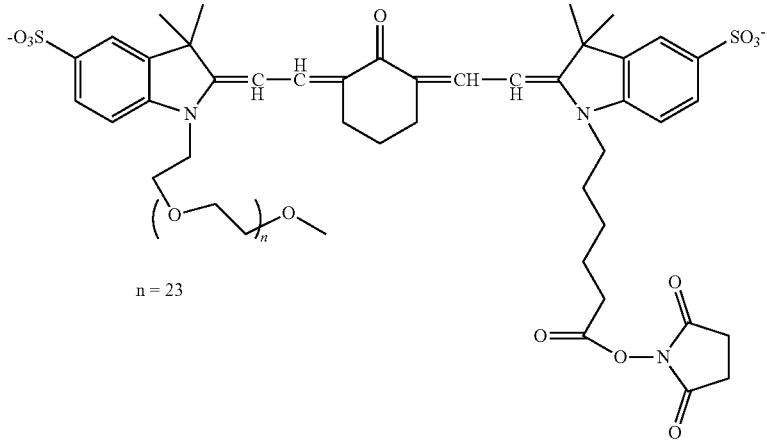 | |
| 90 | 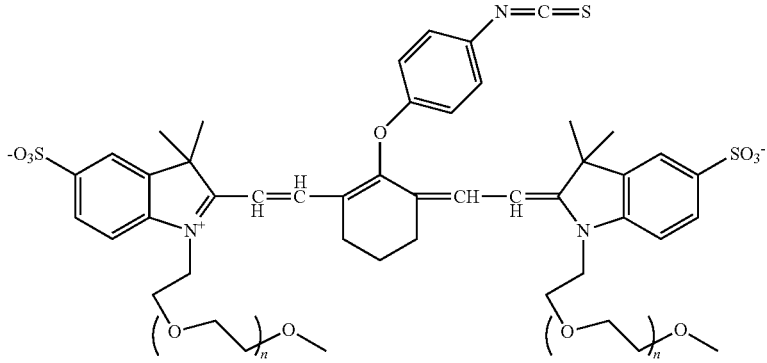 | 768/788 |

TABLE 4-continued
| Compound No. | Structure | $\lambda_{abs}/\lambda_{em}$ (nm) (H$_2$O) |
|---|---|---|
| 91 | 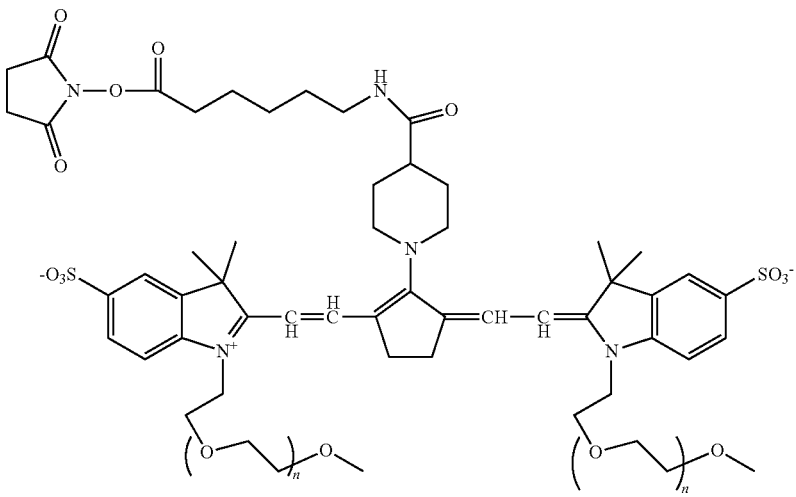 n = 24 | |
| 92 | 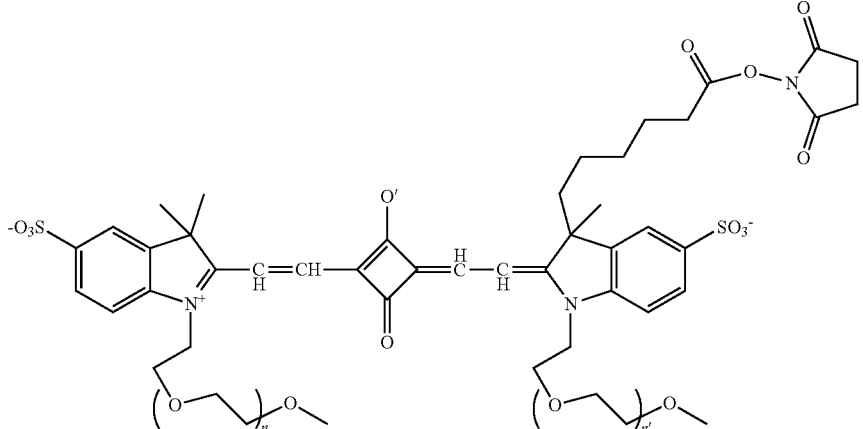 n = 23   n' = 12 | 635/642 |
| 93 | 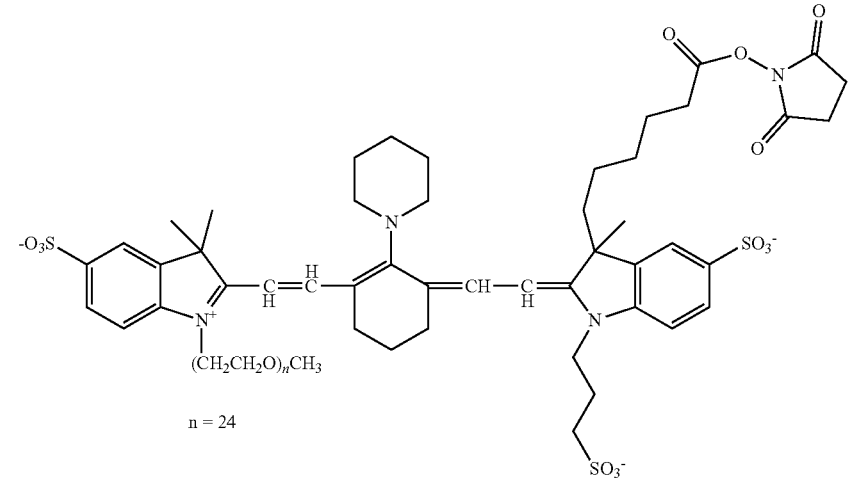 n = 24 | |

TABLE 4-continued

| Compound No. | Structure | $\lambda_{abs}/\lambda_{em}$ (nm) (H$_2$O) |
|---|---|---|
| 94 | [Structure: benzoxazole trimethine cyanine dye with sulfonated phenyl groups, cysteine-sulfonamide substituent; R = —(CH$_2$)$_5$CONH(CH$_2$CH$_2$O)$_{24}$CH$_3$] | 497/513 |
| 95 | [Structure: sulfoindocyanine trimethine (Cy3-type) dye with NHS ester on one indoline; R = —(CH$_2$)$_5$CONH(CH$_2$CH$_2$O)$_{24}$CH$_3$] | 555/565 |
| 96 | [Structure: sulfoindocyanine pentamethine (Cy5-type) dye with NHS ester on one indoline; R = —(CH$_2$)$_5$CONH(CH$_2$CH$_2$O)$_{24}$CH$_3$] | 650/665 |

TABLE 4-continued

| Compound No. | Structure | $\lambda_{abs}/\lambda_{em}$ (nm) (H$_2$O) |
|---|---|---|
| 97 | (structure with cyanine dye, indole groups with -O$_3$S and SO$_3^-$ substituents, (CH=CH)$_3$CH linker, NHS ester, R = —(CH$_2$)$_5$CONH(CH$_2$CH$_2$O)$_{24}$CH$_3$) | 750/770 |
| 98 | (structure with cyanine dye, indole with -O$_3$S and benzoindole with two SO$_3^-$, (CH=CH)$_2$CH linker, NHS ester, R = —(CH$_2$)$_5$CONH(CH$_2$CH$_2$O)$_{24}$CH$_3$) | 660/675 |
| 99 | (structure with cyanine dye, indole with -O$_3$S and benzoindole with two SO$_3^-$, (CH=CH)$_3$CH linker, NHS ester, R = —(CH$_2$)$_5$CONH(CH$_2$CH$_2$O)$_{24}$CH$_3$) | 770/790 |

TABLE 4-continued
| Compound No. | Structure | $\lambda_{abs}/\lambda_{em}$ (nm) (H$_2$O) |
|---|---|---|
| 100 | 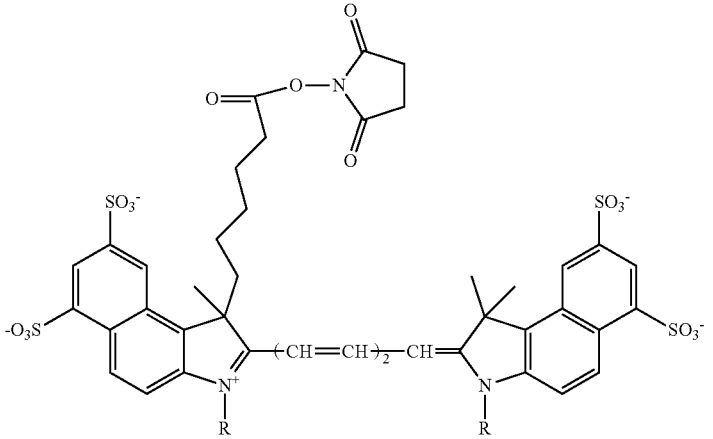 —R = —(CH$_2$)$_5$CONH(CH$_2$CH$_2$O)$_{24}$CH$_3$ | 680/700 |
| 101 | 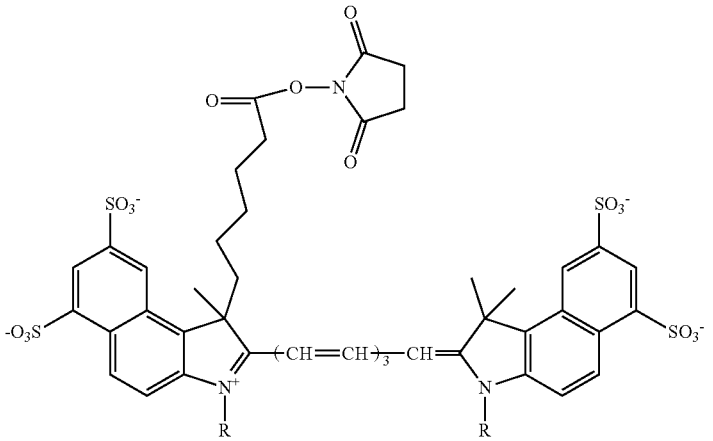 —R = —(CH$_2$)$_5$CONH(CH$_2$CH$_2$O)$_{24}$CH$_3$ | 790/810 |
| 102 | 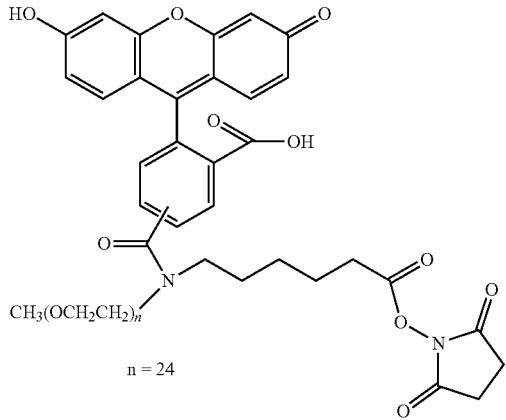 n = 24 | 494/520 |

TABLE 4-continued

| Compound No. | Structure | $\lambda_{abs}/\lambda_{em}$ (nm) (H$_2$O) |
|---|---|---|
| 103 | (structure with n = 24) | |
| 104 | (structure with n = 24) | 501/524 |
| 105 | (structure with n = 24) | |
| 106 | (structure) | |

TABLE 4-continued
| Compound No. | Structure | $\lambda_{abs}/\lambda_{em}$ (nm) (H$_2$O) |
|---|---|---|
| 107 | 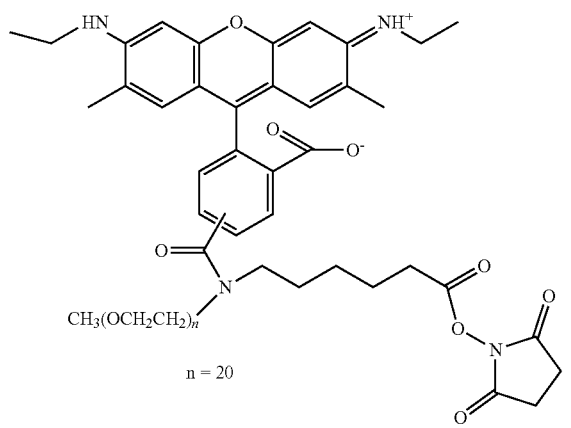 n = 20 | 520/546 |
| 108 | 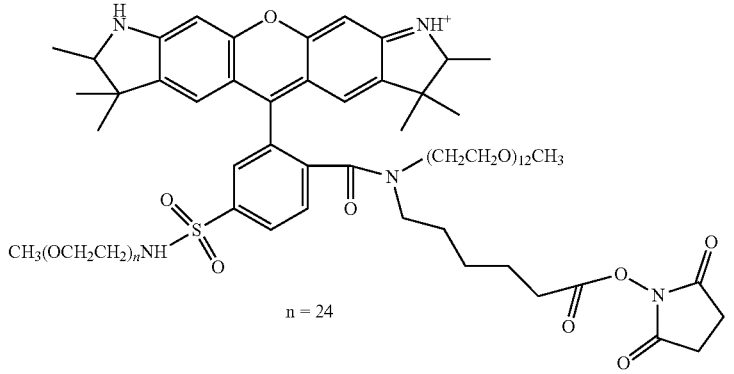 n = 24 | |
| 109 | 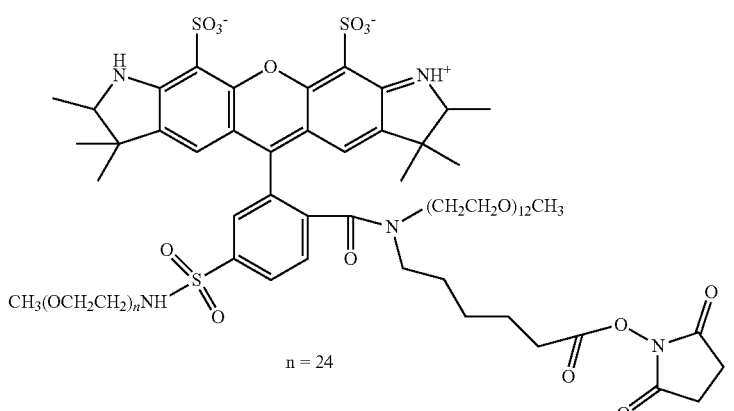 n = 24 | |

TABLE 4-continued
| Compound No. | Structure | $\lambda_{abs}/\lambda_{em}$ (nm) (H$_2$O) |
|---|---|---|
| 110 | 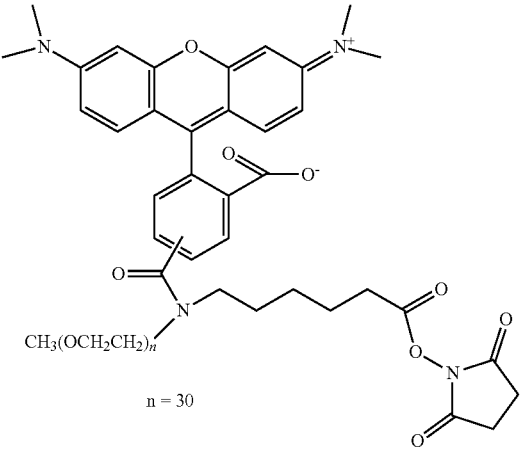 | 540/565 |
| 111 | 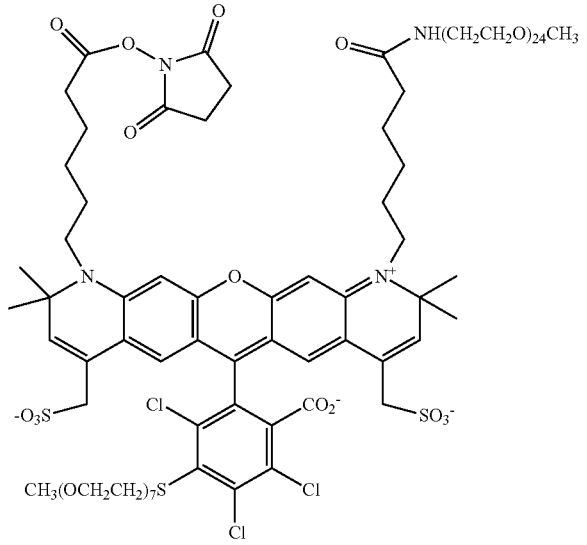 | |
| 112 | 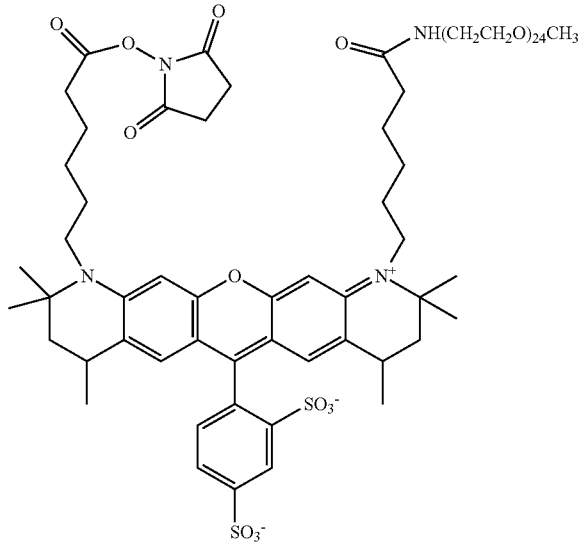 | |

TABLE 4-continued
| Compound No. | Structure | $\lambda_{abs}/\lambda_{em}$ (nm) (H$_2$O) |
|---|---|---|
| 113 | 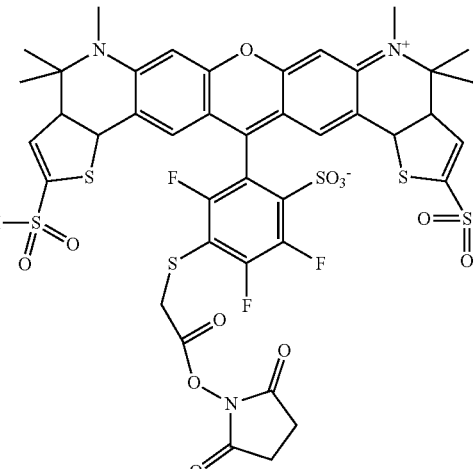 | |
| 114 | 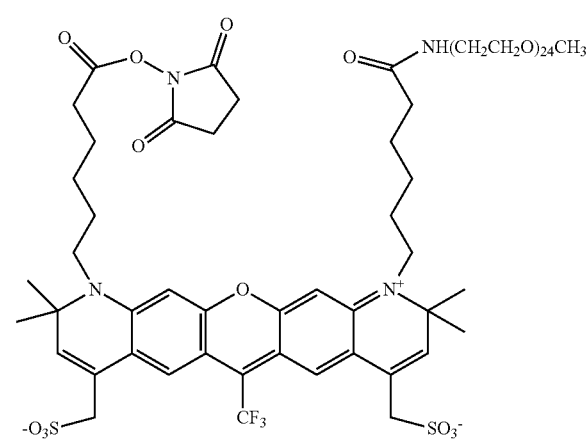 | |
| 115 | 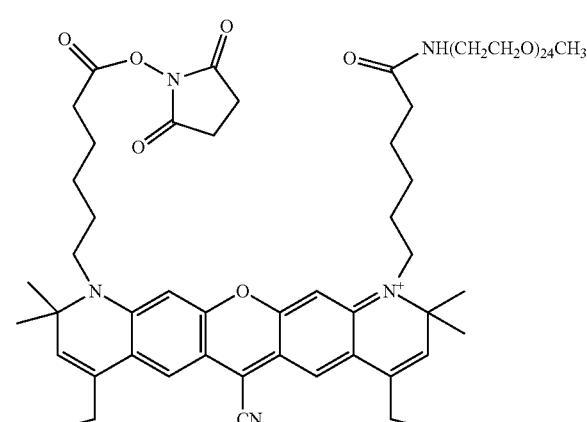 | |

TABLE 4-continued

| Compound No. | Structure | $\lambda_{abs}/\lambda_{em}$ (nm) (H$_2$O) |
| --- | --- | --- |
| 116 | (structure shown); R = —(CH$_2$CH$_2$O)$_{24}$CH$_3$ | 488/515 |
| 117 | (structure shown); R = —(CH$_2$CH$_2$O)$_{24}$CH$_3$ | 494/520 |
| 118 | (structure shown) | 353/442 |
| 119 | (structure shown) | 346/442 |

TABLE 4-continued
| Compound No. | Structure | $\lambda_{abs}/\lambda_{em}$ (nm) (H$_2$O) |
|---|---|---|
| 120 | 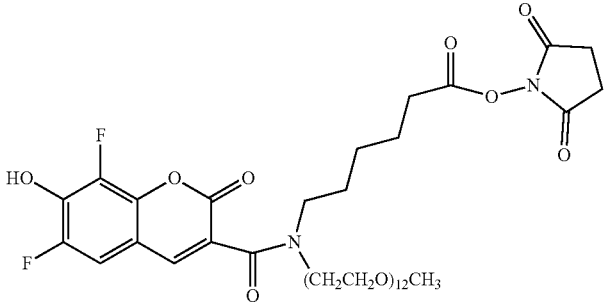 | 416/465 |
| 121 | 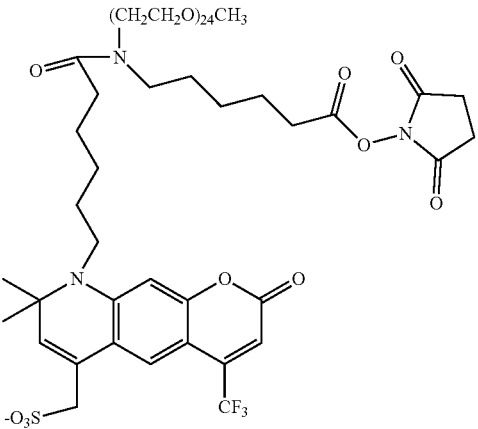 | 430/545 |
| 122 | 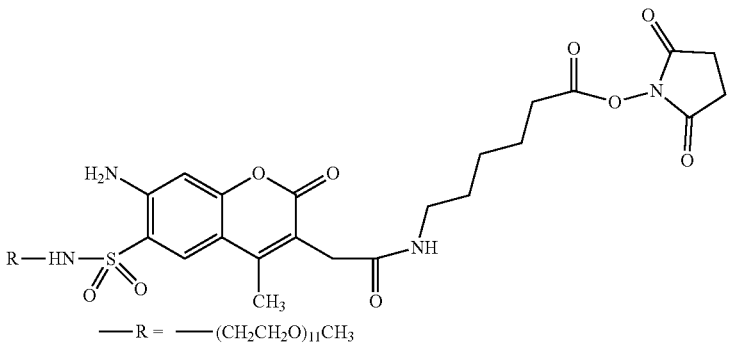 | 350/440 |
| 123 | 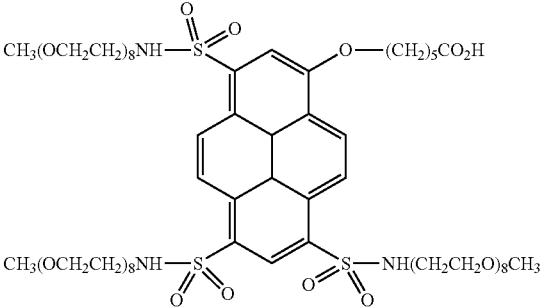 | |

TABLE 4-continued

| Compound No. | Structure | $\lambda_{abs}/\lambda_{em}$ (nm) (H$_2$O) |
|---|---|---|
| 124 | 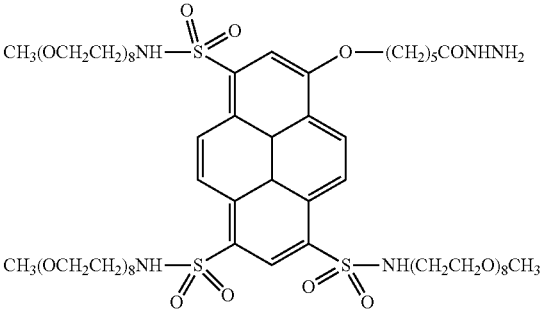 | |
| 125 | 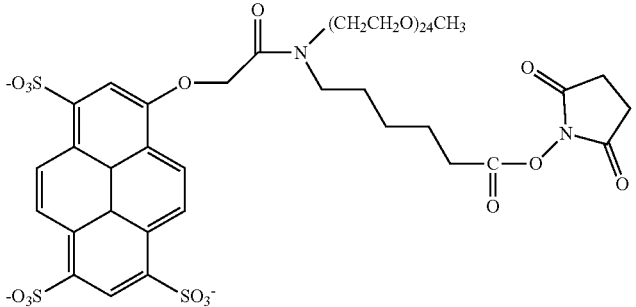 | 400/424 |

Examples

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Analysis of Cells Stained with Secondary Antibody Labeled with Compound No. 126

This example describes the labeling of an antibody with a green fluorescent sulfonated xanthene dye, and the use of such antibodies for intracellular staining and flow cytometry analysis. The dye used in this example, Compound No. 126, absorbs light at about 491 nm and emits light at about 525 nm. The structure of Compound No. 126 is as follows:

Compound No. 126

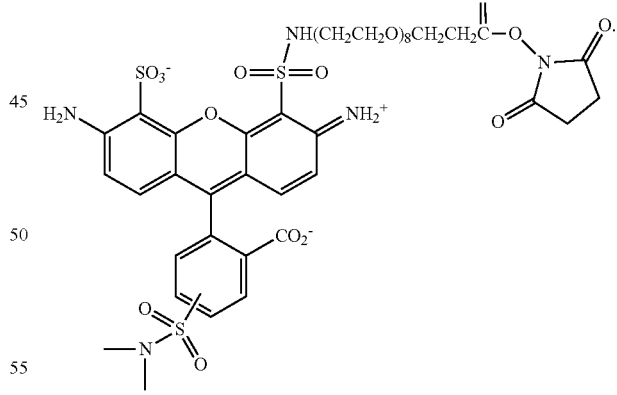

Solutions of goat anti-mouse (GAM) labeled with Compound No. 126 were prepared using different dye-to-antibody ratios and different antibody concentrations in a reaction buffer comprising 10 mM Tris and 50 mM NaHCO$_3$ (pH 8.3). Detailed labeling reaction conditions are listed in Table 5 below. Labeling reactions were carried out by combining antibody and dye in reaction buffer followed by 30 minutes of incubation. Reaction buffer comprised 10 mM Tris and 50 mM NaHCO$_3$ with pH ~8.3. Each labeled GAM solution was diluted in a storage buffer and then used in cell staining.

Storage buffer (~20 mL) was prepared by mixing 10 mL 75 mM Tris pH7 buffer, 200 mg BSA, 150 uL 5% NaN$_3$, 10 mL glycerol and 10 mg lysine.

TABLE 5

| Labeled GAM IgG antibody solution | Labeling condition ||||| 
|---|---|---|---|---|---|
| | Amount of GAM IgG (µg) | Antibody concentration in reaction (mg/mL) | Amount of dye (nmoles) | Antibody-to-dye ratio (ug/nmole) | Amount of storage buffer (uL) |
| #1 | 100 | 1 | 11.25 | 8.9:1 | 300 |
| #2 | 50 | 2 | 11.25 | 4.4:1 | 300 |
| #3 | 20 | 2 | 5.6 | 3.6:1 | 150 |
| #4 | 20 | 1 | 2.8 | 7.2:1 | 60 |
| #5 | 5 | 1 | 2.8 | 1.8:1 | 60 |
| #6 | 100 | 1 | 9.4 | 10.6:1 | 300 |
| #7 | 50 | 2 | 9.4 | 5.3:1 | 300 |
| #8 | 100 | 1 | 7.5 | 13.3:1 | 300 |
| #9 | 50 | 2 | 7.5 | 6.7:1 | 30 |

Purified dye-GAM IgG conjugate was also prepared for cell staining as a control. The purified antibody conjugate was prepared using a standard antibody conjugation method. Briefly, Compound No. 126 (180 nmoles) in 50 uL dimethylformamide (DMF) was added to 1 mg of goat anti-mouse at 1 mg/mL in 0.1 mM NaHCO$_3$(pH 8.3), followed by incubation at room temperature for 1 hour. The reaction solution was subject to G-25 Sephadex column equilibrated in and eluted with 1×PBS to result in the purified antibody conjugate. This is referred to as "purified Dye No. 1-GAM" in FIG. 1.

One million Jurkat cells per sample were stained with 0.25 µg mouse anti-human CD3 (BD Biosciences) followed by 1 µg of a dye-GAM IgG conjugate prepared according to the above table or 1 µg of the purified GAM conjugate. About 10,000 cells from each sample were analyzed on a BD FACSCalibur flow cytometer (BD Biosciences), and fluorescence was detected in the FL1 channel using 488 nm excitation. Noise represents the average intensity from cells stained with only goat anti-mouse secondary conjugates. Signal represents average fluorescence intensity from cells stained with CD3 and labeled goat anti-mouse IgG. The data are plotted in FIG. 1. The results show that cells stained with antibodies labeled according to the invention show high relative fluorescence (white bars) with low background fluorescence (black bars), and perform comparably to the purified antibody. FIG. 1 also demonstrates a lack of correlation between relative fluorescence and the staining conditions tested, indicating that cell staining is independent of the conditions under which the labeled antibodies are prepared (i.e., the antibody-to-dye ratio and antibody concentration).

Example 2: Analysis of Cells Stained with Secondary Antibody Labeled with Compound No. 42

This example describes labeling of an antibody with a far-red fluorescent sulfonated xanthene dye (Compound No. 42), and the use of such antibodies for intracellular staining and flow cytometry analysis.

Solutions of goat anti-mouse (GAM) labeled with Compound No. 42 were prepared using different dye-to-antibody ratios and different antibody concentrations in a reaction buffer comprising 10 mM Tris and 50 mM NaHCO$_3$ (pH 8.3). Detailed labeling reaction conditions are listed in Table 6 below. Labeling reactions were carried out by combining antibody and dye in reaction buffer followed by 30 minutes of incubation. Reaction buffer comprised 10 mM Tris and 50 mM NaHCO$_3$ with pH ~8.3. Each labeled GAM solution was diluted in a storage buffer and then used in cell staining. A typical storage buffer (~20 mL) was prepared by mixing 10 mL 75 mM Tris pH7 buffer, 200 mg BSA, 150 uL 5% NaN$_3$, 10 mL glycerol and 10 mg lysine.

TABLE 6

| Labeled GAM IgG antibody solution | Labeling condition |||||
|---|---|---|---|---|---|
| | Amount of GAM IgG (µg) | Antibody concentration in reaction (mg/mL) | Amount of dye (nmoles) | Antibody-to-dye ratio (ug/nmole) | Amount of storage buffer (uL) |
| #1 | 100 | 1 | 11.25 | 8.9:1 | 300 |
| #2 | 50 | 2 | 11.25 | 4.4:1 | 300 |
| #3 | 20 | 2 | 5.6 | 3.6:1 | 150 |
| #4 | 20 | 1 | 2.8 | 7.2:1 | 60 |
| #5 | 5 | 1 | 2.8 | 1.8:1 | 60 |
| #6 | 100 | 1 | 9.4 | 10.6:1 | 300 |
| #7 | 50 | 2 | 9.4 | 5.3:1 | 300 |
| #8 | 100 | 1 | 7.5 | 13.3:1 | 300 |
| #9 | 50 | 2 | 7.5 | 6.7:1 | 30 |

Purified Dye-GAM IgG conjugate was also prepared for cell staining as a control. The purified antibody conjugate was prepared using standard antibody conjugation method. Briefly, Compound No. 42 (130 nmoles) in 50 uL DMF was added to 1 mg of goat anti-mouse at 1 mg/mL in 0.1 mM NaHCO$_3$, followed by incubation at room temperature for 1 hour. The reaction solution was subject to G-25 Sephadex column equilibrated in and eluted with 1×PBS to result in the purified antibody conjugate. This is referred to as "purified Dye No. 2-GAM conjugate" in FIG. 2.

Figure 2:
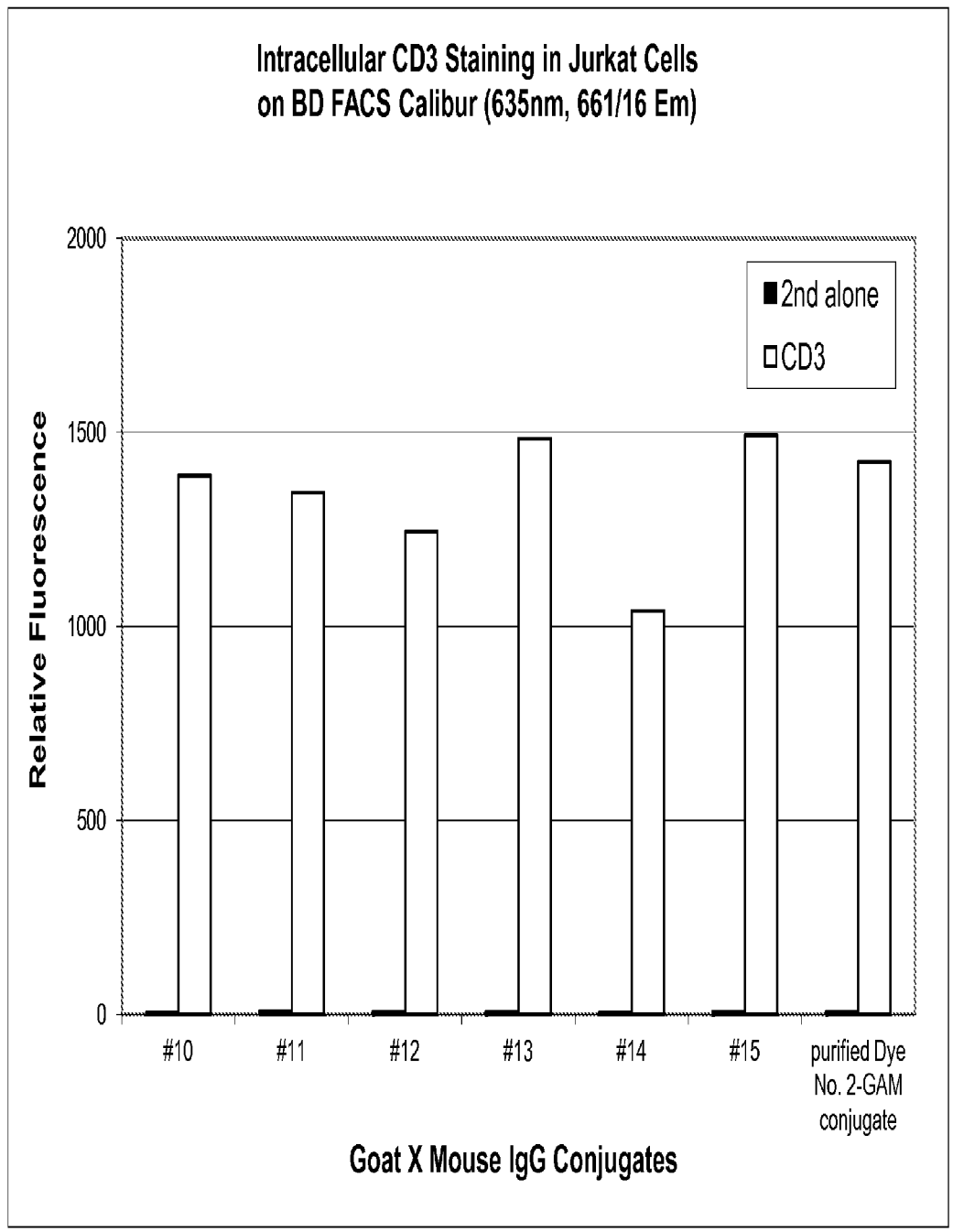
FIG. 2 shows the results of a flow cytometry analysis of cells stained with secondary antibodies labeled according to methods of the invention.

Cell staining was performed as in Example 1. Stained samples were analyzed on BD FACS Calibur using 635 nm excitation and FL4 detection channel. Relative fluorescence signals are shown in FIG. 2. The data show that cell immunostaining according to the invention and that according to the conventional method using a purified antibody conjugate produced comparable results.

Example 3: Analysis of Cells Stained with Secondary Antibody Labeled with One of Two Compounds This example describes labeling of an antibody with either a near-IR fluorescent sulfonated xanthene dye (Compound No. 45) or a near-IR sulfonated cyanine dye (Compound No. 127), and the use of such antibodies for intracellular staining and flow cytometry analysis. Compound No. 127, absorbs light at about 680 nm and emits light at about 698 nm. The structure of Compound No. 127 is as follows:

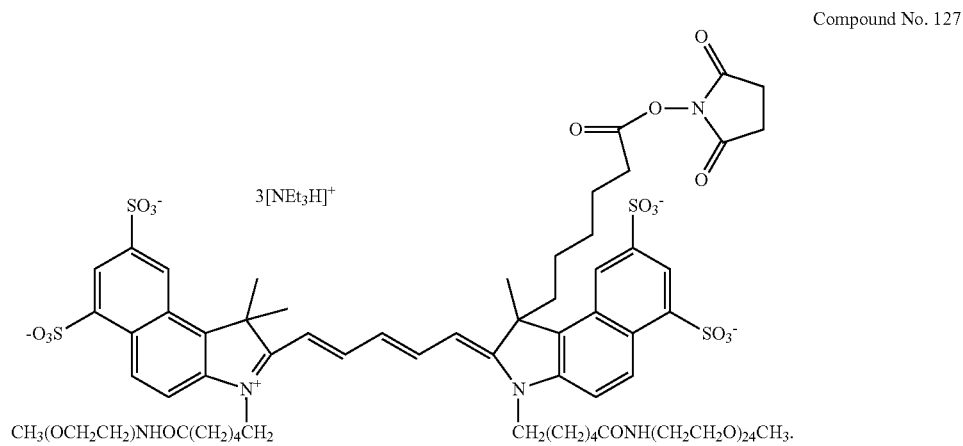

Compound No. 127

Solutions of goat anti-mouse (GAM) labeled with Compound No. 45 or Compound No. 127 were prepared using different dye-to-antibody ratios and different antibody concentrations in a reaction buffer comprising 10 mM Tris and 50 mM NaHCO$_3$ (pH 8.3). Detailed labeling reaction conditions are listed in Table 7 below. Labeling reactions were carried out by combining antibody and dye in reaction buffer followed by 30 minutes of incubation. Reaction buffer comprised 10 mM Tris and 50 mM NaHCO$_3$ with pH ~8.3. Each labeled GAM solution was diluted in a storage buffer and then used in cell staining. A typical storage buffer (~20 mL) was prepared by mixing 10 mL 75 mM Tris pH7 buffer, 200 mg BSA, 150 uL 5% NaN$_3$, 10 mL glycerol, and 10 mg lysine.

TABLE 7

| Labeled GAM IgG antibody solution | Compound No. | Labeling condition | | | | Amount of storage buffer (uL) |
|---|---|---|---|---|---|---|
| | | Amount of GAM IgG (µg) | Antibody concentration in reaction (mg/mL) | Amount of dye (nmoles) | Antibody-to-dye ratio (ug/nmole) | |
| #16 | 45  | 50  | 1   | 3.8 | 13.2:1 | 300 |
| #17 | 45  | 100 | 0.5 | 3.8 | 26.3:1 | 300 |
| #18 | 45  | 50  | 1   | 5.6 | 8.9:1  | 300 |
| #19 | 45  | 100 | 0.5 | 5.6 | 17.9:1 | 300 |
| #20 | 45  | 50  | 1   | 7.5 | 6.7:1  | 300 |
| #21 | 45  | 100 | 0.5 | 7.5 | 13.3:1 | 300 |
| #22 | 45  | 50  | 1   | 9.4 | 5.3:1  | 300 |
| #23 | 45  | 100 | 0.5 | 9.4 | 10.6:1 | 300 |
| #24 | 127 | 50  | 1   | 3.8 | 13.2:1 | 300 |
| #25 | 127 | 100 | 0.5 | 3.8 | 26.3:1 | 300 |
| #26 | 127 | 50  | 1   | 5.6 | 8.9:1  | 300 |
| #27 | 127 | 100 | 0.5 | 5.6 | 17.9:1 | 300 |
| #28 | 127 | 50  | 1   | 7.5 | 6.7:1  | 300 |
| #29 | 127 | 100 | 0.5 | 7.5 | 13.3:1 | 300 |
| #30 | 127 | 50  | 1   | 9.4 | 5.3:1  | 300 |
| #31 | 127 | 100 | 0.5 | 9.4 | 10.6:1 | 300 |

Figure 3:
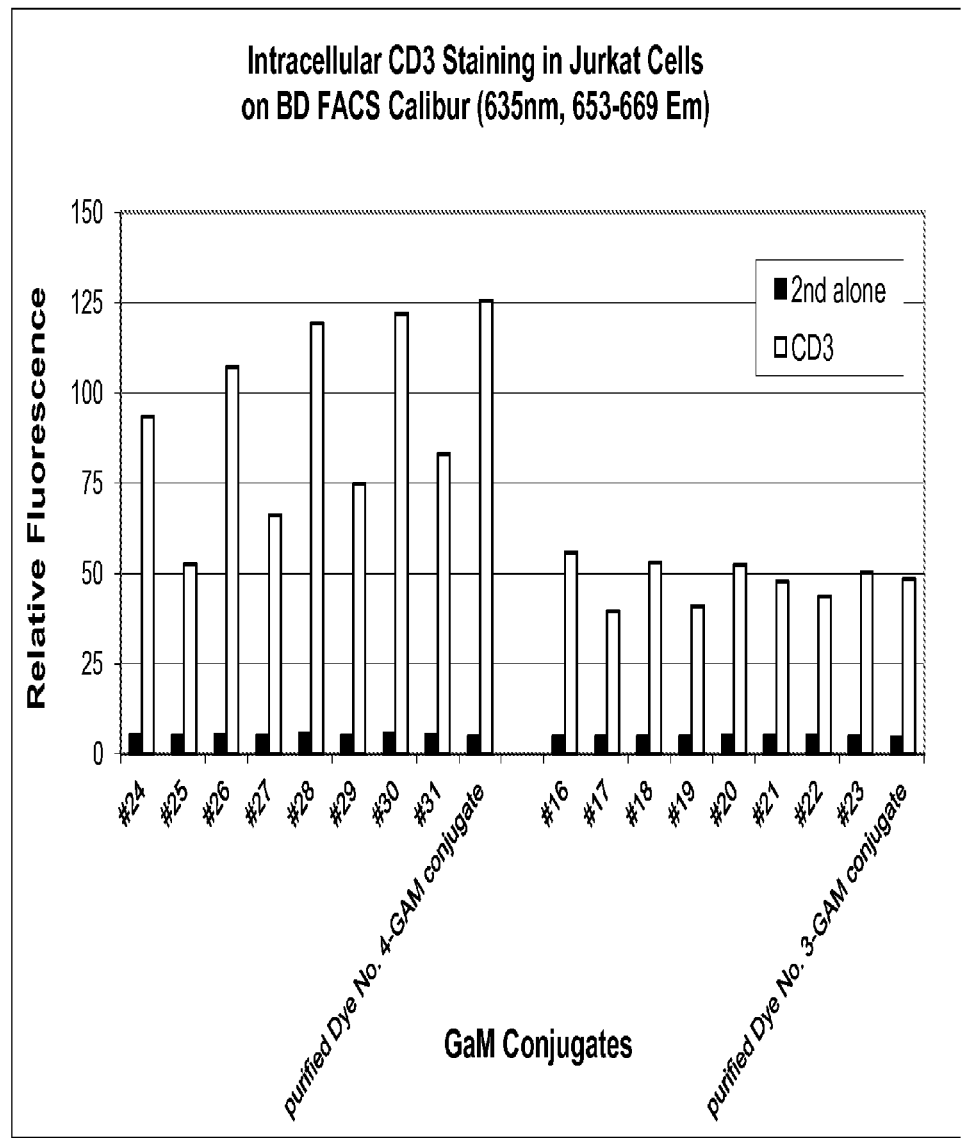
FIG. 3 shows the results of a flow cytometry analysis of cells stained with secondary antibodies labeled according to methods of the invention.

Purified GAM IgG conjugates to either Compound No. 54 or Compound No. 127 were also prepared for cell staining as a control. The purified antibody conjugates were prepared using standard antibody conjugation method as described in Example 2. Purified conjugates with Compound No. 54 are referred to as "purified Dye No. 3-GAM" in FIG. 3. Purified conjugates with Compound No. 127 are referred to as "purified Dye No. 4-GAM" in FIG. 4.

Cell staining experiments were conducted similarly to Example 1. Stained samples were analyzed on BD FACS Calibur using 635 nm excitation and FL4 detection channel. Relative fluorescence signals were plotted in FIG. 3. The data show that cell immunostaining according to the invention and that according to the conventional method using a purified antibody conjugate produced comparable results.

Example 4: Analysis of Cells Stained with Secondary Antibody Labeled with Compound No. 128

This example describes labeling of an antibody with a far-red fluorescent sulfonated xanthene dye (Compound No. 128), and the use of such antibodies for intracellular staining and flow cytometry analysis. Compound No. 128, absorbs light at about 630 nm and emits light at about 650 nm. The structure of Compound No. 128 is as follows:

Compound No. 128

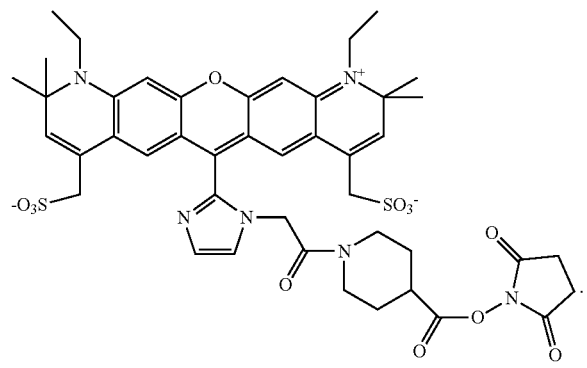

Solutions of mouse anti-human CD3 antibody (BD Biosciences) labeled with Compound No. 128 were prepared using different dye-to-antibody ratios and different antibody concentrations in a reaction buffer comprising 10 mM Tris and 50 mM $NaHCO_3$ (pH 8.3). Detailed labeling reaction conditions are listed in Table 8 below. Labeling reactions were carried out as described in Example 1. Labeled antibody solutions were used directly in cell staining.

TABLE 8

| Labeled mouse anti-human CD3 antibody solution | Labeling condition ||||
|---|---|---|---|---|
| | Amount of antibody (µg) | Antibody concentration in reaction (mg/mL) | Amount of dye (nmoles) | Antibody-to-dye ratio (ug/nmole) |
| #32 | 100 | 0.5 | 5.6 | 17.8:1 |
| #33 | 50 | 0.5 | 5.6 | 8.9:1 |
| #34 | 20 | 0.5 | 2.8 | 7.2:1 |
| #35 | 20 | 0.5 | 1.4 | 14.3:1 |
| #36 | 5 | 0.5 | 1.4 | 3.6:1 |

Figure 4:
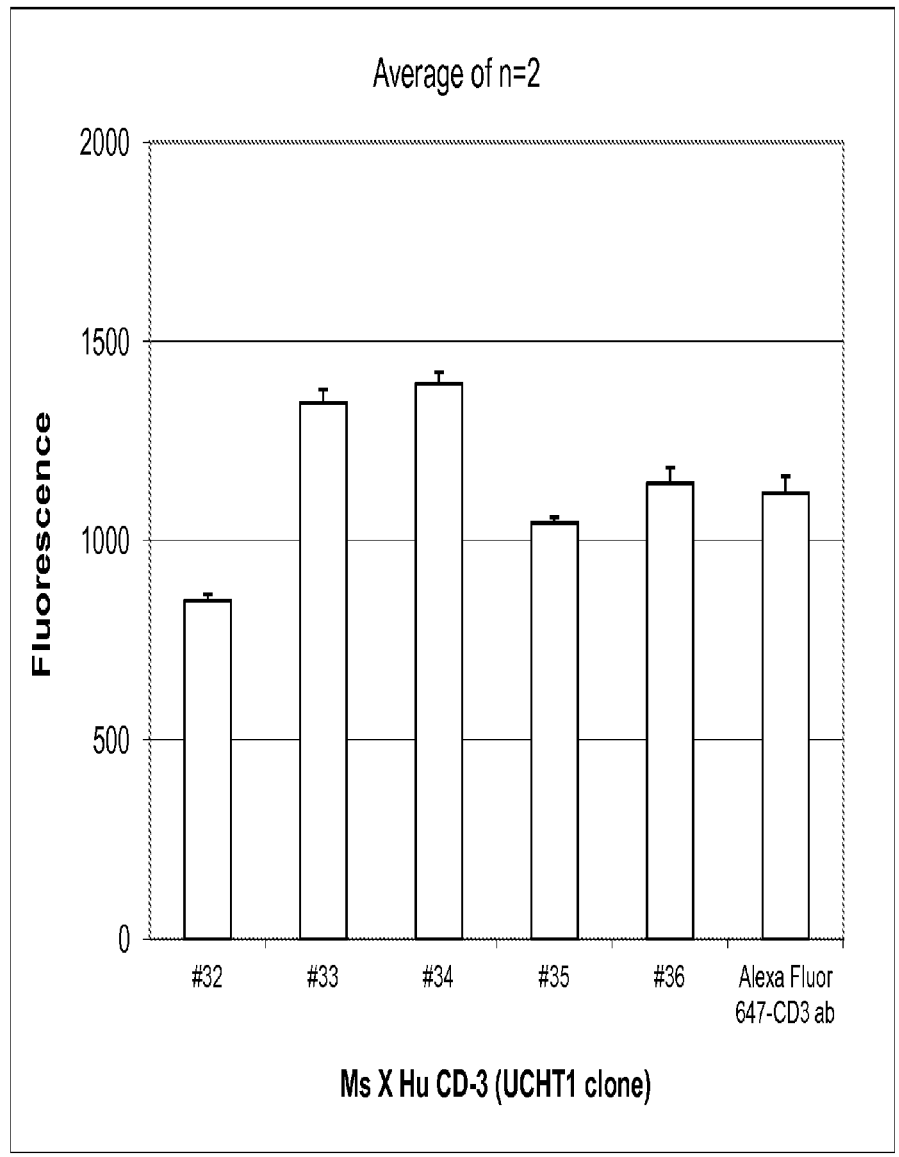
FIG. 4 shows the results of a flow cytometry analysis of cells stained with primary antibodies labeled according to methods of the invention.

One million Jurkat cells per sample were fixed, permeabilized, and stained with 0.25 µg of one of the labeled mouse anti-human CD3 (BD Biosciences) conjugates prepared according to Table 8. For comparison, commercially available mouse anti-human CD3 antibody pre-labeled with spectrally similar Alexa Fluor 647 (BD Biosciences) was also used to stain the cells. About 10,000 cells from each sample were analyzed on a BD FACS Calibur flow cytometer using 635 nm excitation and fluorescence was detected in the FL4 channel Signal represents average fluorescence intensity of the stained cells (FIG. 4). The bars in FIG. 4 represent the average of the fluorescence intensity of duplicate samples. The results show that cells stained with antibodies labeled according to the invention show fluorescence signals comparable to the commercially available control, and the cell staining intensity is substantially independent of the conditions under which the labeled antibodies are prepared, such as the antibody-to-dye ratio and antibody concentration.

Example 5: Analysis of Cells Stained with Primary Antibody Labeled with Compound No. 42

This example describes labeling of an anti-β-tubulin antibody with a far-red fluorescent sulfonated xanthene dye (Compound No. 42), and the use of such antibodies for intracellular staining and flow cytometry analysis. Mouse anti-β-tubulin IgM primary antibody (BD Biosciences) was labeled with Compound No. 42 according to the conditions listed in Table 9 below. Reaction procedure and storage buffer preparation are as described in Example 1.

TABLE 9

| Labeled b-tubulin IgM antibody solution | Labeling condition |||| |
|---|---|---|---|---|---|
| | Amount of GAM IgG (µg) | Antibody concentration in reaction (mg/mL) | Amount of dye (nmoles) | Antibody-to-dye ratio (ug/nmole) | Amount of storage buffer (uL) |
| #37 | 10 | 0.5 | 0.56 | 17.9:1 | 60 |
| #38 | 10 | 0.5 | 1.3 | 7.7:1 | 60 |
| #39 | 10 | 0.5 | 1.4 | 7.2:1 | 60 |
| #40 | 10 | 0.5 | 0.75 | 13.4:1 | 60 |
| #41 | 10 | 0.5 | 1.5 | 6.7:1 | 60 |
| #42 | 10 | 0.5 | 1.88 | 5.3:1 | 60 |

Figure 5:
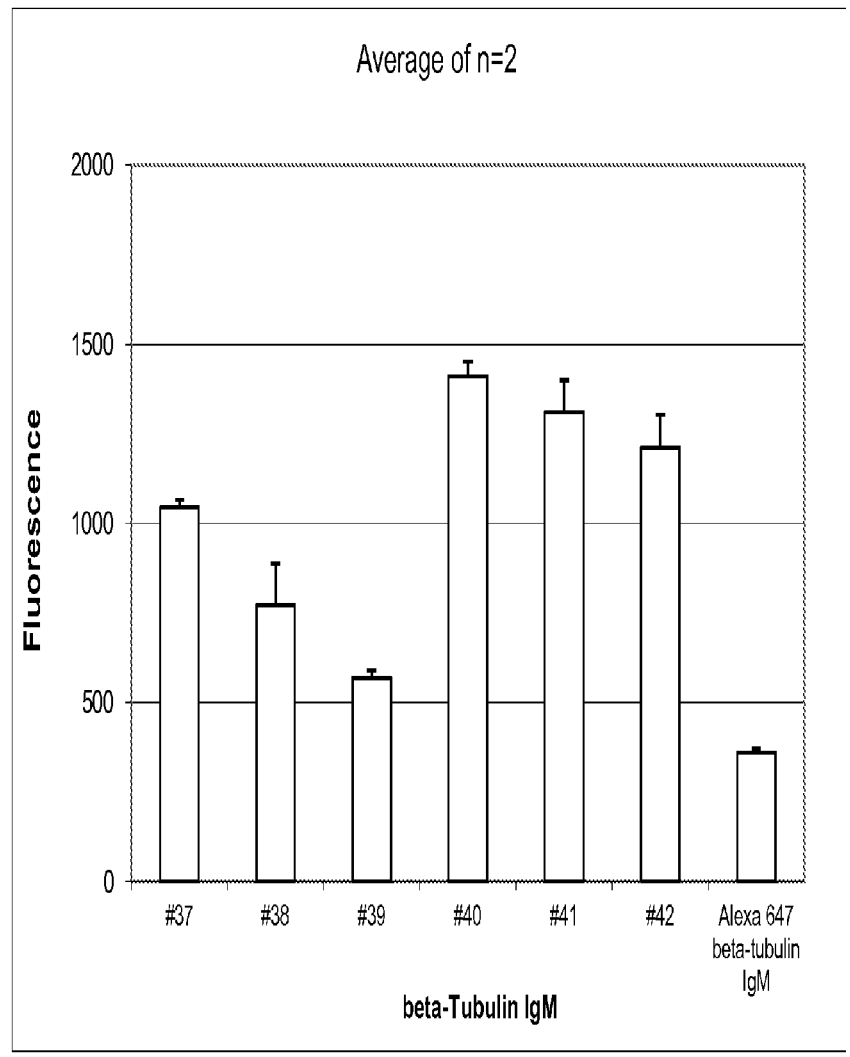
FIG. 5 shows the results of a flow cytometry analysis of cells stained with primary antibodies labeled according to methods of the invention.

One million Jurkat cells per sample were stained with 0.25 µg of one of the labeled anti-β-tubulin IgM antibodies prepared according to Table 9. For comparison, commercially available anti-β-tubulin IgM pre-labeled with spectrally similar Alexa Fluor 647 (BD Biosciences) was also used to stain the cells. About 10,000 cells from each sample were analyzed on a BD FACS Calibur flow cytometer using 635 nm excitation and fluorescence was detected in the FL4 channel Signal represents average fluorescence intensity of the stained cells (FIG. 5). The results show that cells stained with antibodies labeled according to the invention show improved fluorescence signal over the commercially available control, and the cell staining intensity is substantially independent of the conditions under which the labeled antibodies are prepared, such as the antibody-to-dye ratio and antibody concentration.

Example 6: Microscopy Analysis of Cells Stained with Primary Antibody Labeled with Cmpd. No. 42

This examples describes the use of antibodies as prepared in Example 5 for cell staining of β-tubulin and analysis under a microscope, as compared to a commercially available antibody. Hela cells were cultured on glass coverslips, fixed with formaldehyde, permeabilized and blocked with 2% serum/PBS (blocking buffer). Cells were subsequently stained with solution #37 of Table 9 or with a purified mouse β-tubulin IgM primary antibody labeled with Alexa Fluor®

Figure 6:
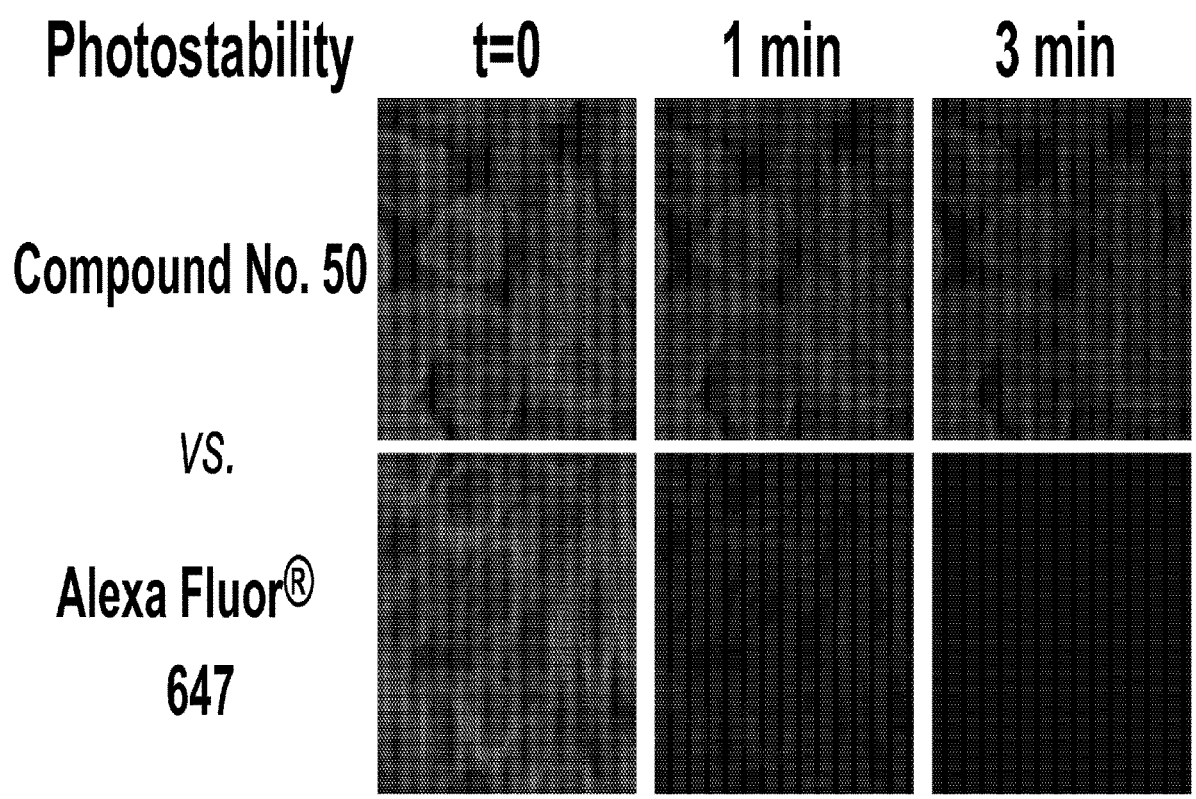
FIG. 6 shows images from a microscopic analysis of cells stained with primary antibodies labeled according to methods of the invention.

647 purchased from BD Biosciences. Each coverslip was labeled with 1 μg antibody conjugates in 200 uL blocking buffer for 1 hr. Cells were extensively washed with 1×PBS and mounted onto glass slides. Images were taken on an Olympus mercury arc lamp microscope immediately after staining (t=0) and at 1 minute and 3 minutes after staining. Example images are shown in FIG. 6. The results show that cells stained with antibody conjugate of this invention are comparable to the purified IgM primary antibody labeled with Alexa Fluor® 647. Cells stained with Compound No. 42 showed comparable specific staining and intensity compared to cells stained with commercially purchased B-tubulin antibody labeled with Alexa Fluor® 647. In addition, the labeled antibodies of the invention demonstrate an improved resistance to photobleaching compared to the commercially available control.

Example 7: Multi-Color Imaging of Cells Labeled with Compound No. 42

Figure 7:
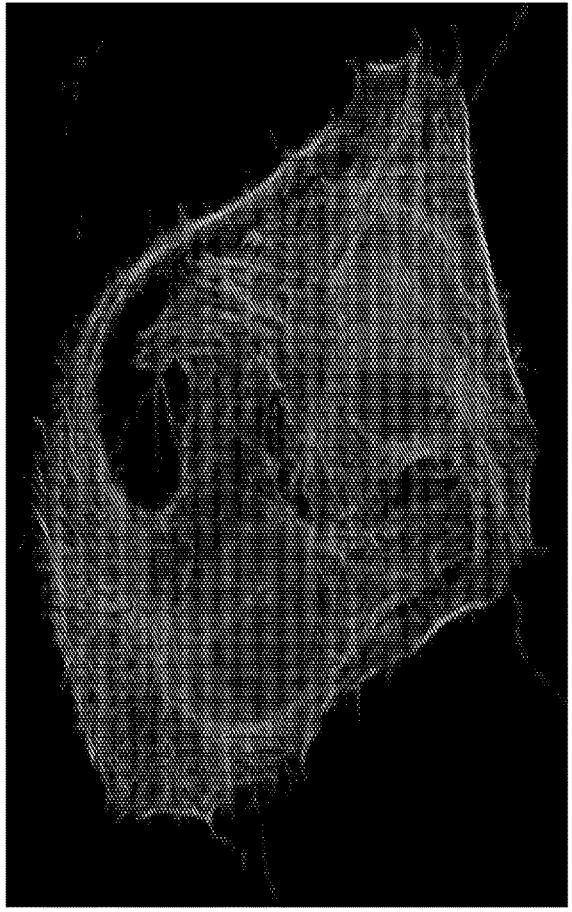
FIG. 7 shows images from a microscopic analysis of cells stained with primary antibodies labeled according to methods of the invention, in addition to other stains.
Figure 7:

Hela cells were cultured on glass coverslips, fixed and stained with Compound No. 42 conjugated with anti-β-tubulin IgM as in Example 5, CF488A-phalloidin, and DAPI. The cells were stained with 1 μg IgM antibody conjugate in 200 uL serum blocking buffer. Stainings with CF488A-phalloidin and DAPI were carried according to the manufacture's product information sheets (Biotium). The images were taken on a Zeiss LSM 510 Meta Confocal system. Example images are shown in FIG. 7 in greyscale. The images show the dye-antibody labeling technology is compatible with multi-color imaging with other fluorescent probes.

Example 8: Preparation of Aminooxy-Functionalized R-PE

A R-phycoerythrin (R-PE) suspension containing 22.4 mg of R-PE (ProZyme, Hayward, Calif.) was dialyzed against PBS buffer to remove ammonium sulfate and then concentrated to about 7 mg/mL (~3.2 mL) via ultramembrane filtration. The resulting R-PE solution was combined with 0.32 mL of a pH 8.4 reaction buffer comprising 0.5 M sodium bicarbonate and 0.1 M Tris and 78 uL(0.46 umole) of 4-formylbenzoic acid succinimidyl ester in DMF at 6 mM (prepared by mixing equal amount of 4-formylbenzoic acid, triethylamine and O-succinimido-N,N,N',N'-tetramethyluronium tetrafluoroborate (TSTU) and incubing the combined solution for 15 minutes). The combined solution was incubated at room temperature for about 1 hour. The aldehyde-functionalized R-PE was purified with a G-25 column eluting with PBS. The purified protein was concentrated to about 6 mg/mL The functionalized R-PE (3.4 mL, 85 nmoles), 300 uL (8.4 umoles) of 1,3-bis(aminooxy)propane dihydrochloride dissolved in water and 370 uL of a pH 4 phosphate buffer comprising 100 mM aniline were mixed. The combined solution was incubated at room temperature for about 1 hour. The resulting solution was run through a G-25 size exclusion column eluting with PBS buffer. The purified aminooxy-functioned R-PE was concentrated to about 5 mg/mL.

Example 9. Preparation of Goat Anti-Mouse IgG Labeled with R-PE

Goat anti-mouse (50 μg, 50 uL at 1 mg/mL), 5 uL of pH 8.4 reaction buffer comprising 0.5 M sodium bicarbonate and 100 mM Tris, and 4-formylbenzoic acid succinimidyl ester prepared above in Example 8 (1.7 nmoles) in DMF were combined and then incubated for about 30 minutes. About 25 uL of pH 3.7 phosphate buffer comprising 100 mM aniline and about 150 μg of the aminooxy-R-PE from Example 8 are combined and incubated at room temperature for about 1 hour. The resulting solution was used for cell staining without further purification (Example 10).

Figure 8:
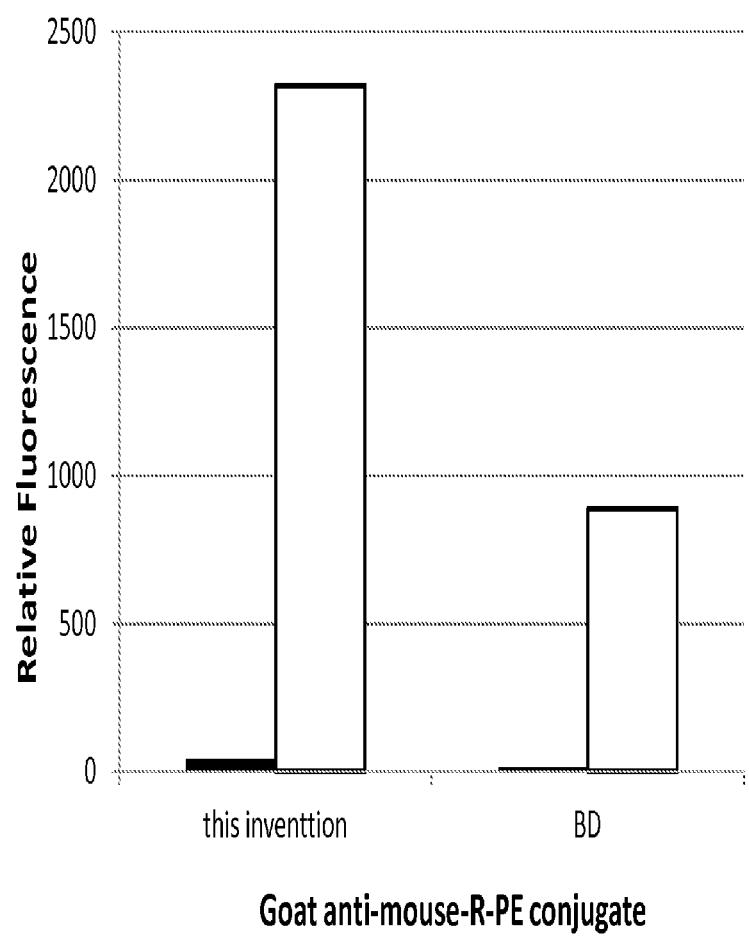
FIG. 8 shows the results of a flow cytometry analysis of cells stained with primary antibodies labeled according to methods of the invention.

Example 10: Flow Cytometry Analysis of Intracellular Staining with R-PE Secondary Antibody Conjugates Prepared Under Various Conjugation Conditions Approximately one million Jurkat cells per sample were stained with 0.25 μg mouse anti-human CD3 (BD Biosciences) followed by 1 μg of R-PE goat anti-mouse IgG conjugate. The fluorescence of 10,000 cells from each sample was analyzed on a BD FACSCalibur flow cytometer in the FL2 channel (488 nm excitation laser, 564-606 nm band-pass emission filter). Signal represents average fluorescence intensity from cells stained with CD3 and goat anti-mouse IgG. Noise represents the average intensity from cells stained with only goat anti-mouse secondary conjugates, which reflects the level of non-specific secondary antibody binding. The data were plotted in FIG. 8. The results show that cells stained with antibodies labeled according to the invention show high specific fluorescence signal and low non-specific antibody binding.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for preparing a labeled protein comprising:
   (a) providing an amine-reactive dye comprising an activated ester;
   (b) providing a solution comprising a target protein and a Tris buffer, wherein the target protein is an antibody;
   (c) combining the amine-reactive dye with the solution to form a combined solution wherein the combined solution comprises the Tris buffer at a concentration from about 10 mM to about 100 mM; and
   (d) allowing the combined solution to react for about 3 hours or less, such that the target protein is conjugated to the amine-reactive dye, thereby producing the labeled protein.

2. The method of claim 1, wherein more than 90% of the target protein reacts to form the labeled protein.

3. The method of claim 1, wherein more than 95% of the target protein reacts to form the labeled protein.

4. The method of claim 1, wherein the combined solution is allowed to react for 30 minutes or less.

5. The method of claim 1, wherein the target protein is a primary antibody or a secondary antibody.

6. The method of claim 1, wherein the activated ester is N-hydroxy succinimidyl ester, N-hydroxy sulfosuccinimidyl ester, or p-sulfo-tetrafluorophenol ester.

7. The method of claim 1, wherein the amine-reactive dye is a CF dye, an Alexa Fluor dye, a DyLight Dye, a Cy dye, an IRDye, a HiLyte dye, a sulfonated or pegylated coumarin dye, a sulfonated or pegylated xanthene dye, a sulfonated or pegylated cyanine dye, or a sulfonated or pegylated pyrene dye.

8. The method of claim 1, wherein the amine-reactive dye is selected from the group consisting of:

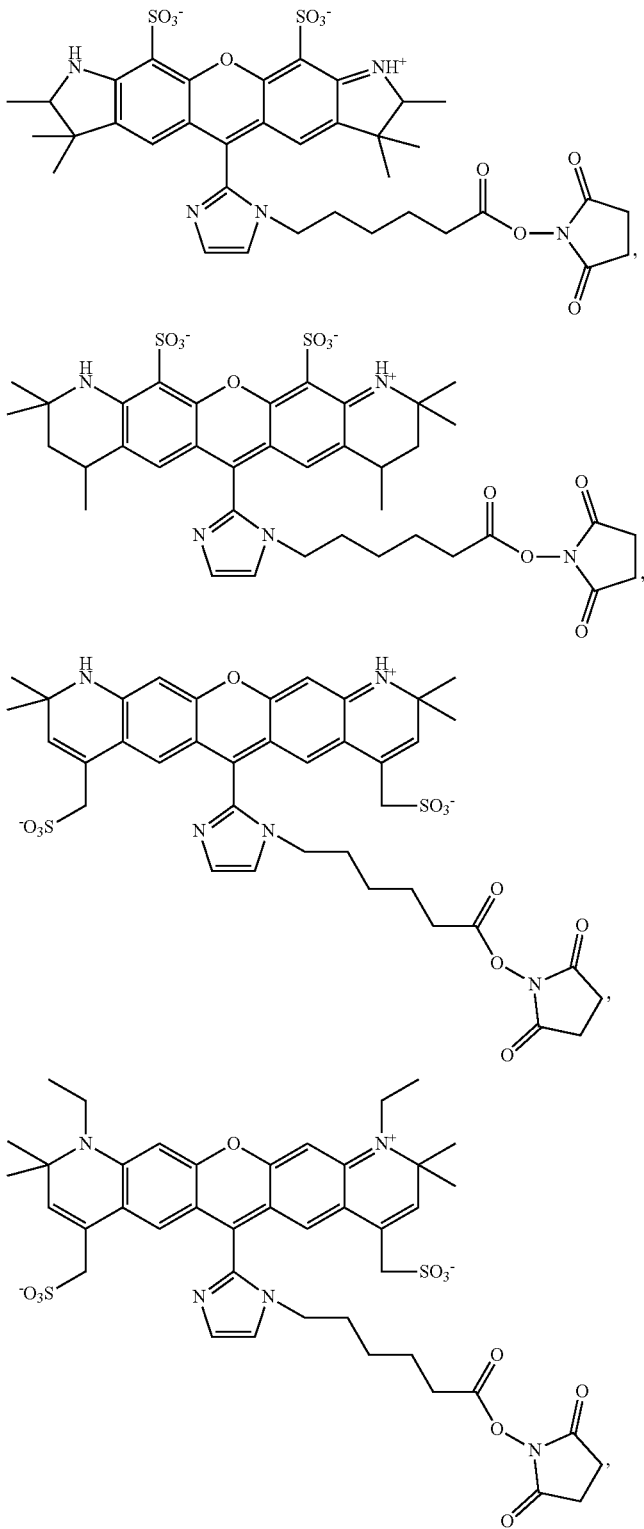

-continued
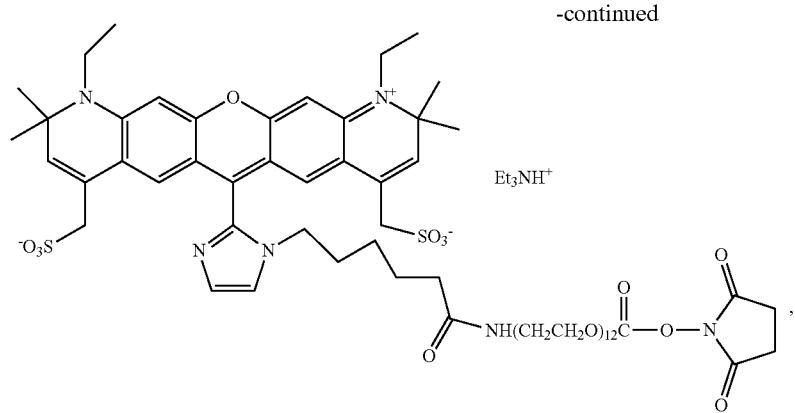
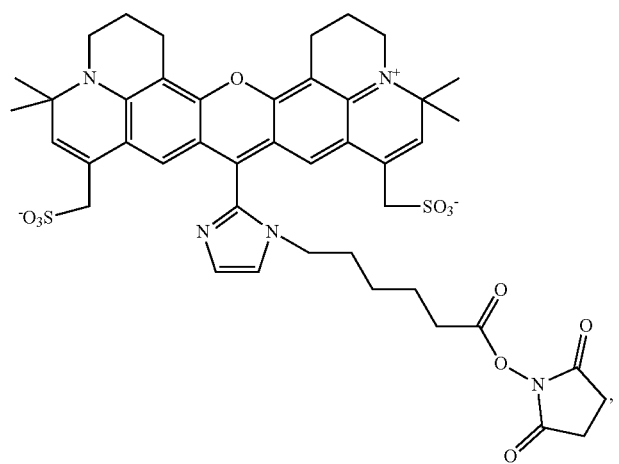
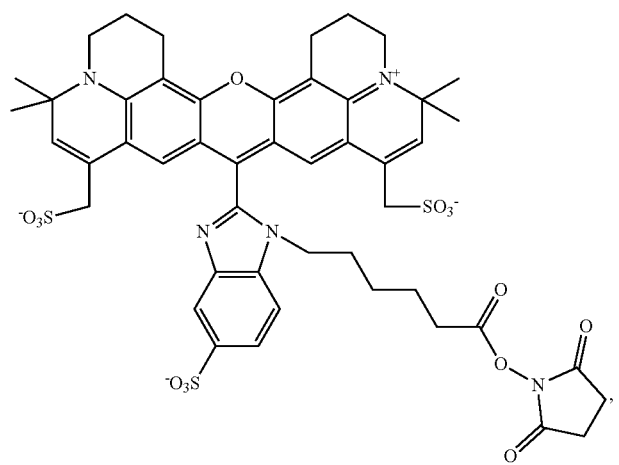

-continued
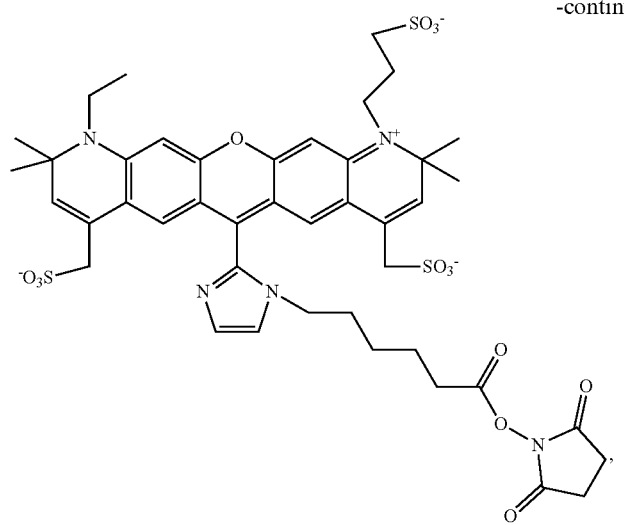
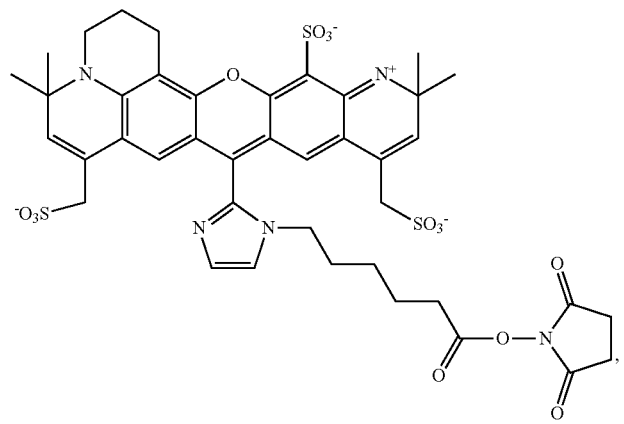
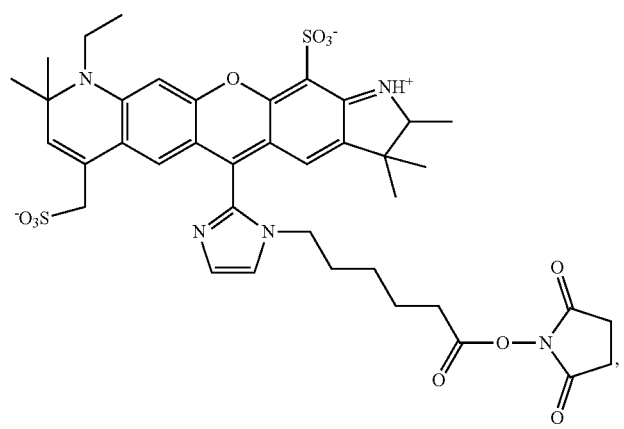

-continued
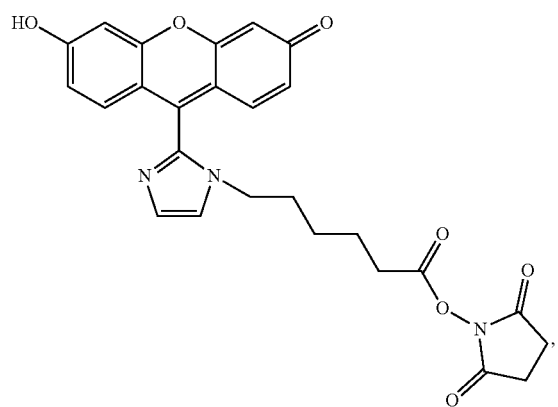
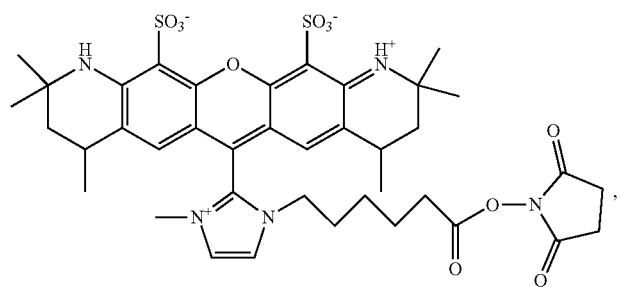
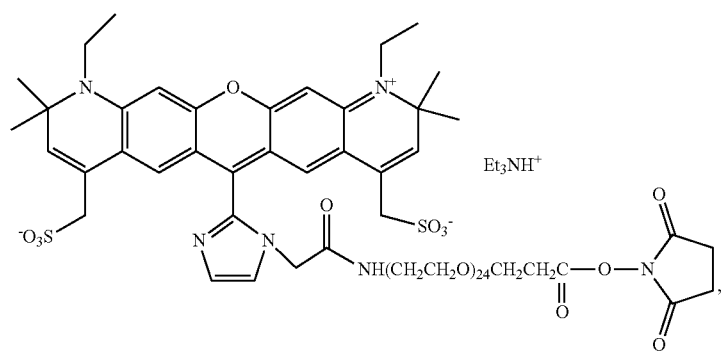
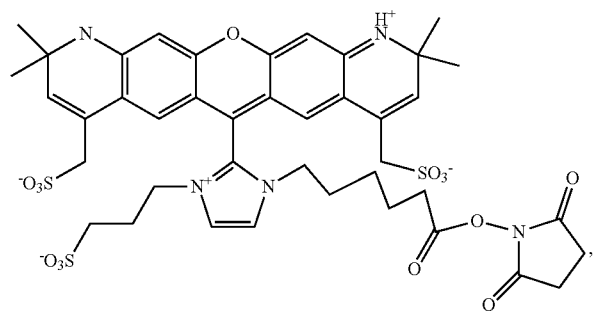

-continued
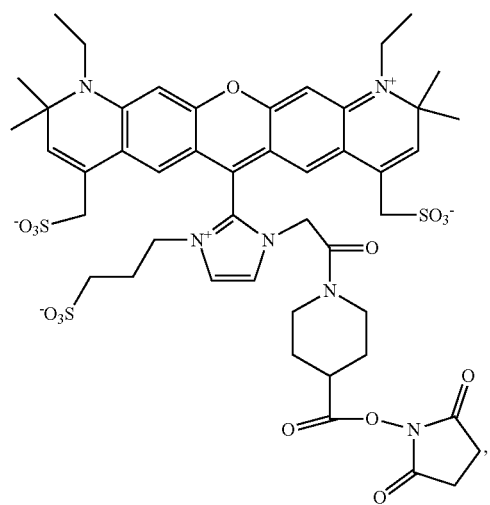
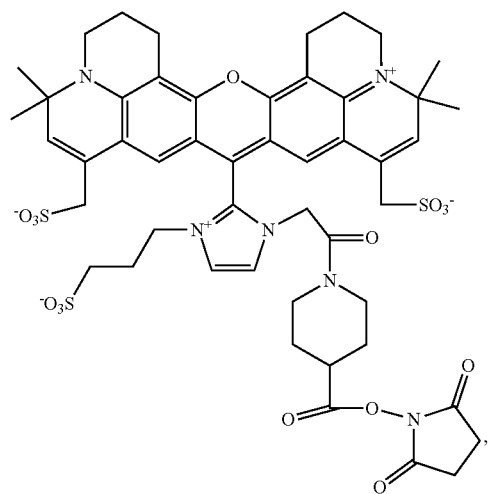
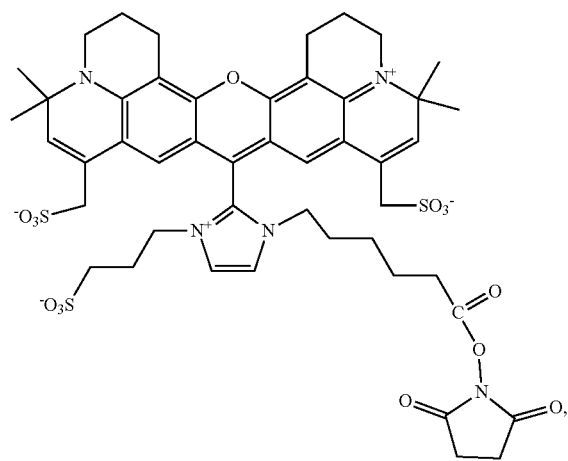

-continued
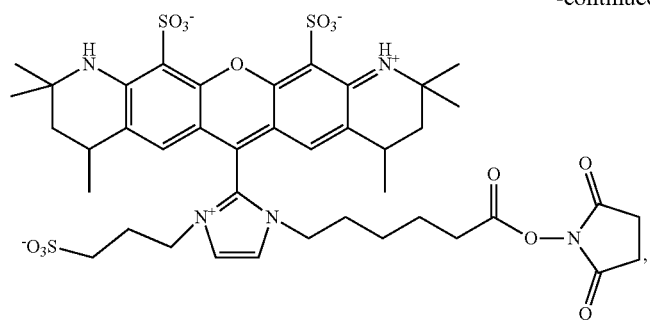
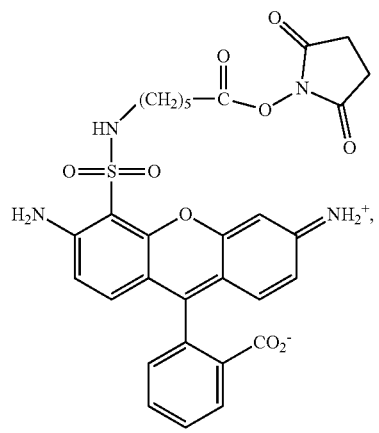
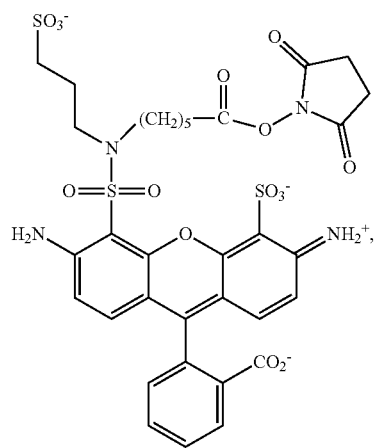
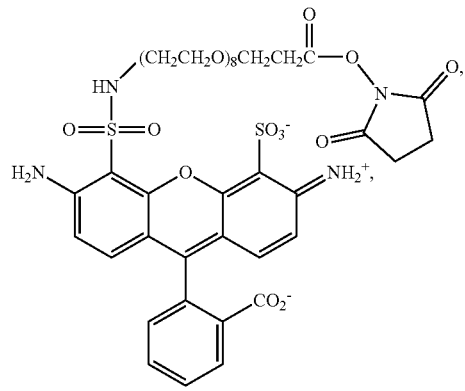

-continued
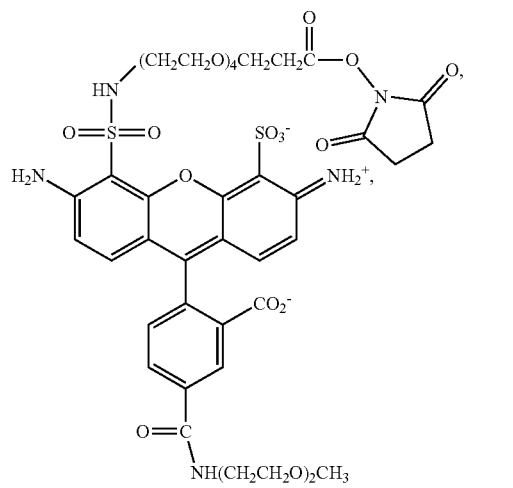
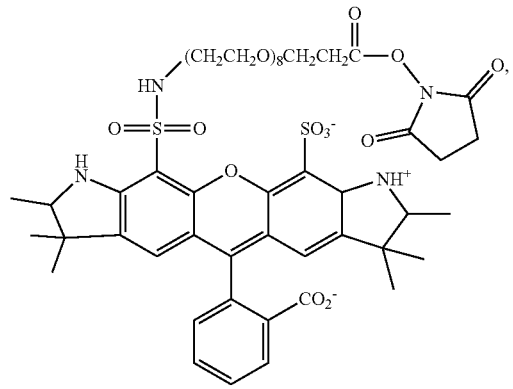
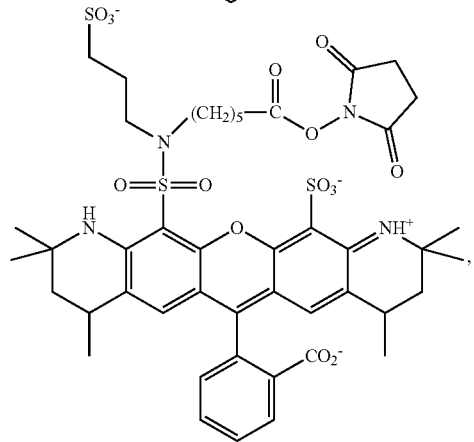
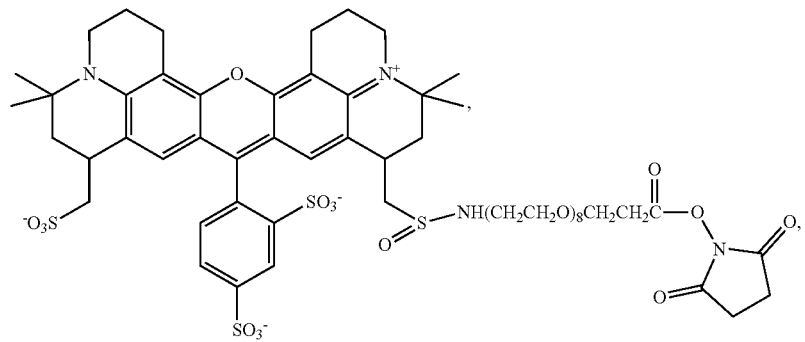

-continued
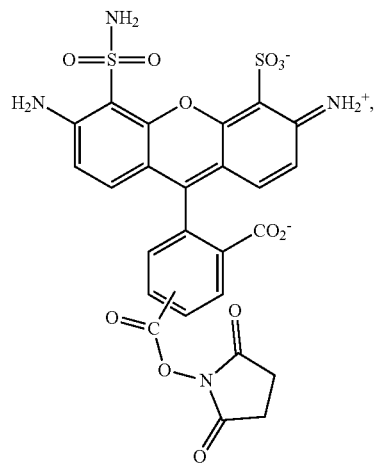
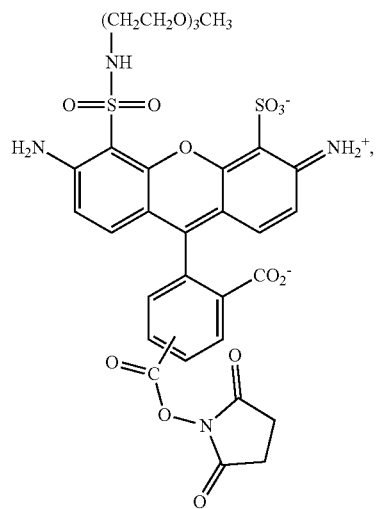
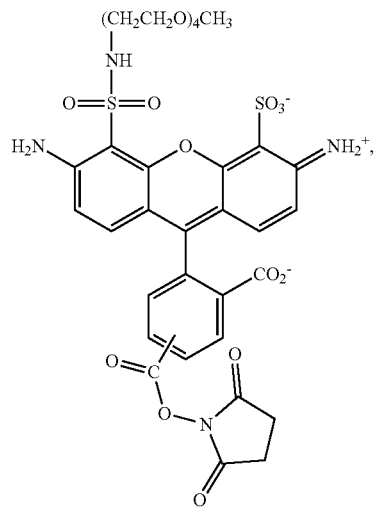

-continued
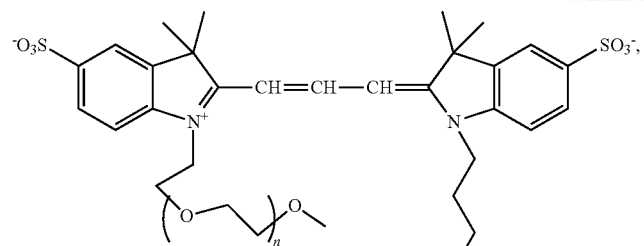
n = 23
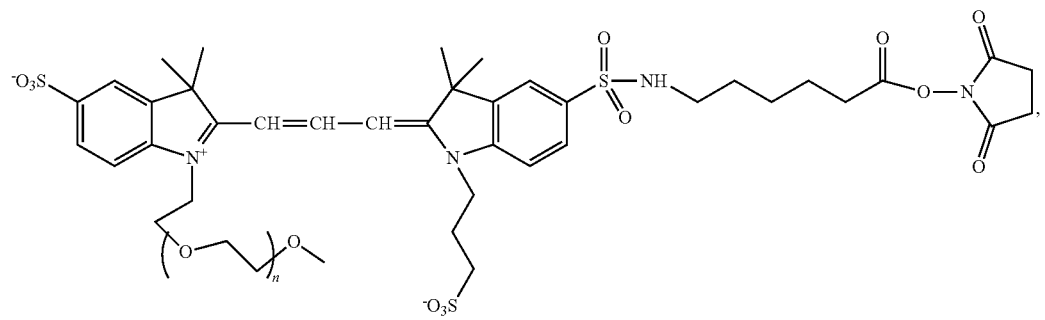
n = 23
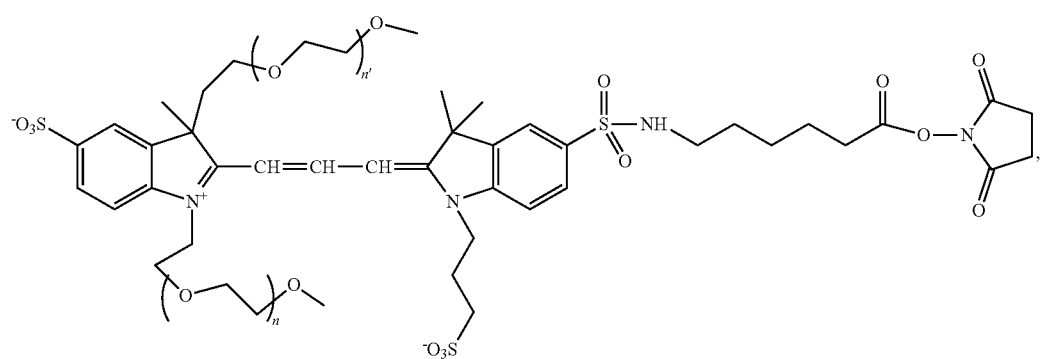
n = 19
n' = 19

-continued
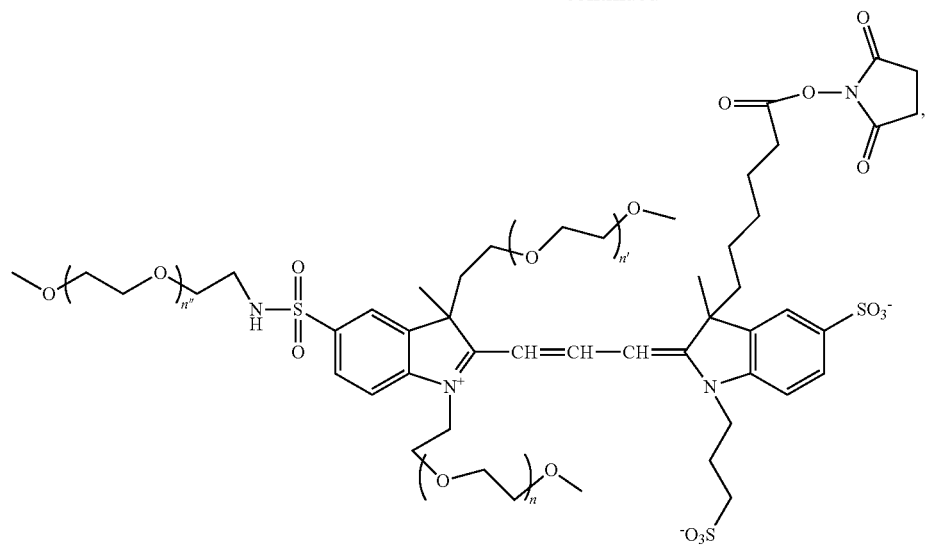
n = n'
n″ = 11
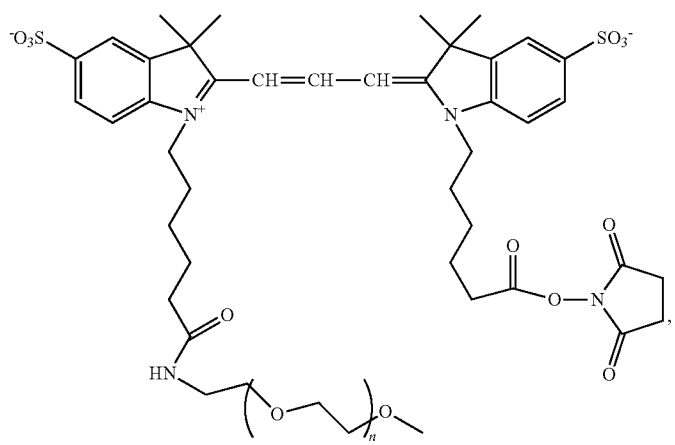
n = 47
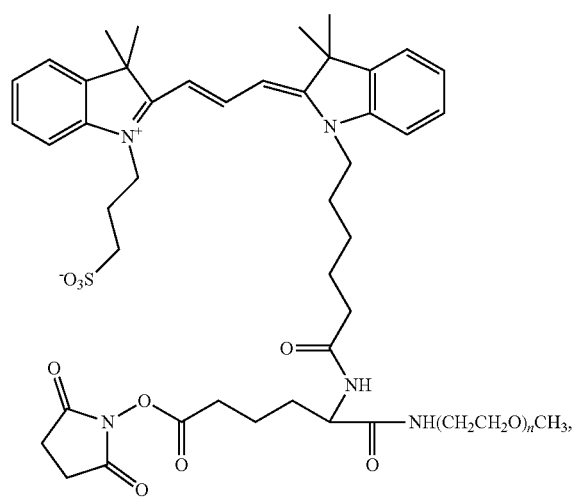
n' = 12

-continued
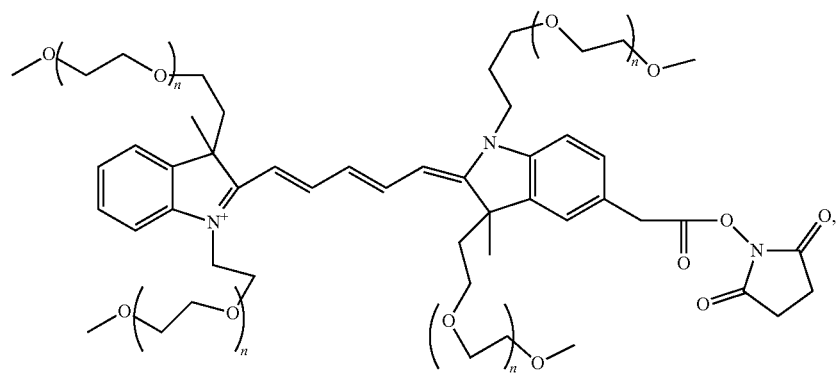
n = 11
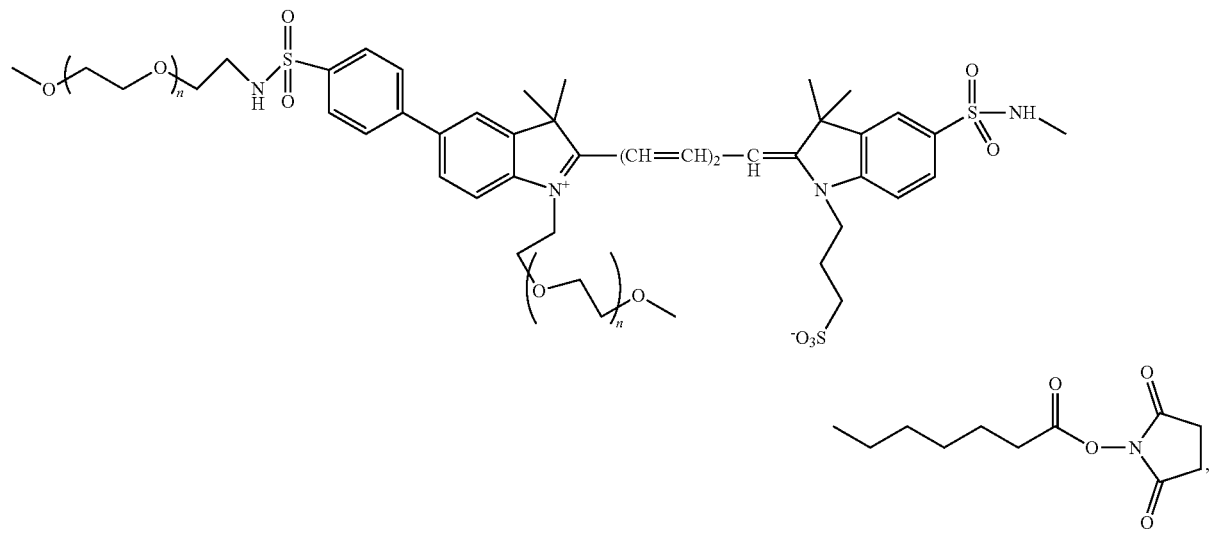
n = 23
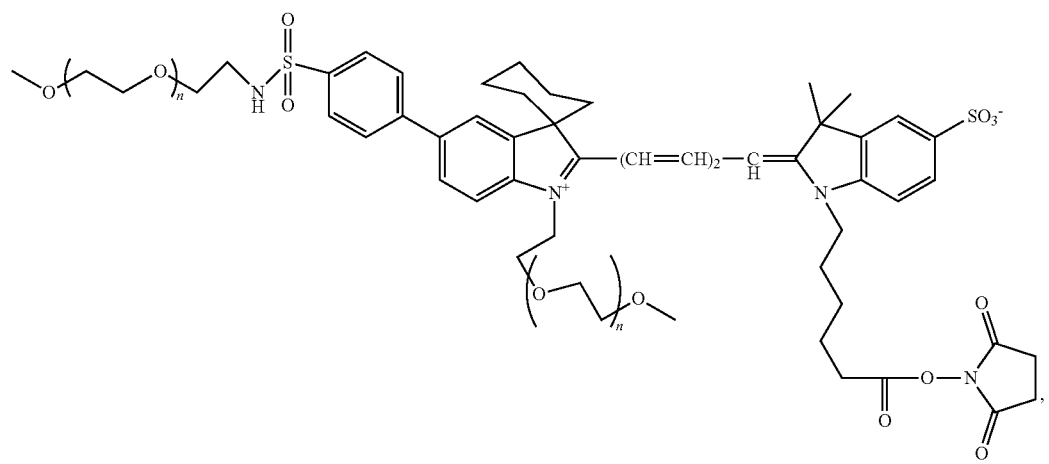
n = 23

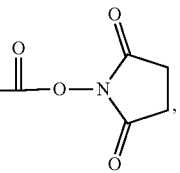
-continued
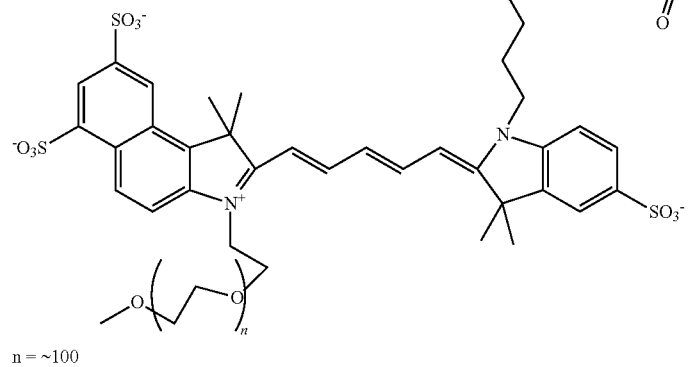
n = ~100
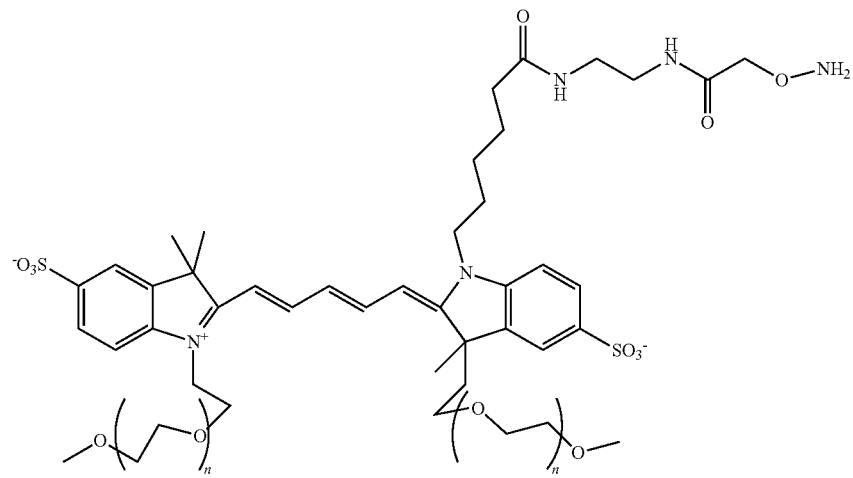
n = 23
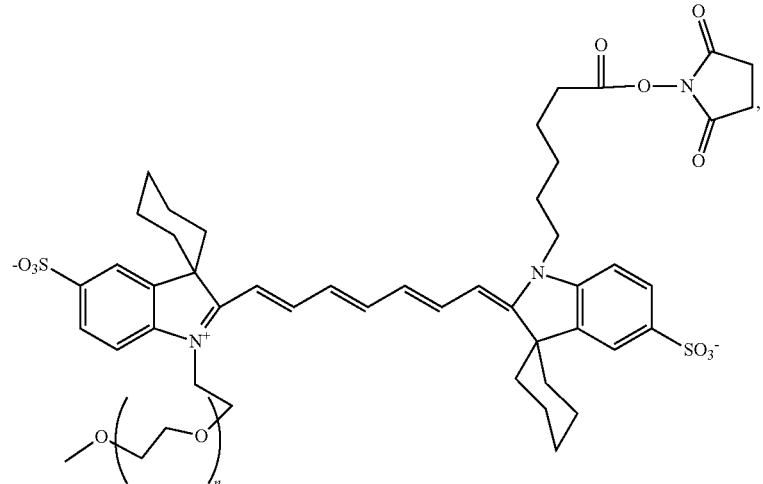
n = 23

-continued
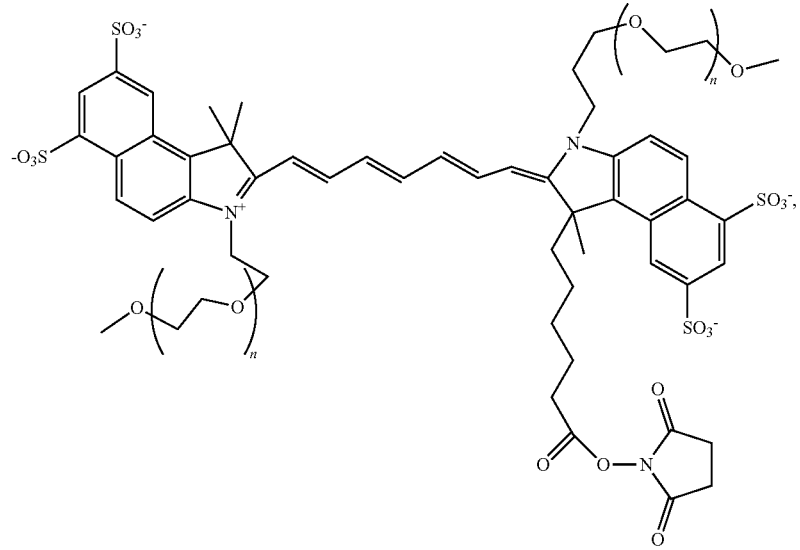
n = 23
n' = 11
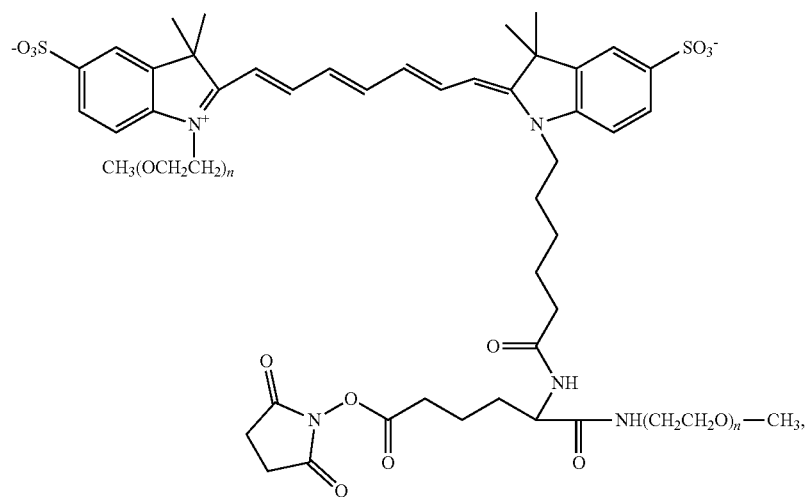
n = 12
n' = 24
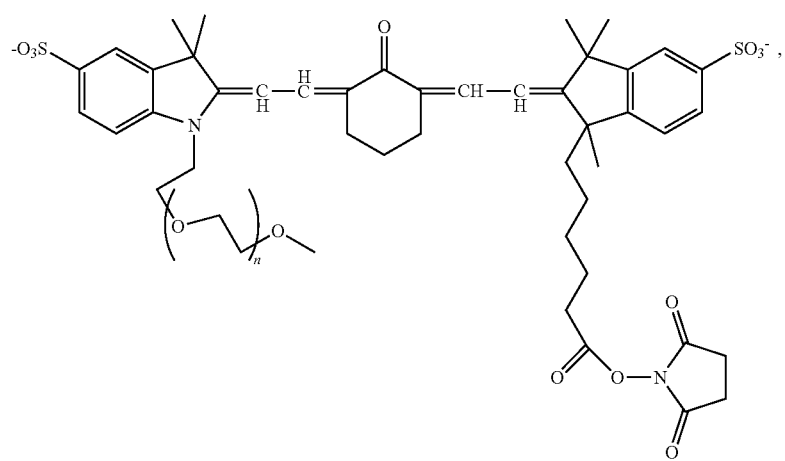
n = 23

-continued
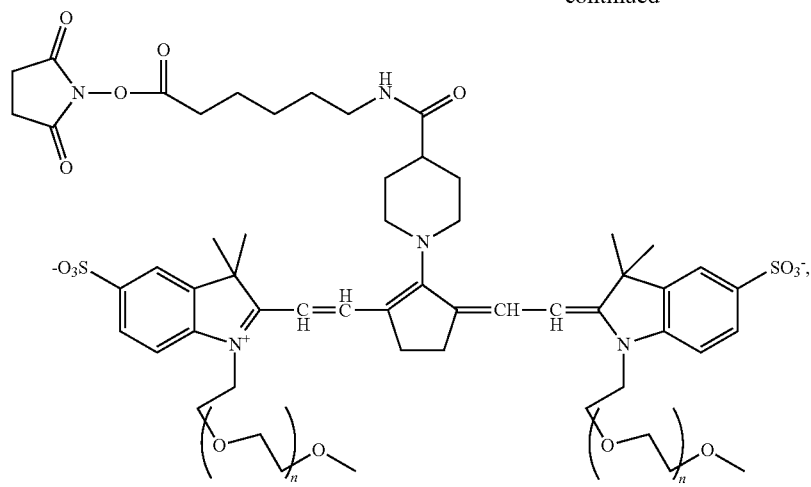
n = 24
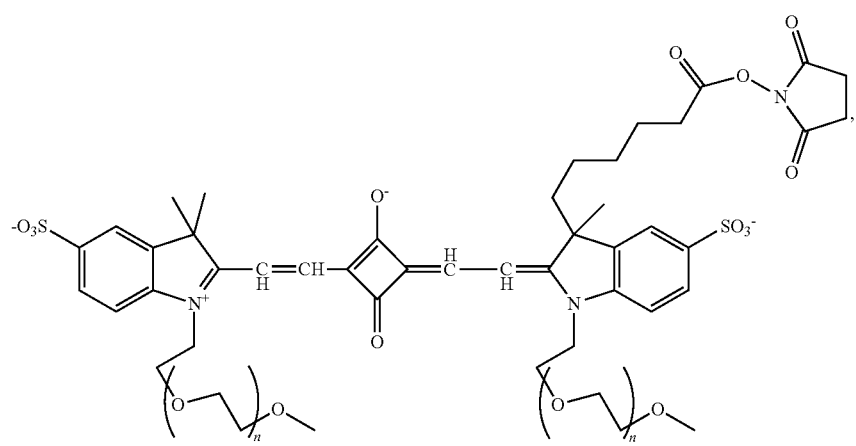
n = 23
n' = 12
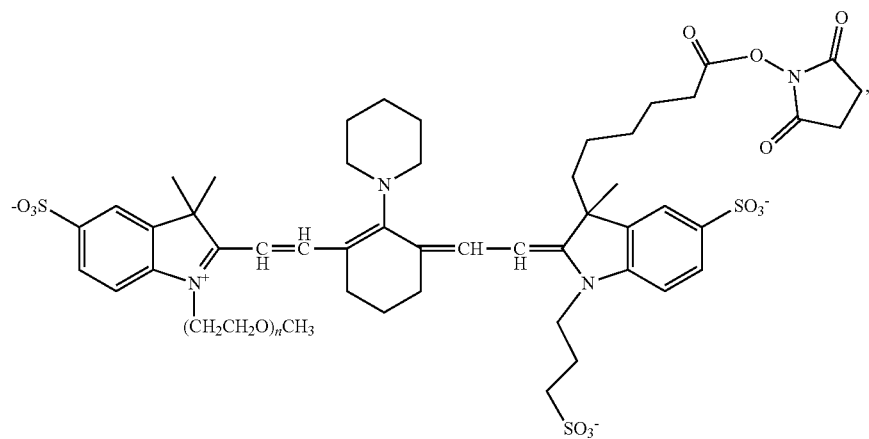
n = 24

-continued
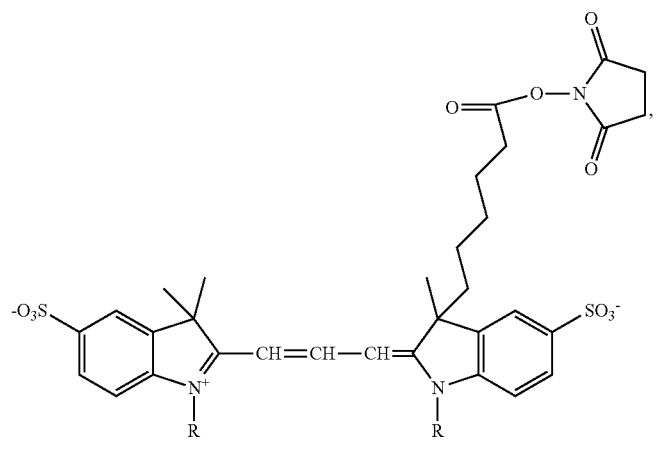
-R = -(CH₂)₅CONH(CH₂CH₂O)₂₄CH₃
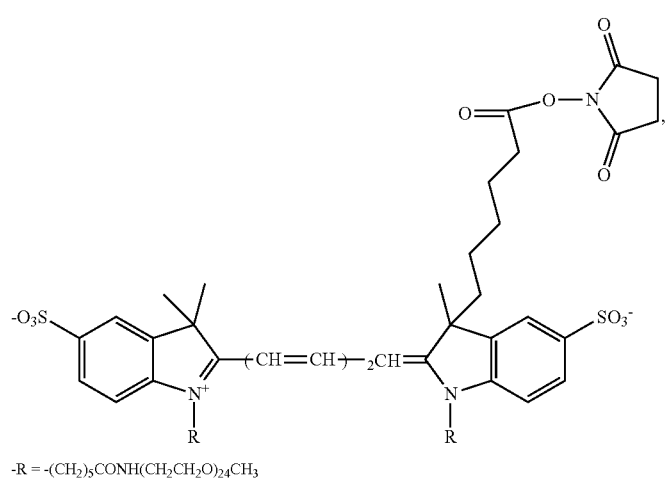
-R = -(CH₂)₅CONH(CH₂CH₂O)₂₄CH₃
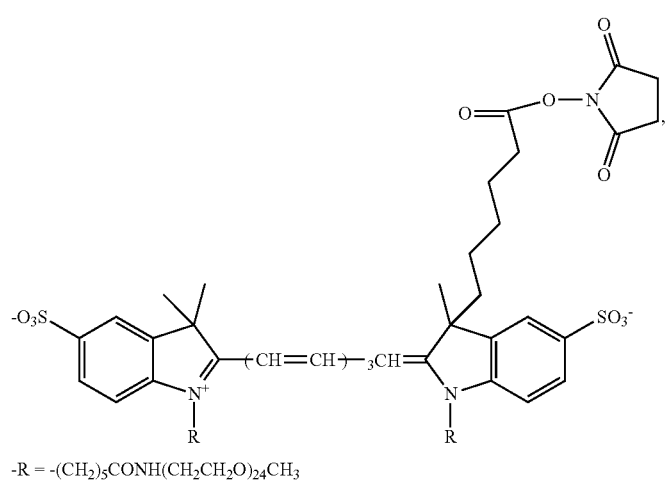
-R = -(CH₂)₅CONH(CH₂CH₂O)₂₄CH₃

-continued
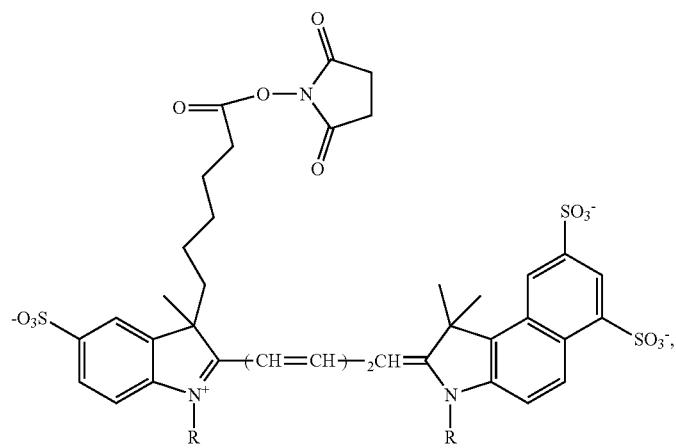
-R = -(CH₂)₅CONH(CH₂CH₂O)₂₄CH₃
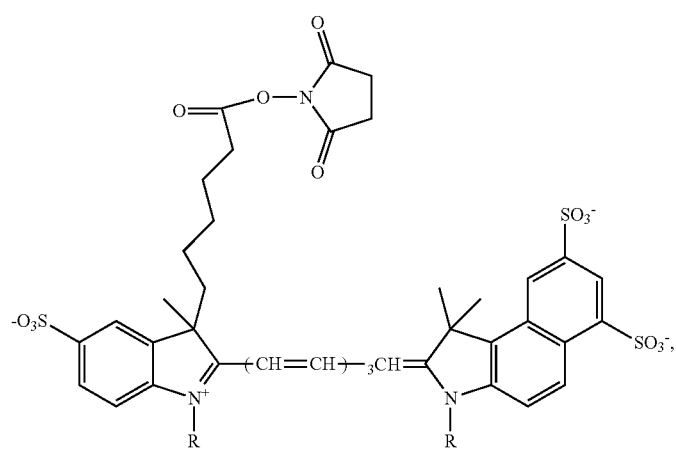
-R = -(CH₂)₅CONH(CH₂CH₂O)₂₄CH₃
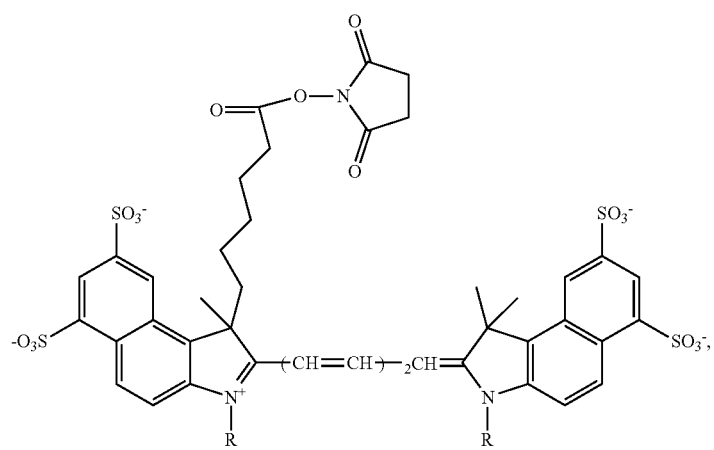
-R = -(CH₂)₅CONH(CH₂CH₂O)₂₄CH₃

-continued
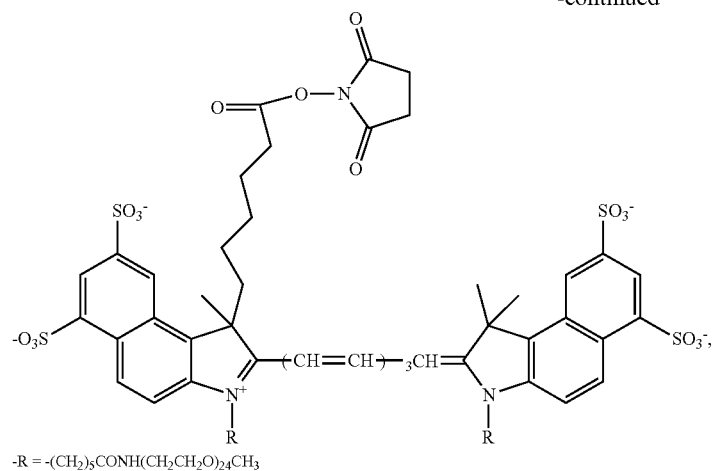
-R = -(CH₂)₅CONH(CH₂CH₂O)₂₄CH₃
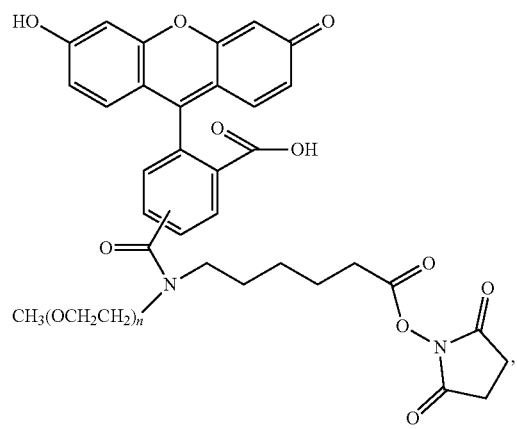
CH₃(OCH₂CH₂)ₙ
n = 24
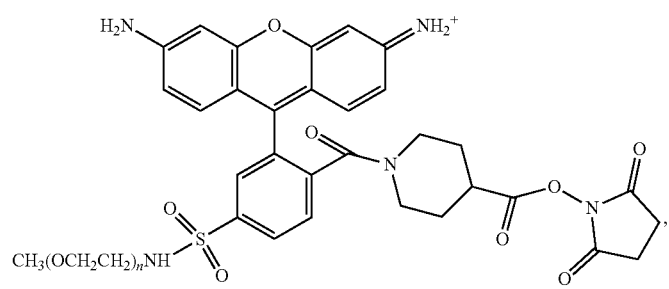
CH₃(OCH₂CH₂)ₙNH
n = 24
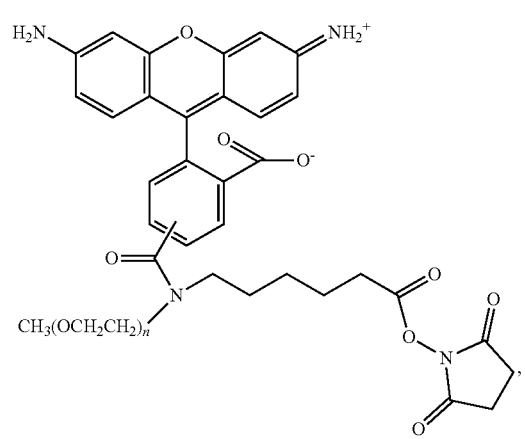
CH₃(OCH₂CH₂)ₙ
n = 24

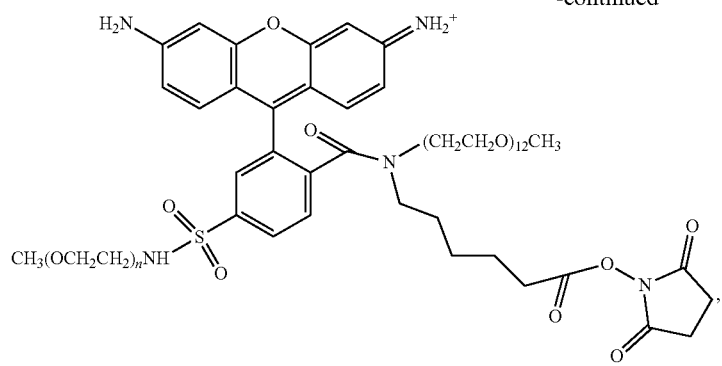
n = 24
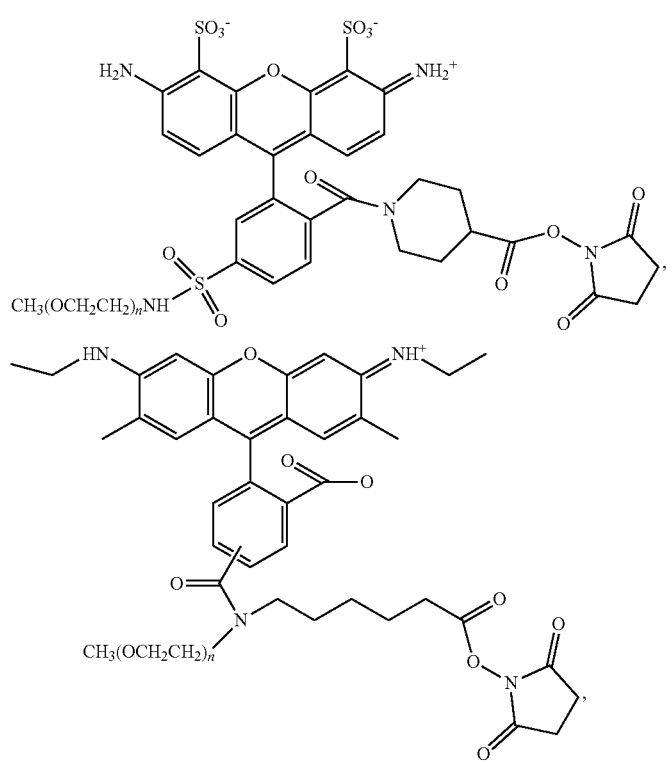
n = 20
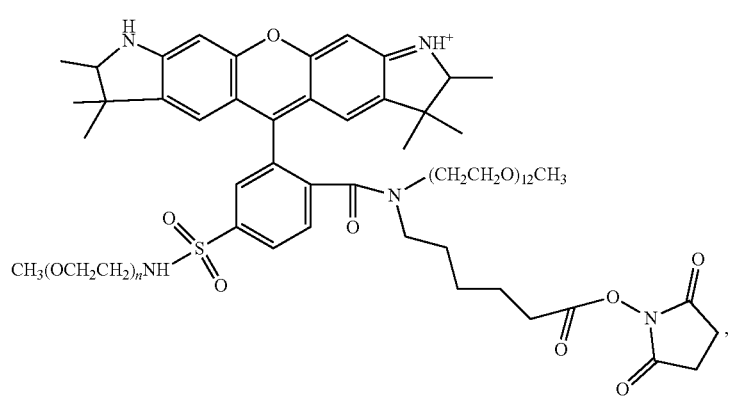
n = 24

-continued
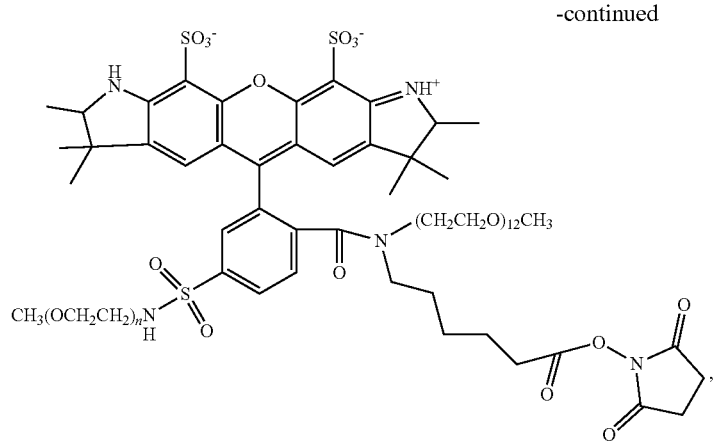
n = 24
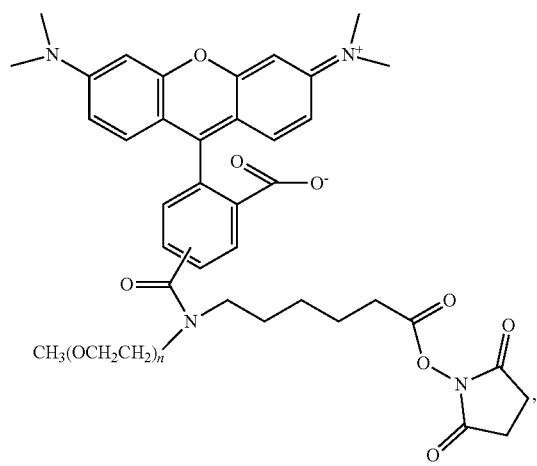
n = 30
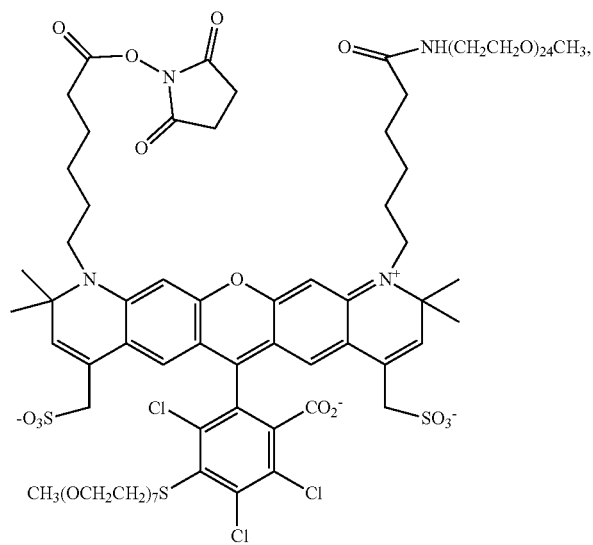

-continued
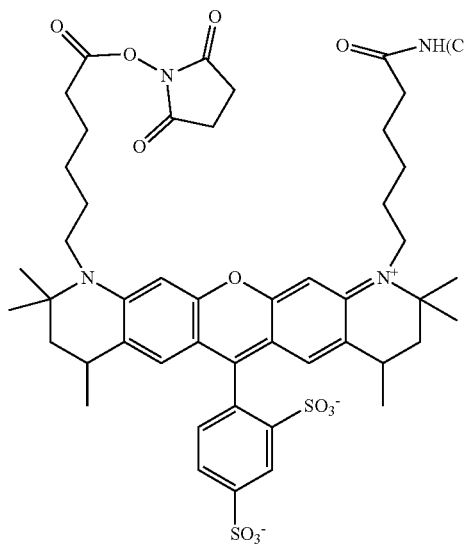
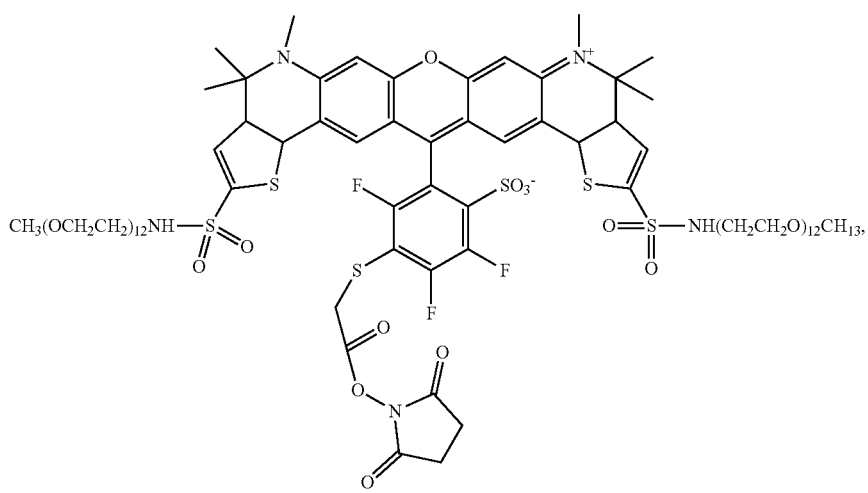
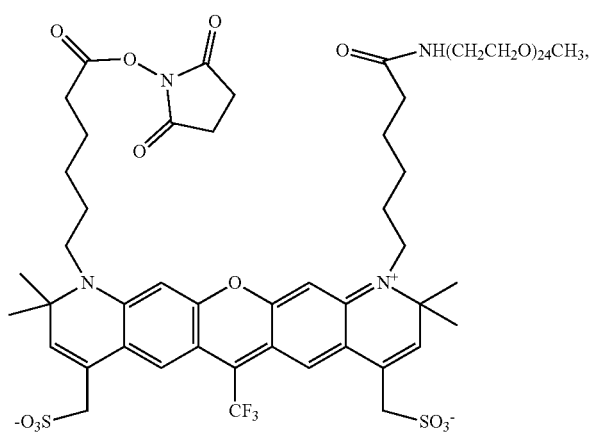

-continued
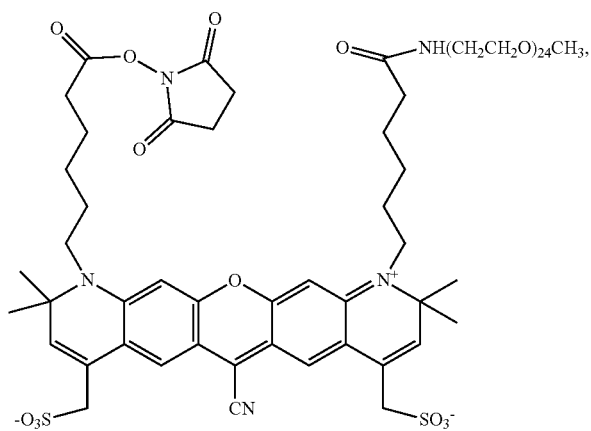
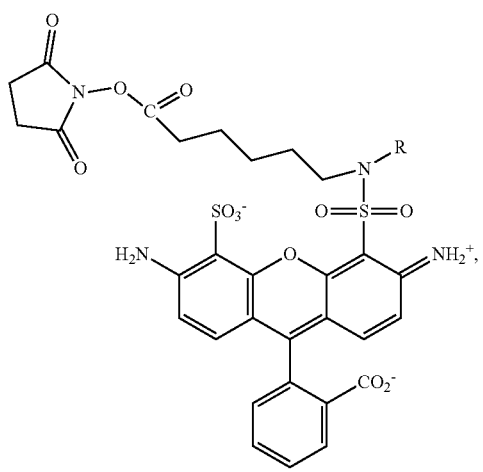
-R = -(CH₂CH₂O)₂₄CH₃
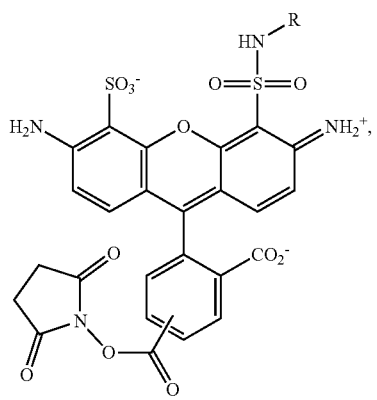
-R = -(CH₂CH₂O)₂₄CH₃
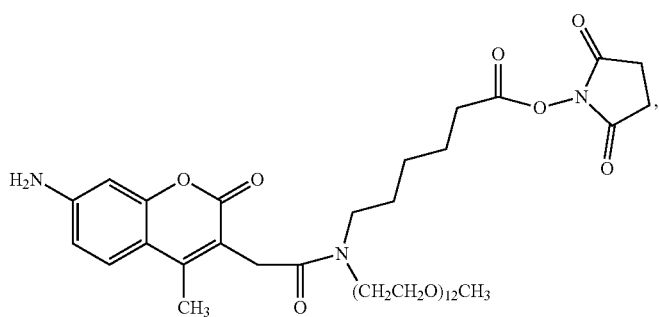

-continued
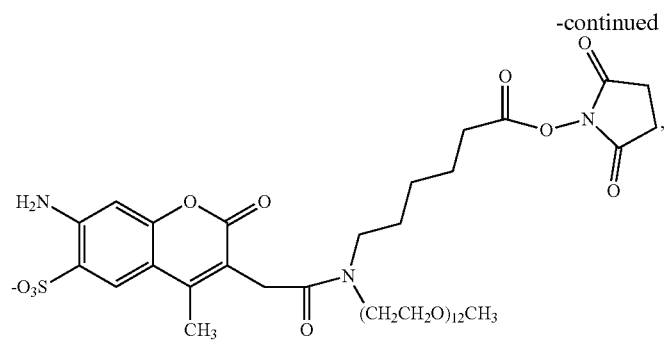
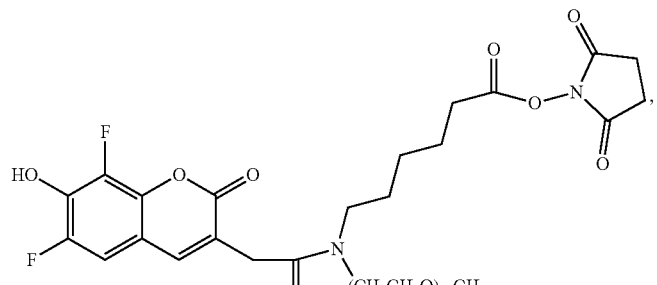
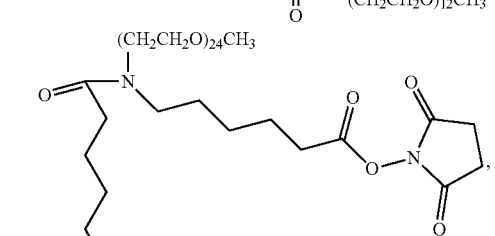
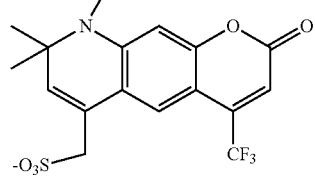
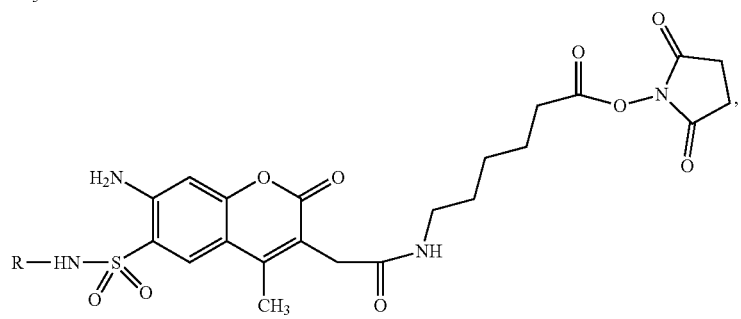
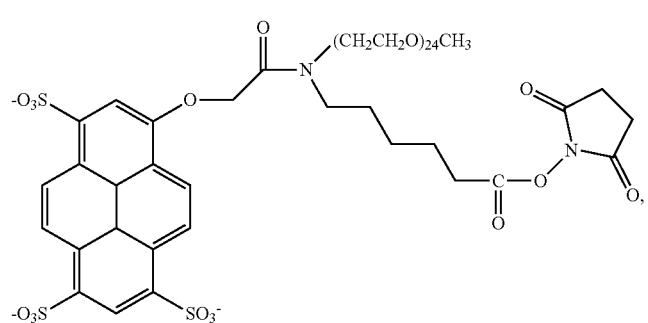

-continued

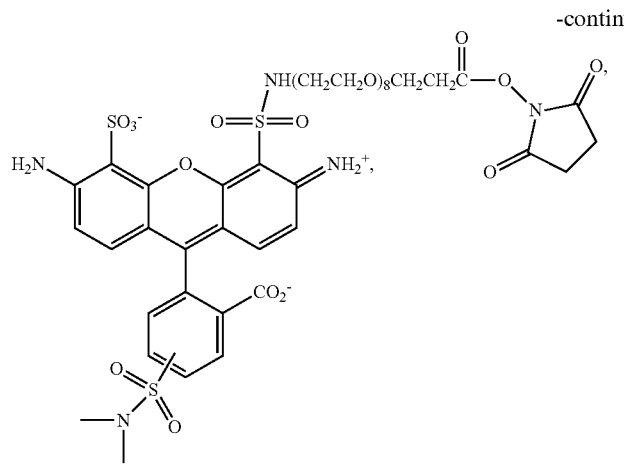

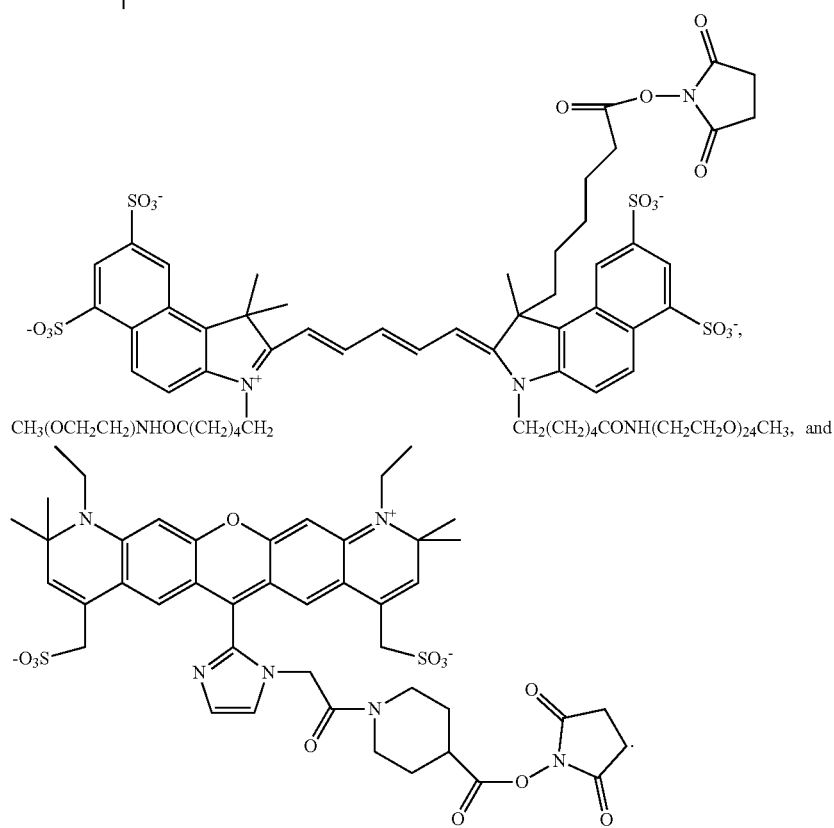

9. The method of claim 1, wherein the amine-reactive dye comprises one or more sulfonate groups.

10. The method of claim 1, wherein the amine-reactive dye comprises one or more water-soluble polymer groups.

11. The method of claim 10, wherein the water-soluble polymer group is a polyethylene glycol.

12. The method of claim 1, wherein the solution comprises from about 1 µg to about 1000 µg of the target protein.

13. The method of claim 1, wherein the ratio of amount of the target protein in microgram (µg) to the amount of reactive dye in nanomoles (nmol) is from about 30:1 to about 1:1.

14. The method of claim 1, wherein the solution further comprises at least one non-target protein, wherein the at least one non-target protein is selected from bovine serum albumin and gelatin.

15. The method of claim 14, wherein the ratio of the combined weight of the target protein and the at least one non-target protein in micrograms (µg) to the amount of reactive dye in nanomoles (nmol) is from about 30:1 to about 1:1.

16. The method of claim 14, wherein the ratio of the weight of the target protein in the solution to the total weight of the at least one non-target protein in the sample solution is from about 10:1 to about 1:10.

17. The method of claim 14, wherein the target protein is preferentially labeled in the presence of the at least one non-target protein.

18. The method of claim 1, wherein the solution further comprises a stabilizer, wherein said stabiliser is bovine serum albumin, gelatin, glycerol, or a combination thereof.

19. The method of claim 18, wherein prior to the preparing of the labeled protein, the target protein is obtained and/or stored in a buffer comprising Tris.

\* \* \* \* \*

UNITED STATES PATENT AND TRADEMARK OFFICE
CERTIFICATE OF CORRECTION

Page 1 of 2

PATENT NO. : 10,837,881 B2
APPLICATION NO. : 15/815035
DATED : November 17, 2020
INVENTOR(S) : Fei Mao et al.

It is certified that error appears in the above-identified patent and that said Letters Patent is hereby corrected as shown below:

In the Claims

• Columns 133-134, first structure:
In Claim 8, the text below the structure reading: "$\begin{array}{c}n = n'\\ n'' = 11\end{array}$" should read: -- $n = n' = n'' = 11$ --.

• Column 133, third structure:
In Claim 8, the text in the lower right of the structure, the "$_n$" should be -- $_{n'}$ --.

• Columns 135-136, second structure:

In Claim 8, replace the part of the structure reading: " 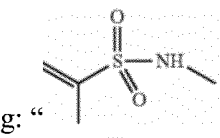 " with: -- 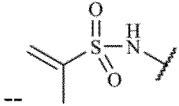 --; and Replace the part of the structure reading: " 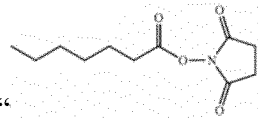 " with: -- 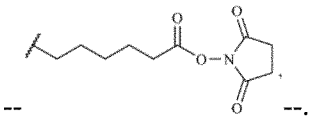 --.

• Column 139, first structure:

In Claim 8, the text in the upper right of the structure reading: " 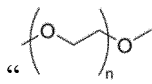 " should read: -- 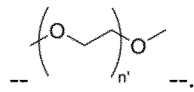 --.

• Column 139, second structure:
In Claim 8, in the text in the lower right of the structure, the "$_n$" should be -- $_{n'}$ --.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

• Columns 141-142, second structure:
In Claim 8, the text in the lower right of the structure reading: " 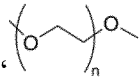 " should read: 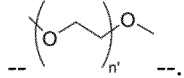.
• Columns 157-158, second structure:
In Claim 8, replace the part of the structure reading: " 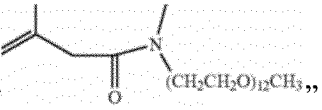 " with: 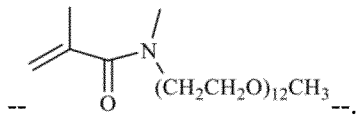.
• Column 160, Line 66:
In Claim 18, the phrase "said stabiliser is" should read: -- said stabilizer is --.